US011034696B2

United States Patent
Ren et al.

(12) United States Patent
(10) Patent No.: US 11,034,696 B2
(45) Date of Patent: *Jun. 15, 2021

(54) COMPOUNDS FOR INHIBITING LRRK2 KINASE ACTIVITY

(71) Applicant: GLAXOSMITHKLINE INTELLECTUAL PROPERTY DEVELOPMENT LIMITED, Brentford (GB)

(72) Inventors: Feng Ren, Shanghai (CN); Yingxia Sang, Shanghai (CN); Weiqiang Xing, Shanghai (CN); Yang Zhan, Shanghai (CN); Baowei Zhao, Shanghai (CN)

(73) Assignee: GLAXOSMITHKLINE INTELLECTUAL PROPERTY DEVELOPMENT LIMITED, Brentford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/480,762

(22) PCT Filed: Jan. 23, 2018

(86) PCT No.: PCT/CN2018/073833
§ 371 (c)(1),
(2) Date: Jul. 25, 2019

(87) PCT Pub. No.: WO2018/137618
PCT Pub. Date: Aug. 2, 2018

(65) Prior Publication Data
US 2019/0359618 A1    Nov. 28, 2019

(30) Foreign Application Priority Data

Jan. 25, 2017  (WO) ................ PCT/CN2017/072589
Jan. 25, 2017  (WO) ................ PCT/CN2017/072614

(51) Int. Cl.
| C07D 487/04 | (2006.01) |
| C07D 407/14 | (2006.01) |
| C07D 413/14 | (2006.01) |
| C07D 487/10 | (2006.01) |
| C07D 491/048 | (2006.01) |
| C07D 498/04 | (2006.01) |
| C07D 498/10 | (2006.01) |
| A61P 25/16 | (2006.01) |
| A61P 25/28 | (2006.01) |
| A61P 25/14 | (2006.01) |

(52) U.S. Cl.
CPC ............ C07D 487/04 (2013.01); A61P 25/16 (2018.01); C07D 407/14 (2013.01); C07D 413/14 (2013.01); C07D 487/10 (2013.01); C07D 491/048 (2013.01); C07D 498/04 (2013.01); C07D 498/10 (2013.01)

(58) Field of Classification Search
CPC .. C07D 487/04; C07D 487/10; C07D 413/14; C07D 407/14; C07D 498/04; C07D 498/10; C07D 471/10; C07D 491/048; C07D 491/052; A61K 31/5377; A61P 25/16; A61P 25/25
USPC ......................................... 544/328; 514/256
See application file for complete search history.

(56) References Cited

FOREIGN PATENT DOCUMENTS

| CN | 105980388 A | 9/2016 |
| WO | WO 2014/134772 A1 | 9/2014 |
| WO | WO 2014/134774 A1 | 9/2014 |
| WO | WO 2016/036586 A1 | 3/2016 |
| WO | WO 2017/012576 A1 | 1/2017 |

OTHER PUBLICATIONS

Layzer, Degenerative Diseases of the Nervous System, Cecil Textbook of Medicine, 20th Edition, vol. 2, pp. 2050-2057 (1996).*
Freshney et al.,Culture of Animal Cells, A Manual of Basic Technique, Alan R. Liss, Inc., 1983, New York, p. 4.*
Dermer et al., Bio/Technology, 1994, 12:320.*

* cited by examiner

*Primary Examiner* — Susanna Moore
(74) *Attorney, Agent, or Firm* — Robert H. Brink; Duke M. Fitch; Edward R. Gimmi

(57) ABSTRACT

Compounds of Formula (I) or pharmaceutically acceptable salt thereof, a pharmaceutical composition comprising these compounds, the use of these compounds and compositions in the treatment of diseases in which LRRK-2 kinase is involved.

18 Claims, No Drawings
Specification includes a Sequence Listing.

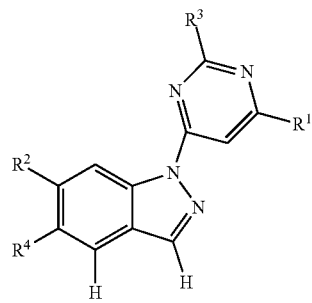

Formula (I)

COMPOUNDS FOR INHIBITING LRRK2 KINASE ACTIVITY

This application is a 371 of International Application No. PCT/CN2018/073833, filed Jan. 23, 2018, which claims the benefit of International Application No. PCT/CN2017/072589, filed Jan. 25, 2017, and International Application No. PCT/CN2017/072614, filed Jan. 25, 2017, which are incorporated herein in their entireties.

FIELD OF THE INVENTION

The present invention relates to novel compounds that inhibit LRRK2 kinase activity, processes for their preparation, compositions containing them and their use in the treatment of diseases associated with or characterized by LRRK2 kinase activity, for example, Parkinson's disease, Alzheimer's disease and amyotrophic lateral sclerosis (ALS).

BACKGROUND OF THE INVENTION

Parkinson's disease (PD) is a neurodegenerative disorder characterized by selective degeneration and cell death of dopaminergic neurons in the substantia nigra region of the brain. Parkinson's disease was generally considered to be sporadic and of unknown etiology, but, in the last 15 years, there has been an important development of the understanding of the genetic basis of this disease and associated pathogenic mechanisms. One area of the development is the understanding of leucine rich repeat kinase 2 (LRRK2) protein. A number of mis-sense mutations in the LRRK2 gene have been strongly linked with autosomal dominant Parkinson's disease in familial studies (See WO2006068492 and WO2006045392; Trinh and Farrer 2013, Nature Reviews in Neurology 9: 445-454; Paisan-Ruiz et al., 2013, J. Parkinson's Disease 3: 85-103). The G2019S mutation in LRRK2 is the most frequent mis-sense mutation and is associated with a clinical phenotype that closely resembles sporadic Parkinson's disease. The LRRK2 G2019S mutation is also present in approximately 1.5% of sporadic Parkinson's disease cases (See Gilks et al., 2005, Lancet, 365: 415-416). In addition to the known pathogenic coding mutations in LRRK2, additional amino acid coding variants of LRRK2 have been identified that are also associated with risk of developing Parkinson's disease (See Ross et al., 2011 Lancet Neurology 10: 898-908). Furthermore, genome-wide association studies (GWAS) have identified LRRK2 as a Parkinson's disease susceptibility locus, which indicates that LRRK2 may be also relevant to sporadic Parkinson's disease cases without mutations that cause amino acid substitutions in the LRRK2 protein. (See Satake et al., 2009 Nature Genetics 41:1303-1307; Simon-Sanchez et al 2009 Nature Genetics 41: 1308-1312)

LRRK2 is a member of the ROCO protein family and all members of this family share five conserved domains. The most common pathogenic mutation G2019S occurs in the highly conserved kinase domain of LRRK2. This mutation confers an increase in the LRRK2 kinase activity in in vitro enzyme assays of recombinant LRRK2 proteins (See Jaleel et al., 2007, Biochem J, 405: 307-317) and in LRRK2 proteins purified from G2019S PD patient-derived cells (See Dzamko et al., 2010 Biochem. J. 430: 405-413). A less frequent LRRK2 pathogenic mutation that confers amino acid substitution at a different residue, R1441, has also been shown to elevate LRRK2 kinase activity by decreasing the rate of GTP hydrolysis by the GTPase domain of LRRK2 (See Guo et al., 2007 Exp Cell Res. 313: 3658-3670; West et al., 2007 Hum. Mol Gen. 16: 223-232). Moreover, phosphorylation of Rab protein physiologic substrates of LRRK2 has been shown to be increased by a range of Parkinson's disease pathogenic mutations of LRRK2 (See Steger et al., 2016 eLife 5 e12813). Therefore, the evidence indicates that the kinase and GTPase activities of LRRK2 are important for pathogenesis, and that the LRRK2 kinase domain may regulate overall LRRK2 function (See Cookson, 2010 Nat. Rev. Neurosci. 11: 791-797).

There is evidence to show that the increased LRRK2 kinase activity is associated with neuronal toxicity in cell culture models (See Smith et al., 2006 Nature Neuroscience 9: 1231-1233) and kinase inhibitor compounds protect against LRRK2-mediated cell death (See Lee et al., 2010 Nat. Med. 16: 998-1000). LRRK2 has also been reported to act as a negative regulator of microglial-mediated clearance of alpha-synuclein (See Maekawa et al., 2016 BMC Neuroscience 17:77), suggesting a possible utility of LRRK2 inhibitors in promoting clearance of neurotoxic forms of alpha-synuclein in the treatment of Parkinson's disease.

Induced pluripotent stem cells (iPSCs) derived from LRRK2 G2019S Parkinson's disease patients have been found to exhibit defects in neurite outgrowth and increased susceptibility to rotenone, that may be ameliorated by either genetic correction of the G2019S mutation or treatment of cells with small molecule inhibitors of LRRK2 kinase activity (See Reinhardt et al., 2013 Cell Stem Cell 12: 354-367). Mitochondrial DNA damage has been reported as a molecular marker of vulnerable dopamine neurons in substantia nigra of postmortem Parkinson's disease specimens (See Sanders et al 2014 Neurobiol. Dis. 70: 214-223). Increased levels of such mitochondrial DNA damage associated with LRRK2 G2019S mutation in isPCs is blocked by genetic correction of the G2019S mutation (See Sanders et al., 2014 Neurobiol. Dis. 62: 381-386).

Additional evidence links LRRK2 function and dysfunction with autophagy-lysosomal pathways (See Manzoni and Lewis, 2013 Faseb J. 27:3234-3429). LRRK2 proteins confer defects in chaperone-mediated autophagy that negatively impact the ability of cells to degrade alpha-synuclein (Orenstein et al., 2013 Nature Neurosci. 16 394-406). In other cell models, selective LRRK2 inhibitors have been shown to stimulate macroautophagy (See Manzoni et al., 2013 BBA Mol. Cell Res. 1833: 2900-2910). These data suggest that small molecule inhibitors of LRRK2 kinase activity may have utility in the treatment of diseases characterized by defects in cellular proteostasis that result from aberrant autophagy/lysosomal degradation pathways including forms of Parkinson's disease associated with GBA mutations (See Swan and Saunders-Pullman 2013 Curr. Neurol. Neurosci Rep. 13: 368), other alpha-synucleinopathies, tauopathies, Alzheimer's disease (See Li et al., 2010 Neurodegen. Dis. 7: 265-271) and other neurodegenerative diseases (See Nixon 2013 Nat. Med. 19: 983-997) and Gaucher disease (See Westbroek et al., 2011 Trends. Mol. Med. 17: 485-493). As promoters of autophagy, small molecule inhibitors of LRRK2 kinase may also have utility in treatment of other diseases including diabetes, obesity, motor neuron disease, epilepsy and some cancers (See Rubinsztein et al., 2012 Nat. Rev. Drug Discovery 11: 709-730), pulmonary diseases such as chronic obstructive pulmonary disease and idiopathic pulmonary fibrosis (See Araya et al., 2013 Intern. Med. 52: 2295-2303) and autoimmune diseases susch as systemic lupus erythematosus (See Martinez et al., 2016 Nature 533: 115-119). As promoters of autophagy and phagocytic processes, small molecule inhibitors of LRRK2 kinase may also have utility in augmenting host responses in treatment of a range of intracellular bacterial infections, parasitic infections and viral infections, including diseases such as tuberculosis (See Rubinsztein et al., 2012 Nat. Rev. Drug Discovery 11: 709-730; Araya et al., 2013 Intern. Med. 52: 2295-2303; Gutierrez, Biochemical Society Conference; Leucine rich repeat kinase 2: ten years along the road to therapeutic intervention, Henley Business School, UK 12 Jul. 2016), HIV, West Nile Virus and chikungunya virus (see Shoji-Kawata et al., 2013 Nature 494: 201-206). LRRK2 inhibitors may have utility in treatment of such diseases alone, or in combination with drugs that directly target the infectious agent. Further, significantly elevated levels of LRRK2 mRNA have also been observed in fibroblasts of Niemann-Pick Type C (NPC) disease patients compared with fibroblasts of normal subjects, which indicates that aberrant LRRK2 function may play a role in lysosomal disorders (See Reddy et al., 2006 PLOS One 1 (1):e19 doi: 10.1371/journal.pone.0000019—supporting information Dataset S1). This observation suggests that LRRK2 inhibitors may have utility for treatment of NPC.

The PD-associated G2019S mutant form of LRRK2 has also been reported to enhance phosphorylation of tubulin-associated Tau (See Kawakami et al., 2012 PLoS ONE 7: e30834, doi 10.1371), and disease models have been proposed in which LRRK2 acts upstream of the pathogenic effects of Tau and alpha-synuclein (See Taymans & Cookson, 2010, BioEssays 32: 227-235). In support of this, LRRK2 expression has been associated with increased aggregation of insoluble Tau, and increased Tau phosphorylation, in a transgenic mouse model (See Bailey et al., 2013 Acta Neuropath. 126:809-827). Over-expression of the PD pathogenic mutant protein LRRK2 R1441G is reported to cause symptoms of Parkinson's disease and hyperphosphorylation of Tau in transgenic mouse models (See Li, Y. et al. 2009, Nature Neuroscience 12: 826-828). Therefore, these data suggest that LRRK2 inhibitors of kinase catalytic activity may be useful for the treatment of tauopathy diseases characterized by hyperphosphorylation of Tau such as argyrophilic grain disease, Pick's disease, corticobasal degeneration, progressive supranuclear palsy and inherited frontotemporal dementia and parkinsonism linked to chromosome 17 (FTDP-17) (See Goedert, M and Jakes, R (2005) Biochemica et Biophysica Acta 1739, 240-250). In addition, LRRK2 inhibitors may have utility in treatment of other diseases characterized by diminished dopamine levels such as withdrawal symptoms/relapse associated with drug addiction (See Rothman et al., 2008, Prog. Brain Res, 172: 385).

Other studies have also shown that overexpression of the G2019S mutant form of LRRK2 confers defects in subventricular zone (SVZ) neuroprogenitor cell proliferation and migration in transgenic mouse models (See Winner et al., 2011 Neurobiol. Dis. 41: 706-716) and reduces neurite length and branching cell culture models (See Dachsel et al., 2010 Parkinsonism & Related Disorders 16: 650-655). Moreover, it was reported that agents that promote SVZ neuroprogenitor cell proliferation and migration also improve neurological outcomes following ischemic injury in rodent models of stroke (See Zhang et al., 2010 J. Neurosci. Res. 88: 3275-3281). These findings suggest that compounds that inhibit aberrant activity of LRRK2 may have utility for the treatments designed to stimulate restoration of CNS functions following neuronal injury, such as ischemic stroke, traumatic brain injury, spinal cord injury.

Mutations in LRRK2 have also been identified that are clinically associated with the transition from mild cognitive impairment (MCI) to Alzheimer's disease (See WO2007149798). These data suggest that inhibitors of LRRK2 kinase activity may be useful for the treatment diseases such as Alzheimer's disease, other dementias and related neurodegenerative disorders.

Aberrant regulation of normal LRRK2 proteins is also observed in some disease tissues and models of disease. Normal mechanisms of translational control of LRRK2 by miR-205 are perturbed in some sporadic PD cases, where significant decreases in miR-205 levels in PD brain samples concur with elevated LRRK2 protein levels in those samples (See Cho et al., (2013) Hum. Mol. Gen. 22: 608-620). Therefore, LRRK2 inhibitors may be used in treatment of sporadic PD patients who have elevated levels of normal LRRK2 proteins.

In an experimental model of Parkinson's disease in marmosets, an elevation of LRRK2 mRNA is observed in a manner that correlates with the level of L-Dopa induced dyskinesia (See Hurley, M. J et al., 2007 Eur. J. Neurosci. 26: 171-177). This suggests that LRRK2 inhibitors may have a utility in amelioration of such dyskinesias.

Significantly elevated levels of LRRK2 mRNA have been reported in ALS patient muscle biopsy samples (See Shtilbans et al., 2011 Amyotrophic Lateral Sclerosis 12: 250-256) It is suggested that elevated levels of LRRK2 kinase activity may be a characteristic feature of ALS. Therefore, this observation indicated that LRRK2 inhibitor may have utility for treatment of ALS.

There is also evidence indicating that LRRK2 kinase activity may play a role in mediating microglial proinflammatory responses (See Moehle et al., 2012, J. Neuroscience 32: 1602-1611). This observation suggests a possible utility of LRRK2 inhibitors for treatment of aberrant neuroinflammatory mechanisms that contribute a range of neurodegenerative diseases, including Parkinson's disease, Alzheimer's disease, multiple sclerosis, HIV-induced dementia, amyotrophic lateral sclerosis, ischemic stroke, traumatic brain injury and spinal cord injury. Some evidence also indicates that LRRK2 plays a role in regulating neuronal progenitor differentiation in vitro (See Milosevic, J. et al., 2009 Mol. Neurodegen. 4: 25). This evidence suggests that inhibitors of LRRK2 may have a utility in production of neuronal progenitor cells in vitro for consequent therapeutic application in cell based-treatment of CNS disorders.

It has been reported that Parkinson's disease patients bearing LRRK2 G2019S mutation display increased frequency of non-skin cancers, including renal, breast, lung, prostate cancers as well as acute myelogenous leukemia (AML). Since there is evidence to show that G2019S mutation in LRRK2 increases catalytic activity of the LRRK2 kinase domain, small molecule inhibitors of LRRK2 may have a utility in treatment of cancers, for example kidney cancer, breast cancer, lung cancer, prostate cancer (e.g. solid tumors) and blood cancer (See. AML; Saunders-Pullman et al., 2010, Movement Disorders, 25:2536-2541; Inzelberg et al., 2012 Neurology 78: 781-786). Amplification and over-expression of LRRK2 has also been reported in papillary renal and thyroid carcinomas, where co-operativity between LRRK2 and the MET oncogene may promote tumor cell growth and survival (See Looyenga et al., 2011 PNAS 108: 1439-1444.)

Some studies suggested that genetic association of common LRRK2 variants with susceptibility to ankylosing spondylitis (See Danoy P, et al., 2010. PLoS Genet.; 6(12): e1001195; and leprosy infection. (See Zhang F R, et al. 2009, N Engl J Med. 361:2609-18.) These findings suggest that inhibitors of LRRK2 may have a utility in the treatment of ankylosing spondylitis and leprosy infection.

Meta-analysis of three genome wide associated scans for Crohn's disease identified a number of loci associated with the disease, including the locus containing the LRRK2 gene (See Barrett et al., 2008, Nature Genetics, 40: 955-962). Evidence has also emerged that LRRK2 is an IFN-γ target gene that may be involved in signaling pathways relevant to Crohn's disease pathogenesis (See Gardet et al., 2010, J. Immunology, 185: 5577-5585). These findings suggest that inhibitors of LRRK2 may have utility in the treatment of Crohn's disease.

As an IFN-γ target gene, LRRK2 may also play a role in T cell mechanisms that underlie other diseases of the immune system such as multiple sclerosis and rheumatoid arthritis. Further potential utility of LRRK2 inhibitors comes from the reported finding that B lymphocytes constitute a major population of LRRK2 expressing cells (See Maekawa et al. 2010, BBRC 392: 431-435). This suggests that LRRK2 inhibitors may be effective in treatment of diseases of the immune system for which B cell depletion is, or may be, effective in diseases such as lymphomas, leukemias, multiple sclerosis (See Ray et al., 2011 J. Immunol. 230: 109), rheumatoid arthritis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, Sjogren's syndrome, Devic's disease and inflammatory myopathies (See Engel et al., 2011 Pharmacol. Rev. 63: 127-156; Homam et al., 2010 J. Clin. Neuromuscular Disease 12: 91-102).

WO2016036586 and WO2017012576 disclose a series of compounds described as inhibitors of LRRK2 kinase and their use in the treatment of diseases, including, inter alia, Parkinson's disease. Unmet needs exist for new treatments that will halt or slow disease progression both in terms of motor (e.g. control of gait dysfunction, freezing, and postural imbalance) and non-motor symptoms (e.g. PD-associated dementia), reducing the need for escalating use of symptomatic medications and associated long-term adverse effects of currently available treatment (e.g. dyskinesia and on/off fluctuations) maintaining independence for longer.

SUMMARY OF THE INVENTION

The present invention provides, in a first aspect, compounds of Formula (I) and salts thereof:

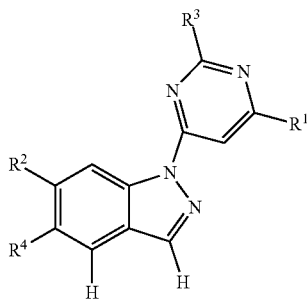

Formula (I)

wherein
$R^1$ is
a) an N-linked 6-9 membered fused bicyclic heterocyclyl optionally substituted with one, two or three substituents independently selected from the group consisting of oxo, halo, hydroxyl, $C_{1-3}$alkyl and $C_{1-3}$alkoxy, wherein $C_{1-3}$alkyl and $C_{1-3}$alkoxy may be optionally substituted with one or two substituents independently selected from the group consisting of halo, hydroxyl, unsubstituted $C_{1-3}$alkyl and unsubstituted $C_{1-3}$alkoxy; or
b) an N-linked 7-10 membered heterospirane ring optionally substituted with one, two or three substituents independently selected from the group consisting of oxo, halo, hydroxyl, $C_{1-3}$alkyl and $C_{1-3}$alkoxy, wherein $C_{1-3}$alkyl and $C_{1-3}$alkoxy may be optionally substituted with one or two substituents independently selected from the group consisting or halo, hydroxyl, unsubstituted $C_{1-3}$alkyl and unsubstituted $C_{1-3}$ alkoxy, and with the proviso that $R^1$ is not 2-oxa-6-azaspiro[3.4]octan-6-yl;

$R^2$ is selected from the group consisting of:
a) 4-7 membered heterocyclyl ring optionally substituted with one, two or three substituents independently selected from the group consisting of $C_{1-3}$alkyl, which alkyl group is optionally substituted with one, two or three substituents independently selected from the group consisting of halo, hydroxyl, $CO_2H$, $-CH_2CH_2-$ and $C_{1-3}$alkoxy;
cyano,
halo,
hydroxyl,
$-SO_2OH_3$,
$-COCH_3$, and
$-COCH_2OH$,
wherein when the 4-7 membered heterocyclyl ring contains a substitutable nitrogen atom, the group of substituents also includes a 4-6 membered heterocyclyl ring which is optionally substituted with one or two substituents independently selected from the group consisting of cyano, halo, hydroxyl, $C_{1-3}$alkyl, $C_{1-3}$alkoxyl, $CH_2OH$ and $C_{3-6}$cycloalkyl which $C_{3-6}$cycloalkyl group is optionally substituted with one or two substituents independently selected from the group consisting of halo, hydroxyl, cyano, $CH_2OH$, unsubstituted $C_{1-3}$alkyl and unsubstituted $C_{1-3}$ alkoxyl, with the proviso that the 4-6 membered heterocyclyl ring is attached to said substitutable nitrogen atom;
b) $-O-$4-6 membered heterocyclyl ring wherein the heterocyclyl ring is optionally substituted with one or two substituents independently selected from the group consisting of: cyano, hydroxyl, $C_{1-3}$alkyl, $C_{1-3}$alkoxyl, $CH_2OH$ and $-CO_2H$;
c) $C_{3-6}$ cycloalkyl optionally substituted with one or two substituents independently selected from the group consisting of cyano, halo, hydroxyl, $C_{1-3}$alkyl, $C_{1-3}$alkoxyl, $CO_2H$ and a 4-6 membered heterocyclyl ring;
d) $-O-C_{3-6}$ cycloalkyl wherein the cycloalkyl group is optionally substituted with one or two substituents independently selected from the group consisting of cyano, hydroxyl, $C_{1-3}$alkyl, $C_{1-3}$alkoxyl, $CH_2OH$ and $CO_2H$; and
e) $C_{1-6}$alkoxy optionally substituted by one or two substituents independently selected from the group consisting of halo, hydroxyl, $C_{1-3}$alkyl, $C_{1-3}$alkoxyl, $CO_2H$ and a 4-6 membered heterocyclyl ring;

$R^3$ is selected from the group consisting of halo, CN, $C_{1-3}$ alkyl, $C_{1-3}$ alkoxy, $C_{1-3}$haloalkyl, $C_{1-3}$haloalkoxy and $C_{3-6}$ cycloalkyl; and $R^4$ is selected from the group consisting of H, halo, CN, $C_{1-3}$alkyl, $C_{1-3}$ alkoxy, $C_{1-3}$haloalkyl, $C_{1-3}$haloalkoxy and $C_{3-6}$ cycloalkyl.

In a further aspect of the invention, the invention provides a pharmaceutical composition comprising a compound of Formula (I) or a pharmaceutically acceptable salt thereof and a pharmaceutically acceptable carrier.

A further aspect of the invention provides a compound of Formula (I) or a pharmaceutically acceptable salt thereof for use in the treatment or prevention of Parkinson's disease or Alzheimer's disease.

DETAILED DESCRIPTION OF THE INVENTION

The foregoing and other aspects of the present invention will now be described in more detail with respect to the description and methodologies provided herein. It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms "a", "an" and "the" are intended to include the plural forms as well, unless the context clearly indicates otherwise. Also, as used herein, "and/or" refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Generally, the nomenclature used herein and the laboratory procedures in organic chemistry, medicinal chemistry, biology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

A. Definitions

As used herein, "alkyl" refers to a monovalent, saturated hydrocarbon chain having a specified number of carbon atoms. For example, $C_{1-3}$ alkyl refers to an alkyl group having from 1 to 3 carbon atoms. Alkyl groups may be straight or branched. In some embodiments, branched alkyl groups may have one, two, or three branches. Exemplary alkyl groups include, but are not limited to, methyl, ethyl, and propyl (n-propyl and isopropyl).

As used herein, "alkoxy" refers to the group —O-alkyl. For example, $C_{1-6}$ alkoxy groups contain from 1 to 6 carbon atoms. $C_{1-3}$ alkoxy groups contain from 1 to 3 carbon atoms. Exemplary alkoxy groups include, but are not limited to, methoxy, ethoxy, propoxy, butoxyl, pentyloxy, and hexyloxy.

As used herein, "cycloalkyl" refers to a saturated monocyclic hydrocarbon ring having a specified number of carbon atoms. For example, $C_{3-6}$ cycloalkyl contains 3 to 6 carbon atoms as member atoms in the ring. Examples of $C_{3-6}$ cycloalkyl include cyclopropyl, cyclobutyl, cyclopentyl and cyclohexyl.

As used herein, "halogen" refers to fluorine (F), chlorine (Cl), bromine (Br), or iodine (I). "Halo" refers to the halogen radicals: fluoro (—F), chloro (—Cl), bromo (—Br), or iodo (—I).

As used herein, "haloalkyl" refers to an alkyl group, as defined above, having one or more halogen atoms selected from F, Cl, Br, or I, which are substituted on any or all of the carbon atoms of the alkyl group by replacing hydrogen atoms attached to the carbon atoms and which may be the same or different. For example, $C_{1-3}$haloalkyl refers to a $C_{1-3}$alkyl group substituted with one or more halogen atoms. In some embodiments, "haloalkyl" refers to an alkyl group substituted with one or more halogen atoms independently selected from F or Cl. Exemplary haloalkyl groups include, but are not limited to, chloromethyl, bromoethyl, trifluoromethyl, and dichloromethyl.

As used herein, "haloalkoxy" refers to the group —O-haloalkyl. For example, $C_{1-3}$ haloalkoxy groups contain from 1 to 6 carbon atoms.

As used herein, "heterocyclyl" is a monovalent radical derived by removal of a hydrogen atom from a saturated monocyclic ring, which ring consists of ring carbon atoms and 1 or more ring heteroatoms independently selected from nitrogen, oxygen or sulphur. In one embodiment, the ring-heteroatoms are independently selected from nitrogen or oxygen. The number of ring atoms may be specified. For example, a "5-6 membered heterocyclyl" is a heterocyclyl as defined above consisting of 5-6 ring atoms. The term nitrogen containing heterocyclyl refers to heterocyclyl ring as defined above that contains at least one nitrogen ring atom. The term oxygen containing heterocyclyl should be construed in an analogous manner. The expression —O-4-6 membered heterocyclyl ring refers to heterocyclyl ring as defined above consisting of 4-6 ring atoms that is linked to the core through an oxygen atom. Other ring heteroatoms (nitrogen, oxygen or sulphur) may additionally be present. Examples of herterocyclyl rings include, but are not limited to, oxetanyl, azetidinyl, tetrahydrofuranyl (including, for example, tetrahydrofuran-2-yl and tetrahydrofuran-3-yl), pyrrolidinyl (including, for example, pyrrolidin-1-yl and pyrrolidin-3-yl), tetrahydro-2H-pyrany or oxanyl (including, for example, tetrahydro-2H-pyran-3-yl or oxayn-3-yl and tetrahydro-2H-pyran-4-yl or oxan-4-yl), piperidinyl (including, for example, piperidin-3-yl and piperidin-4-y) and morpholinyl (including, for example, morpholin-2-yl and morpholin-4-yl).

The term "fused bicyclic heterocyclyl" refers to a monovalent radical derived by removal of a hydrogen atom from a saturated bicyclic ring (two rings sharing one bond), which consists of carbon atoms and 1, 2 or 3 heteroatoms independently selected from nitrogen, oxygen or sulphur with the proviso that only one heteroatom may be oxygen. The number of atoms in the bicyclic heterocyclyl may be specified. For example, the term 6-9 membered fused bicyclic heterocyclyl refers to a fused bicyclic heterocyclyl that has a total of 6 to 9 atoms in the two rings. The term N-linked 6-9 membered fused bicyclic heterocyclyl refers to a 6-9 membered fused bicyclic heterocyclyl as defined above that contains at least one nitrogen ring atom through which it is linked to the core. One or two other ring heteroatoms (nitrogen, oxygen or sulphur) may additionally be present with the proviso that only one ring heteroatom may be oxygen. In one embodiment, the term N-linked 6-9 membered fused bicyclic heterocyclyl refers to a 6-9 membered fused bicyclic heterocyclyl as defined above that contains at least one nitrogen ring atom through which it is linked to the core. One or two other ring heteroatoms (nitrogen or oxygen) may additionally be present with the proviso that only one ring heteroatom may be oxygen. Examples of fused bicyclic heterocyclyl rings and N-linked fused bicyclic heterocyclyl rings include, but are not limited to,

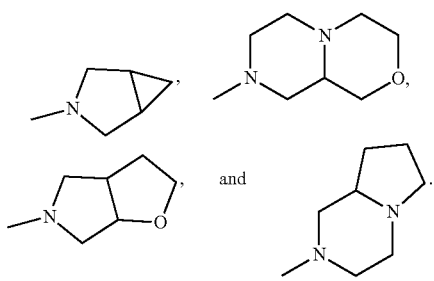

As used herein, the term "heterospirane ring" refers to a monovalent radical derived by removal of a hydrogen atom from two rings connected through just one atom. The heterospirane ring consists of carbon atoms and 1 or more heteroatoms independently selected from nitrogen and oxygen but the spiro atom must be carbon. The number of atoms in the heterospirane ring may be specified. For example, a 7-10 membered heterospirane ring refers to a heterospirane ring that has a total of 7 to 10 atoms in the two rings (including the spiro-atom). The term "N-linked 7-10 membered heterospirane ring" refers to a 7-10 membered heterospirane ring as defined above that contains one nitrogen ring atom through which it is linked to the core. Examples of heterospirane rings and N-linked heterospirane rings include, but are not limited to,

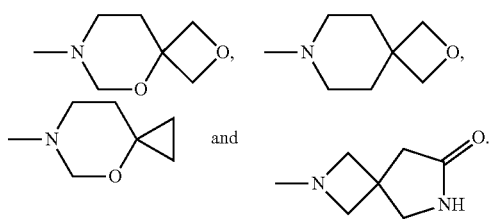

As used herein, "substituted" in reference to a group indicates that one or more hydrogen atom attached to a member atom (e.g., carbon atom) within the group is replaced with a substituent selected from the group of defined substituents. It should be understood that the term "substituted" includes the implicit provision that such substitution is in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituent, one or more (as appropriate) member atom within the group may be substituted. In addition, a single member atom within the group may be substituted with more than one substituent as long as such substitution is in accordance with the permitted valence of the atom.

As used herein, "optionally substituted" indicates that a particular group may be unsubstituted, or may be substituted as further defined.

As used herein, the term "disease" refers to any alteration in state of the body or of some of the organs, interrupting or disturbing the performance of the functions and/or causing symptoms such as discomfort, dysfunction, distress, or even death to the person afflicted or those in contact with a person. A disease can also include a distemper, ailing, ailment, malady, disorder, sickness, illness, complain, interdisposition and/or affectation.

As used herein, "treat", "treating" or "treatment" in reference to a disease means: (1) to ameliorate the disease or one or more of the biological manifestations of the disease, (2) to interfere with (a) one or more points in the biological cascade that leads to or is responsible for the disease or (b) one or more of the biological manifestations of the disease, (3) to alleviate one or more of the symptoms or effects associated with the disease, (4) to slow the progression of the disease or one or more of the biological manifestations of the disease, and/or (5) to diminish the likelihood of severity of a disease or biological manifestations of the disease. Symptomatic treatment refers to treatment as referred to in point (1), (3) and (5). Disease modifying treatment refers to treatment as defined in point (2) and (4).

As used herein, "prevent", "preventing" or "prevention" means the prophylactic administration of a drug to diminish the likelihood of the onset of or to delay the onset of a disease or biological manifestation thereof.

As used herein, "subject" means a mammalian subject (e.g., dog, cat, horse, cow, sheep, goat, monkey, etc.), and human subjects including both male and female subjects, and including neonatal, infant, juvenile, adolescent, adult and geriatric subjects, and further including various races and ethnicities including, but not limited to, white, black, Asian, American Indian and Hispanic.

As used herein, "pharmaceutically acceptable salt(s)" refers to salt(s) that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively.

As used herein, "therapeutically effective amount" in reference to a compound of the invention or other pharmaceutically-active agent means an amount of the compound sufficient to treat or prevent the patient's disease but low enough to avoid serious side effects (at a reasonable benefit/risk ratio) within the scope of sound medical judgment. A therapeutically effective amount of a compound will vary with the particular compound chosen (e.g. consider the potency, efficacy, and half-life of the compound); the route of administration chosen; the disease being treated; the severity of the disease being treated; the age, size, weight, and physical disease of the patient being treated; the medical history of the patient to be treated; the duration of the treatment; the nature of concurrent therapy; the desired therapeutic effect; and like factors, but can nevertheless be routinely determined by the skilled artisan.

B. Compounds

This invention provides, in a first aspect, a compound of Formula (I) or a salt thereof:

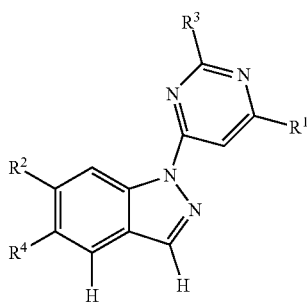

Formula (I)

wherein

R¹ is
a) an N-linked 6-9 membered fused bicyclic heterocyclyl optionally substituted with one, two or three substituents independently selected from the group consisting of oxo, halo, hydroxyl, $C_{1-3}$alkyl and $C_{1-3}$alkoxy, wherein $C_{1-3}$alkyl and $C_{1-3}$alkoxy may be optionally substituted with one or two substituents independently selected from the group consisting of halo, hydroxyl, unsubstituted $C_{1-3}$alkyl and unsubstituted $C_{1-3}$alkoxy; or
b) an N-linked 7-10 membered heterospirane ring optionally substituted with one, two or three substituents independently selected from the group consisting of oxo, halo, hydroxyl, $C_{1-3}$alkyl and $C_{1-3}$alkoxy, wherein $C_{1-3}$alkyl and $C_{1-3}$alkoxy may be optionally substituted with one or two substituents independently selected from the group consisting or halo, hydroxyl, unsubstituted $C_{1-3}$alkyl and $C_{1-3}$ alkoxy, and with the proviso that R¹ is not 2-oxa-6-azaspiro[3.4]octan-6-yl;

R² is selected from the group consisting of:
a) 4-7 membered heterocyclyl ring optionally substituted with one, two or three substituents independently selected from the group consisting of $C_{1-3}$alkyl, which alkyl group is optionally substituted with one, two or three substituents independently selected from the group consisting of halo, hydroxyl, $CO_2H$, —$CH_2CH_2$— and $C_{1-3}$alkoxy;
cyano,
halo,
hydroxyl,
—$SO_2CH_3$,
—$COCH_3$, and
—$COCH_2OH$,
wherein when the 4-7 membered heterocyclyl ring contains a substitutable nitrogen atom, the group of substituents also includes a 4-6 membered heterocyclyl ring which is optionally substituted with one or two substituents independently selected from the group consisting of cyano, halo, hydroxyl, $C_{1-3}$ alkyl, $C_{1-3}$alkoxyl, $CH_2OH$ and $C_{3-6}$cycloalkyl which $C_{3-6}$cycloalkyl group is optionally substituted with one or two substituents independently selected from the group consisting of halo, hydroxyl, cyano, $CH_2OH$, unsubstituted $C_{1-3}$alkyl and unsubstituted $C_{1-3}$ alkoxyl, with the proviso that the 4-6 membered heterocyclyl ring is attached to said substitutable nitrogen atom;
b) —O-4-6 membered heterocyclyl ring wherein the heterocyclyl ring is optionally substituted with one or two substituents independently selected from the group consisting of: cyano, hydroxyl, $C_{1-3}$alkyl, $C_{1-3}$alkoxyl, $CH_2OH$ and —$CO_2H$;
c) $C_{3-6}$ cycloalkyl optionally substituted with one or two substituents independently selected from the group consisting of cyano, halo, hydroxyl, $C_{1-3}$alkyl, $C_{1-3}$alkoxyl, $CO_2H$ and a 4-6 membered heterocyclyl ring;
d) —O—$C_{3-6}$ cycloalkyl wherein the cycloalkyl group is optionally substituted with one or two substituents independently selected from the group consisting of cyano, hydroxyl, $C_{1-3}$alkyl, $C_{1-3}$alkoxyl, $CH_2OH$ and $CO_2H$; and
e) $C_{1-6}$alkoxy optionally substituted by one or two substituents independently selected from the group consisting of halo, hydroxyl, $C_{1-3}$alkyl, $C_{1-3}$alkoxyl, $CO_2H$ and a 4-6 membered heterocyclyl ring;

R³ is selected from the group consisting of halo, CN, $C_{1-3}$ alkyl, $C_{1-3}$ alkoxy, $C_{1-3}$haloalkyl, $C_{1-3}$haloalkoxy and $C_{3-6}$ cycloalkyl; and R⁴ is selected from the group consisting of H, halo, CN, $C_{1-3}$alkyl, $C_{1-3}$ alkoxy, $C_{1-3}$haloalkyl, $C_{1-3}$haloalkoxy and $C_{3-6}$ cycloalkyl.

In one embodiment, R¹ is an N-linked 6-9 membered fused bicyclic heterocyclyl optionally substituted with one, two or three substituents independently selected from the group consisting of: oxo, halo, hydroxyl, $C_{1-3}$alkyl and $C_{1-3}$alkoxy.

In one embodiment, R¹ is an N-linked 6-9 membered fused bicyclic heterocyclyl selected from the group consisting of: hexahydropyrrolo[1,2-a]pyrazin-2(1H)-yl, hexahydropyrrolo[1,2-a]pyrazine-6(2H)-yl, 3-azabicyclo[3.1.0]hexanyl and hexahydro-2H-furo[2,3-c]pyrrolyl, which fused bicyclic heterocyclyl is optionally substituted with one, two or three substituents independently selected from the group consisting of: oxo, halo, hydroxyl, $C_{1-3}$alkyl and $C_{1-3}$alkoxy.

In one embodiment, R¹ is an N-linked 6-9 membered fused bicyclic heterocyclyl selected from the group consisting of: hexahydropyrrolo[1,2-a]pyrazin-2(1H)-yl, hexahydropyrrolo[1,2-a]pyrazin-6(2H)-yl, 3-azabicyclo[3.1.0]hexanyl, hexahydro-2H-furo[2,3-c]pyrrolyl and octahydropyrazino[2,1-c][1,4]oxazinyl, which fused bicyclic heterocyclyl is optionally substituted with one, two or three substituents independently selected from the group consisting of: oxo and hydroxyl.

In one embodiment, R¹ is an N-linked 6-9 membered fused bicyclic heterocyclyl selected from the group consisting of: hexahydropyrrolo[1,2-a]pyrazin-2(1H)-yl, hexahydropyrrolo[1,2-a]pyrazin-2(2H)-yl, 3-azabicyclo[3.1.0]hexane-3-yl, hexahydro-2H-furo[2,3-c]pyrrole-5-yl and octahydropyrazino[2,1-c][1,4]oxazine-8-yl, which fused bicyclic heterocyclyl is optionally substituted with one, two or three substituents independently selected from the group consisting of: oxo and hydroxyl.

In one embodiment, R¹ is an N-linked 6-9 membered fused bicyclic heterocyclyl selected from the group consisting of: hexahydropyrrolo[1,2-a]pyrazin-2(1H)-yl, hexahydropyrrolo[1,2-a]pyrazin-6(2H)-one, 3-azabicyclo[3.1.0]hexan-1-ol, hexahydro-2H-furo[2,3-c]pyrrolyl and octahydropyrazino[2,1-c][1,4]oxazinyl.

In one embodiment, R¹ is an N-linked 7-10 membered heterospirane ring, which heterospirane ring is optionally substituted with one, two or three substituents independently selected from the group consisting of: oxo, halo, hydroxyl, $C_{1-3}$ alkoxyl and $C_{1-3}$alkyl, wherein said $C_{1-3}$ alkoxyl and $C_{1-3}$alkyl is optionally substituted with one or two substituents independently selected from the group consisting of halo and hydroxyl, and with the proviso that $R^1$ is not 2-oxa-6-azaspiro[3.4]octan-6-yl;

$R^1$ is an N-linked 7-10 membered heterospirane ring, which heterospirane ring is optionally substituted with one substituent selected from the group consisting of: oxo, halo, hydroxyl, $C_{1-3}$ alkoxyl and $C_{1-3}$alkyl, and with the proviso that $R^1$ is not 2-oxa-6-azaspiro[3.4]octan-6-yl.

In one embodiment, $R^1$ is an N-linked 7-10 membered heterospirane ring selected from the group consisting of: oxazasprio[2.5]octanyl, dioxazaspiro[2.6]nonanyl, dioxazaspiro[3.5]nonanyl, dioxazaspiro[4.4]nonanyl, diazaspiro[2.7]decanyl, diazasprio[3.6]decanyl, diazasprio[4.5]decanyl, oxaadiazaspiro[2.7]decanyl, oxadiazasprio[3.6]decanyl and oxadiazasprio[4.5]decanyl, which heterospirane ring is optionally substituted with one substituent selected from the group consisting of: oxo, halo, hydroxyl, $C_{1-3}$ alkoxyl and $C_{1-3}$alkyl.

In one embodiment, $R^1$ is an N-linked 7-10 membered heterospirane ring selected from the group consisting of: oxazasprio[2.5]octanyl, dioxazaspiro[2.6]nonanyl, dioxazaspiro[3.5]nonanyl, dioxazaspiro[4.4]nonanyl, diazaspiro[2.7]decanyl, diazasprio[3.6]decanyl, diazasprio[4.5]decanyl, oxaadiazaspiro[2.7]decanyl, oxadiazasprio[3.6]decanyl and oxadiazasprio[4.5]decanyl, which heterospirane ring is optionally substituted with one oxo group.

In one embodiment, $R^1$ is an N-linked 7-10 membered heterospirane ring selected from the group consisting of: 1-oxa-4,8-diazaspiro[4.5]decan-8-yl, 3-oxa-1,8-diazaspiro[4.5]decan-8-yl, 1,8-diazaspiro[4.5]decan-8-yl, 2,8-diazaspiro[4.5]decan-8-yl, 2,5-dioxa-8-azaspiro[3.5]nonan-8-yl and 4-oxa-7-azaspiro[2.5]octan-7-yl, which heterospirane ring is optionally substituted with one oxo group.

In one embodiment, $R^1$ is 3-oxo-1-oxa-4,8-diazaspiro[4.5]decan-8-yl, 2-oxo-3-oxa-1,8-diazaspiro[4.5]decan-8-yl, 2-oxo-1,8-diazaspiro[4.5]decan-8-yl, 1-oxo-2,8-diazaspiro[4.5]decan-8-yl, 2,5-dioxa-8-azaspiro[3.5]nonan-8-yl and 4-oxa-7-azaspiro[2.5]octan-7-yl.

In one embodiment, $R^2$ is selected from the group consisting of:
a) 5-6 membered heterocyclyl ring optionally substituted with one, two or three substituents independently selected from the group consisting of:
$C_{1-3}$alkyl, which alkyl group is optionally substituted with one halo, hydroxyl or $C_{1-3}$alkoxy group,
halo,
hydroxyl,
—$SO_2CH_3$,
—$COCH_3$, and
—$COCH_2OH$,
wherein when the 5-6 membered heterocyclyl ring contains a substitutable nitrogen atom, the group of substituents also includes an oxygen containing 4-6 membered heterocyclyl ring with the proviso that the oxygen containing heterocyclyl ring is attached to said substitutable nitrogen atom;
b) —O-4-6 membered heterocyclyl ring wherein the heterocyclyl ring is optionally substituted with one or two $C_{1-3}$alkyl groups which may be the same or different;
c) $C_{3-6}$ cycloalkyl optionally substituted with one or two substituents independently selected from the group consisting of hydroxyl and $C_{1-3}$alkyl;
d) —O—$C_{3-6}$ cycloalkyl wherein the cycloalkyl group is optionally substituted with one or two substituents independently selected from the group consisting of hydroxyl and $C_{1-3}$alkyl; and
e) $C_{1-6}$alkoxy.

In one embodiment, $R^2$ is selected from the group consisting of:
a) 5-6 membered heterocyclyl ring optionally substituted with one, two or three substituents independently selected from the group consisting of: $C_{1-3}$alkyl, which alkyl group is optionally substituted with one substituent selected from the group consisting of halo, hydroxyl and $C_{1-3}$alkoxy,
halo,
hydroxyl,
—$SO_2CH_3$,
—$COCH_3$, and
—$COCH_2OH$,
wherein when the 5-6 membered heterocyclyl ring contains a substitutable nitrogen atom, the group of substituents also includes an oxygen containing 4-6 membered heterocyclyl ring with the proviso that the oxygen containing heterocyclyl ring is attached to said substitutable nitrogen atom;
b) —O-4-6 membered heterocyclyl ring wherein the heterocyclyl ring is optionally substituted with one or two $C_{1-3}$alkyl groups which may be the same or different; and
c) $C_{3-6}$ cycloalkyl optionally substituted with one or two substituents independently selected from the group consisting of hydroxyl and $C_{1-3}$alkyl.

In one embodiment, $R^2$ is a 4-7 membered heterocyclyl ring optionally substituted with one, two or three substituents independently selected from the group consisting of:
$C_{1-3}$alkyl, which alkyl group is optionally substituted with one, two or three substituents independently selected from the group consisting of: halo, hydroxyl, $CO_2H$, —$CH_2CH_2$— and $C_{1-3}$alkoxy,
cyano,
halo,
hydroxyl,
—$SO_2CH_3$,
—$COCH_3$, and
—$COCH_2OH$,
wherein when the 4-7 membered heterocyclyl ring contains a substitutable nitrogen atom, the group of substituents also includes a 4-6 membered heterocyclyl ring which 4-6 membered heterocyclyl ring is optionally substituted with one or two substituents independently selected from the group consisting of: cyano, halo, hydroxyl, $C_{1-3}$alkyl, $C_{1-3}$alkoxyl and $CH_2OH$, with the proviso that the 4-6 membered heterocyclyl ring is attached to said substitutable nitrogen atom.

In one embodiment, $R^2$ is a 5-6 membered heterocyclyl ring optionally substituted with one, two or three substituents independently selected from the group consisting of:
$C_{1-3}$alkyl, which alkyl group is optionally substituted with one halo, hydroxyl or $C_{1-3}$alkoxy group,
halo,
hydroxyl,
—$SO_2CH_3$,
—$COCH_3$, and
—$COCH_2OH$,
wherein when the 5-6 membered heterocyclyl ring contains a substitutable nitrogen atom, the group of substituents also includes an oxygen containing 4-6 membered heterocyclyl ring with the proviso that the oxygen containing heterocyclyl ring is attached to said substitutable nitrogen atom.

In one embodiment, $R^2$ is a 5-6 membered heterocyclyl ring optionally substituted with one, two or three substituents independently selected from the group consisting of:
$C_{1-3}$alkyl, which alkyl group is optionally substituted with one substituent selected from the group consisting of halo, hydroxyl and $C_{1-3}$alkoxy,
halo,
hydroxyl, and
—$COCH_2OH$,
wherein when the 5-6 membered heterocyclyl ring contains a substitutable nitrogen atom, the group of substituents also includes an oxygen containing 4-6 membered heterocyclyl ring with the proviso that the oxygen containing heterocyclyl ring is attached to said substitutable nitrogen atom.

In one embodiment, $R^2$ is a 5-6 membered heterocyclyl ring optionally substituted with one, two or three substituents independently selected from the group consisting of:
halo,
wherein when the 5-6 membered heterocyclyl ring contains a substitutable nitrogen atom, the group of substituents also includes an oxygen containing 4-6 membered heterocyclyl ring with the proviso that the oxygen containing heterocyclyl ring is attached to said substitutable nitrogen atom.

In one embodiment, $R^2$ is a 5-6 membered heterocyclyl ring selected from the group consisting of: piperazinyl, piperidinyl, pyrrolidinyl, tetrahydropyridinyl, tetrahydropyranyl, tetrahydrofuranyl and morpholinyl, which heterocyclyl ring is optionally substituted with one, two or three substituents independently selected from the group consisting of:
halo,
wherein when the 5-6 membered heterocyclyl ring contains a substitutable nitrogen atom, the group of substituents also includes an oxygen containing 4-6 membered heterocyclyl ring with the proviso that the oxygen containing heterocyclyl ring is attached to said substitutable nitrogen atom.

In one embodiment, $R^2$ is piperidinyl or pyrrolidinyl ring, which ring is optionally substituted with one, two or three substituents independently selected from the group consisting of:
$C_{1-3}$alkyl, which alkyl group is optionally substituted with one substituent selected from the group consisting of halo, hydroxyl and $C_{1-3}$alkoxy,
halo,
hydroxyl,
—$COCH_2OH$, and
an oxygen containing 4-6 membered heterocyclyl ring with the proviso that the oxygen containing heterocyclyl ring is attached to the nitrogen of the piperidinyl or pyrrolidinyl ring.

In one embodiment, $R^2$ is a piperidinyl ring optionally substituted with one, two or three substituents independently selected from the group consisting of:
an oxygen containing 4-6 membered heterocyclyl ring with the proviso that the oxygen containing heterocyclyl ring is attached to the nitrogen atom of the piperidinyl ring;
$C_{1-3}$alkyl, which alkyl group is optionally substituted with one substituent selected from the group consisting of halo, hydroxyl and $C_{1-3}$alkoxy;
halo;
hydroxyl, and
$COCH_2OH$.

In one embodiment, $R^2$ is a piperidinyl or pyrrolidinyl ring, which ring is optionally substituted with one, two or three substituents independently selected from the group consisting of:
halo, and
an oxygen containing 4-6 membered heterocyclyl ring with the proviso that the oxygen containing heterocyclyl ring is attached to the nitrogen atom or the piperidinyl or pyrrolidinyl ring.

In one embodiment, $R^2$ is a piperidinyl ring optionally substituted with one, two or three substituents independently selected from the group consisting of:
halo, and
an oxygen containing 4-6 membered heterocyclyl ring with the proviso that the oxygen containing heterocyclyl ring is attached to the nitrogen atom of the piperidinyl ring.

In one embodiment, $R^2$ is a pyrrolidinyl ring optionally substituted with one, two or three substituents independently selected from the group consisting of $C_{1-3}$alkyl and hydroxyl.

In one embodiment, $R^2$ is 1-(oxetan-3-yl)piperidin-4-yl or 1-(oxetan-3-yl)-3-fluoro-piperidin-4-yl.

In one embodiment, $R^2$ is 1-(oxetan-3-yl)piperidin-4-yl.

In one embodiment, $R^2$ is tetrahydropyran-4-yl.

In one embodiment, $R^2$ is $C_{3-6}$ cycloalkyl optionally substituted with one or two substituents independently selected from the group consisting of cyano, halo, hydroxyl, $C_{1-3}$alkyl, $C_{1-3}$alkoxyl, $CO_2H$ and a 4-6 membered heterocyclyl ring; In one embodiment, $R^2$ is $C_{3-6}$ cycloalkyl optionally substituted with one or two substituents independently selected from the group consisting of cyano, halo, hydroxyl, $C_{1-3}$alkyl, $C_{1-3}$alkoxyl and $CO_2H$.

In one embodiment, $R^2$ is $C_{3-6}$ cycloalkyl optionally substituted with one or two substituents independently selected from the group consisting of hydroxyl and $C_{1-3}$alkyl.

In one embodiment, $R^2$ is cyclohexyl optionally substituted with one or two substituents independently selected from the group consisting of hydroxyl and $C_{1-3}$alkyl.

In one embodiment, $R^2$ is O-4-6 membered heterocyclyl ring wherein the heterocyclyl ring is optionally substituted with one or two substituents independently selected from the group consisting of: cyano, hydroxyl, $C_{1-3}$alkyl, $C_{1-3}$alkoxyl, $CH_2OH$ and —$CO_2H$.

In one embodiment, $R^2$ is O-tetrahydrofuran wherein the tetrahydrofuran ring is optionally substituted with one or two substituents independently selected from the group consisting of: cyano, hydroxyl, $C_{1-3}$alkyl, $C_{1-3}$alkoxyl, $CH_2OH$ and —$CO_2H$.

In one embodiment, $R^3$ is selected from the group consisting of CN, $C_{1-3}$ alkyl, $C_{1-3}$ alkoxy, $C_{1-3}$haloalkyl, and $C_3$ cycloalkyl. In one embodiment, $R^3$ is selected from the group consisting of $C_{1-3}$ alkyl and $C_{1-3}$ alkoxyl. In one embodiment, $R^3$ is selected from the group consisting of methyl and methoxy.

In one embodiment, $R^4$ is selected from the group consisting of H, halo, CN, $C_{1-3}$alkyl and $C_{1-3}$haloalkyl. In one embodiment, $R^4$ is selected from the group consisting of H, halo and $C_{1-3}$alkyl. In one embodiment, $R^4$ is selected from the group consisting of H, halo and methyl. In one embodiment, $R^4$ is selected from the group consisting of H, fluoro, chloro and methyl. In one embodiment, $R^4$ is selected from the group consisting of H, chloro and methyl. In one embodiment, $R^4$ is selected from the group consisting of chloro and methyl. In one particular embodiment, $R^4$ is methyl.

In one embodiment, the invention provides a compound of Formula (I) or a salt thereof wherein $R^1$, $R^3$ and $R^4$ are as defined above, and $R^2$ is a 5-6 membered heterocyclyl ring optionally substituted with one, two or three substituents independently selected from the group consisting of:
$C_{1-3}$alkyl, which alkyl group is optionally substituted with one halo, hydroxyl or $C_{1-3}$ alkoxy group,
halo,
hydroxyl,
—$SO_2CH_3$,
—$COCH_3$, and
—$COCH_2OH$,
wherein when the 5-6 membered heterocyclyl ring contains a substitutable nitrogen atom, the group of substituents also includes an oxygen containing 4-6 membered heterocyclyl ring with the proviso that the oxygen containing heterocyclyl ring is attached to said substitutable nitrogen atom.

In this embodiment, $R^1$, $R^3$ and $R^4$ may be further defined as in any of the preceding embodiments. For example, $R^3$ may be selected from the group consisting of methyl and methoxy and/or $R^4$ may be selected from the group consisting of chloro and methyl.

In one embodiment, the invention provides a compound of Formula (I) or a salt thereof wherein $R^1$, $R^3$ and $R^4$ are as defined above and $R^2$ is a 5-6 membered heterocyclyl ring optionally substituted with one, two or three substituents independently selected from the group consisting of:
$C_{1-3}$alkyl, which alkyl group is optionally substituted with one substituent selected from the group consisting of halo, hydroxyl and $C_{1-3}$alkoxy,
halo,
hydroxyl, and
—$COCH_2OH$,
wherein when the 5-6 membered heterocyclyl ring contains a substitutable nitrogen atom, the group of substituents also contains an oxygen containing 4-6 membered heterocyclyl ring with the proviso that the oxygen containing heterocyclyl ring is attached to said substitutable nitrogen atom.

In this embodiment, $R^1$, $R^3$ and $R^4$ may be further defined as in any of the preceding embodiments. For example, $R^3$ may be selected from the group consisting of methyl and methoxy and/or $R^4$ may be selected from the group consisting of chloro and methyl.

In one embodiment, the invention provides a compound of Formula (I) or a salt thereof wherein $R^1$, $R^3$ and $R^4$ are as defined above and $R^2$ is $C_{3-6}$ cycloalkyl optionally substituted with one or two substituents independently selected from the group consisting of cyano, halo, hydroxyl, $C_{1-3}$alkyl, $C_{1-3}$alkoxyl and $CO_2H$. In this embodiment, $R^1$, $R^3$ and $R^4$ may be further defined as in any of the preceding embodiments. For example, $R^3$ may be selected from the group consisting of methyl and methoxy and/or $R^4$ may be selected from the group consisting of chloro and methyl.

In one embodiment, the invention provides a compound of Formula (I) or a salt thereof wherein $R^1$, $R^3$ and $R^4$ are as defined above and $R^2$ is O-4-6 membered heterocyclyl ring wherein the heterocyclyl ring is optionally substituted from one or two substituents independently selected from the group consisting of: cyano, hydroxyl, $C_{1-3}$alkyl, $C_{1-3}$alkoxyl, $CH_2OH$ and —$CO_2H$. In this embodiment, $R^1$, $R^3$ and $R^4$ may be further defined as in any of the preceding embodiments. For example, $R^3$ may be selected from the group consisting of methyl and methoxy and/or $R^4$ may be selected from the group consisting of chloro and methyl.

In one embodiment, the compound of formula (I) or a pharmaceutically acceptable salt thereof is a compound of any one of Examples A-1 to A-13 or a pharmaceutically acceptable salt thereof. In one embodiment, the compound of formula (I) is a compound of any one of Examples A-1 to A-13.

In one embodiment, the compound of formula (I) or a pharmaceutically acceptable salt thereof is a compound of any one of Examples B-1 to B-10 or a pharmaceutically acceptable salt thereof. In one embodiment, the compound of formula (I) is a compound of any one of Examples B-1 to B-10.

In addition to the free base form or free acid form of the compounds described herein, the salt form of the compounds is also within the scope of the present invention. The salts or pharmaceutically-acceptable salts of the compounds described herein may be prepared in situ during the final isolation and purification of the compound, or by separately reacting the purified compound in its free acid form or free base form with a suitable base or acid, respectively. For reviews on suitable pharmaceutical salts see Berge et al, J. Pharm, Sci., 66, 1-19, 1977; P L Gould, International Journal of Pharmaceutics, 33 (1986), 201-217; and Bighley et al, Encyclopedia of Pharmaceutical Technology, Marcel Dekker Inc, New York 1996, Volume 13, page 453-497.

Certain compounds of formula (I) contain a basic group and are therefore capable of forming pharmaceutically-acceptable acid addition salts by treatment with a suitable acid. Suitable acids include pharmaceutically-acceptable inorganic acids and pharmaceutically-acceptable organic acids. Exemplary pharmaceutically-acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicylate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), and napthalene-2-sulfonate. In some embodiments, the pharmaceutically acceptable salts include the L-tartrate, ethanedisulfonate (edisylate), sulfate, phosphate, p-toluenesulfonate (tosylate), hydrochloride salt, methanesulfonate, citrate, fumarate, benzenesulfonate, maleate, hydrobromate, L-lactate, malonate, and S-camphor-10-sulfonate. In certain embodiments, some of these salts form solvates. In certain embodiments, some of these salts are crystalline.

Certain compounds of formula (I) contain an acidic group and are there for capable of forming pharmaceutically-acceptable base addition salts by treatment with a suitable base. Exemplary pharmaceutically acceptable base addition salts include, but are not limited to, aluminium, 2-amino-2-(hydroxymethyl)-1,3-propanediol (TRIS, tromethamine), arginine, benethamine (N-benzylphenethylamine), benzathine (N,N'-dibenzylethylenediamine), bis-(2-hydroxyethyl) amine, bismuth, calcium, chloroprocaine, choline, clemizole (1-p chlorobenzyl-2-pyrrolildine-1'-ylmethylbenzimidazole), cyclohexylamine, dibenzylethylenediamine, diethylamine, diethyltriamine, dimethylamine, dimethylethanolamine, dopamine, ethanolamine, ethylenediamine, L-histidine, iron, isoquinoline, lepidine, lithium, lysine, magnesium, meglumine (N-methylglucamine), piperazine, piperidine, potassium, procaine, quinine, quinoline, sodium, strontium, t-butylamine, and zinc.

Certain compounds of Formula (I) or salts thereof may exist in stereoisomeric forms (e.g., they may contain one or more asymmetric carbon atoms). The individual stereoisomers (enantiomers and diastereomers) and mixtures of these are included within the scope of the present invention. The different isomeric forms may be separated or resolved one from the other by conventional methods, or any given isomer may be obtained by conventional synthetic methods or by stereospecific or asymmetric syntheses.

Certain compounds of Formula (I) are capable of existing in tautomeric forms. For example, certain compounds exhibit keto-enol tautomerism. In some cases, only one of a pair of tautomeric forms fall within Formula (I). Such alternative tautomers also form part of the invention.

The invention also includes isotopically-labelled compounds and salts, which are identical to compounds of Formula (I) or salts thereof, but for the fact that one or more atoms are replaced by an atom having an atomic mass or mass number different from the atomic mass or mass number most commonly found in nature. Examples of isotopes that can be incorporated into compounds of Formula (I) or salts thereof isotopes of hydrogen, carbon, nitrogen, fluorine, such as $^3$H, $^{11}$C, $^{14}$C and $^{18}$F. Such isotopically-labelled compound of Formula (I) or salts thereof are useful in drug and/or substrate tissue distribution assays. For example, $^{11}$C and $^{18}$F isotopes are useful in PET (positron emission tomography). PET is useful in brain imaging. Isotopically-labelled compounds of Formula (I) and salts thereof can generally be prepared by carrying out the procedures disclosed below, by substituting a readily available isotopically-labelled reagent for a non-isotopically labelled reagent. In one embodiment, compounds of Formula (I) or salts thereof are not isotopically labelled.

Certain compounds of Formula (I) or salts thereof may exist in solid or liquid form. In the solid state, compounds of Formula (I) or salts may exist in crystalline or noncrystalline form, or as a mixture thereof. For compounds of Formula (I) or salts that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water.

The skilled artisan will further appreciate that certain compounds of Formula (I), pharmaceutically acceptable salts or solvates thereof that exist in crystalline form, including the various solvates thereof, may exhibit polymorphism (i.e. the capacity to occur in different crystalline structures). These different crystalline forms are typically known as "polymorphs." Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The skilled artisan also appreciates that this invention may contain various deuterated forms of compounds of Formula (I), or pharmaceutically acceptable salts thereof. Each available hydrogen atom attached to a carbon atom may be independently replaced with a deuterium atom. A person of ordinary skill in the art will know how to synthesize deuterated forms of compounds of Formula (I), or pharmaceutically acceptable salts thereof. Commercially available deuterated starting materials may be employed in the preparation of deuterated forms of compounds of Formula (I) or pharmaceutically acceptable salts thereof, or they may be synthesized using conventional techniques employing deuterated reagents (e.g. lithium aluminum deuteride).

C. Methods of Use

Compounds of Formula (I) or pharmaceutically acceptable salts thereof are inhibitors of LRRK2 kinase activity and are thus believed to be of potential use in the treatment of or prevention of the following neurological diseases: Parkinson's disease, Alzheimer's disease, dementia (including Lewy body dementia and vascular dementia, HIV-induced dementia), amyotrophic lateral sclerosis (ALS), age related memory dysfunction, mild cognitive impairment, argyrophilic grain disease, Pick's disease, corticobasal degeneration, progressive supranuclear palsy, inherited frontotemporal dementia and parkinsonism linked to chromosome 17 (FTDP-17), withdrawal symptoms/relapse associated with drug addiction, L-Dopa induced dyskinesia, ischemic stroke, traumatic brain injury, spinal cord injury and multiple sclerosis. Other diseases potentially treatable by inhibition of LRRK2 include, but are not limited to, lysosomal disorders (for example, Niemann-Pick Type C disease, Gaucher disease), Crohn's disease, cancers (including thyroid, renal (including papillary renal), breast, lung and prostate cancers, leukemias (including acute myelogenous leukemia (AML)) and lymphomas), rheumatoid arthritis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, obesity, epilepsy, pulmonary diseases such as chronic obstructive pulmonary disease, idiopathic pulmonary fibrosis, Sjogren's syndrome, Devic's disease, inflammatory myopathies, ankylosing spondylitis, bacterial infections (including leprosy), viral infections (including tuberculosis, HIV, West Nile virus and chikungunya virus) and parasitic infections.

One aspect of the invention provides a compound of Formula (I) or a pharmaceutically acceptable salt thereof for use in therapy. In one embodiment, the invention provides a compound of Formula (I) or a pharmaceutically acceptable salt thereof for use in the treatment of or prevention of the above disorders (i.e. the neurological diseases and other diseases listed above). In one embodiment, the invention provides a compound of Formula (I) or a pharmaceutically acceptable salt thereof for use in the treatment of or prevention of Parkinson's disease. In one embodiment, the invention provides a compound of Formula (I) or a pharmaceutically acceptable salt thereof for use in the treatment of Parkinson's disease. In another embodiment, the invention provides a compound of Formula (I) or a pharmaceutically acceptable salt thereof for use in the treatment of or prevention of Alzheimer's disease. In one embodiment, the invention provides a compound of Formula (I) or a pharmaceutically acceptable salt thereof for use in the treatment of Alzheimer's disease. In another embodiment, the invention provides a compound of Formula (I) or a pharmaceutically acceptable salt thereof for use in the treatment of tuberculosis.

A further aspect of the invention provides the use of a compound of Formula (I) or a pharmaceutically acceptable salt thereof in the manufacture of a medicament for the treatment of or prevention of the above disorders (i.e. the neurological diseases and other diseases listed above). A further aspect of the invention provides the use of a compound of Formula (I) or a pharmaceutically acceptable salt thereof in the manufacture of a medicament for the treatment of or prevention of Parkinson's disease. A further aspect of the invention provides the use of a compound of Formula (I) or a pharmaceutically acceptable salt thereof in the manufacture of a medicament for the treatment of Parkinson's disease. In another embodiment, the invention provides the use of a compound of Formula (I) or a pharmaceutically acceptable salt thereof in the manufacture of a medicament for the treatment of treatment of or prevention of Alzheimer's disease. In one embodiment, the invention provides the use of a compound of Formula (I) or a pharmaceutically acceptable salt thereof in the manufacture of a medicament for the treatment of Alzheimer's disease. In another embodiment, the invention provides use of a compound of Formula (I) or a pharmaceutically acceptable salt thereof in the manufacture of a medicament for the treatment of tuberculosis.

A further aspect of the invention provides a method of treatment or prevention of a disorder listed above (i.e. selected from the neurological diseases and other diseases listed above), which comprises administering to a subject in need thereof a therapeutically effective amount of a compound of Formula (I) or a pharmaceutically acceptable salt thereof. A further aspect of the invention provides a method of treatment or prevention of Parkinson's disease, which comprises administering to a subject in need thereof a therapeutically effective amount of a compound of Formula (I) or a pharmaceutically acceptable salt thereof. A further aspect of the invention provides a method of treatment of Parkinson's disease, which comprises administering to a subject in need thereof a therapeutically effective amount of a compound of Formula (I) or a pharmaceutically acceptable salt thereof. A further aspect of the invention provides a method of treatment or prevention of Alzheimer's disease, which comprises administering to a subject in need thereof a therapeutically effective amount of a compound of Formula (I) or a pharmaceutically acceptable salt thereof. A further aspect of the invention provides a method of treatment of Alzheimer's disease, which comprises administering to a subject in need thereof a therapeutically effective amount of a compound of Formula (I) or a pharmaceutically acceptable salt thereof. A further aspect of the invention provides a method of treatment of tuberculosis, which comprises administering to a subject in need thereof a therapeutically effective amount of a compound of Formula (I) or a pharmaceutically acceptable salt thereof. In an embodiment, the subject is human.

In the context of the present invention, treatment of Parkinson's disease refers to the treatment of sporadic Parkinson's disease, and/or familial Parkinson's disease. In one embodiment, treatment of Parkinson's disease refers to treatment of familial Parkinson's disease. Familial Parkinson's disease patients are those expressing one or more of the following LRRK2 kinase mutations: G2019S mutation, N1437H mutation, R1441G mutation, R1441C mutation, R1441H mutation, Y1699C mutation, S1761R mutation, or I2020T mutation. In another embodiment, familial Parkinson's disease patients express other coding mutations (such as G2385R) or non-coding single nucleotide polymorphisms at the LRRK2 locus that are associated with Parkinson's disease In a more particular embodiment, familial Parkinson's disease includes patients expressing the G2019S mutation or the R1441G mutation in LRRK2 kinase. In one embodiment, treatment of Parkinson's disease refers to the treatment of familial Parkinson's disease includes patients expressing LRRK2 kinase bearing G2019S mutation. In another embodiment, familial Parkinson's disease patients express aberrantly high levels of normal LRRK2 kinase.

In the context of the present invention, treatment of Parkinson's disease refers to the treatment of sporadic Parkinson's disease, and/or familial Parkinson's disease. In one embodiment, treatment of Parkinson's disease refers to treatment of familial Parkinson's disease. Familial Parkinson's disease patients are those expressing one or more of the following LRRK2 kinase mutations: G2019S mutation, N1437H mutation, R1441G mutation, R1441C mutation, R1441H mutation, Y1699C mutation, S1761R mutation, or I2020T mutation. In another embodiment, familial Parkinson's disease patients express other coding mutations (such as G2385R) or non-coding single nucleotide polymorphisms at the LRRK2 locus that are associated with Parkinson's disease In a more particular embodiment, familial Parkinson's disease includes patients expressing the G2019S mutation or the R1441G mutation in LRRK2 kinase. In one embodiment, treatment of Parkinson's disease refers to the treatment of familial Parkinson's disease includes patients expressing LRRK2 kinase bearing G2019S mutation. In another embodiment, familial Parkinson's disease patients express aberrantly high levels of normal LRRK2 kinase.

In one embodiment, the invention provides a method of treatment of Parkinson's disease, which comprises administering to a human expressing the G2019S mutation in LRRK2 kinase in need thereof a therapeutically effective amount of a compound of Formula (I) or a pharmaceutically acceptable salt thereof.

In one embodiment, the invention provides a method of treatment of Parkinson's disease, which comprises testing in a human for the G2019S mutation in LRRK2 kinase and administering to the human expressing the G2019S mutation in LRRK2 kinase in need thereof a therapeutically effective amount of a compound of Formula (I) or a pharmaceutically acceptable salt thereof.

Treatment of Parkinson's disease may be symptomatic or may be disease modifying. In one embodiment, treatment of Parkinson's disease refers to symptomatic treatment. In one embodiment, treatment of Parkinson's disease refers to disease modifying treatment.

Compounds of the present invention may also be useful in treating patients identified as susceptible to progression to severe Parkinsonism by means of one or more subtle features associated with disease progression such as family history, olfaction deficits, constipation, cognitive defects, gait or biological indicators of disease progression gained from molecular, biochemical, immunological or imaging technologies. In this context, treatment may be symptomatic or disease modifying.

In the context of the present invention, treatment of Alzheimer's disease refers to the treatment of sporadic Alzheimer's disease and/or familial Alzheimer's disease. Treatment of Alzheimer's disease may be symptomatic or may be disease modifying. In one embodiment, treatment of Alzheimer's disease refers to symptomatic treatment.

In the context of the present invention, treatment of dementia (including Lewy body dementia and vascular dementia, HIV-induced dementia), amyotrophic lateral sclerosis (ALS), age related memory dysfunction, mild cognitive impairment, argyrophilic grain disease, Pick's disease, corticobasal degeneration, progressive supranuclear palsy, inherited frontotemporal dementia and parkinsonism linked to chromosome 17 (FTDP-17), multiple sclerosis, lysosomal disorders (for example, Niemann-Pick Type C disease, Gaucher disease), Crohn's disease, cancers (including thyroid, renal (including papillary renal), breast, lung and prostate cancers, leukemias (including acute myelogenous leukemia (AML)) and lymphomas), rheumatoid arthritis, systemic lupus erythematosus, autoimmune hemolytic anemia, pure red cell aplasia, idiopathic thrombocytopenic purpura (ITP), Evans syndrome, vasculitis, bullous skin disorders, type 1 diabetes mellitus, obesity, epilepsy, pulmonary diseases such as chronic obstructive pulmonary disease, idiopathic pulmonary fibrosis, Sjogren's syndrome, Devic's disease, inflammatory myopathies, ankylosing spondylitis, may be symptomatic or disease modifying. In certain embodiments, treatment of these disorders refers to symptomatic treatment.

The invention also provides the use of inhibitors of LRRK2 in the production of neuronal progenitor cells in vitro for consequent therapeutic application in cell based-treatment of CNS disorders.

When a compound of Formula (I) or a pharmaceutically acceptable salt thereof is intended for use in the treatment of Parkinson's disease, it may be used in combination with medicaments alleged to be useful as symptomatic treatments of Parkinson's disease. Suitable examples of such other therapeutic agents include L-dopa, and dopamine agonists (e.g. pramipexole, ropinirole).

When a compound of Formula (I) or a pharmaceutically acceptable salt thereof is intended for use in the treatment of Alzheimer's disease, it may be used in combination with medicaments claimed to be useful as either disease modifying or symptomatic treatments of Alzheimer's disease. Suitable examples of such other therapeutic agents may be symptomatic agents, for example those known to modify cholinergic transmission such as M1 muscarinic receptor agonists or allosteric modulators, M2 muscarinic antagonists, acetylcholinesterase inhibitors (such as tetrahydroaminoacridine, donepezil hydrochloride rivastigmine, and galantamine), nicotinic receptor agonists or allosteric modulators (such as α7 agonists or allosteric modulators or α4β2 agonists or allosteric modulators), PPAR agonists (such as PPARγ agonists), 5-HT$_4$ receptor partial agonists, 5-HT$_6$ receptor antagonists e.g. SB-742457 or 5HT1A receptor antagonists and NMDA receptor antagonists or modulators, or disease modifying agents such as β or γ-secretase inhibitors e.g semagacestat, mitochondrial stabilizers, microtubule stabilizers or modulators of Tau pathology such as Tau aggregation inhibitors (e.g. methylene blue and REMBER™), NSAIDS, e.g. tarenflurbil, tramiprosil; or antibodies for example bapineuzumab or solanezumab; proteoglycans for example tramiprosate.

When a compound of Formula (I) or a pharmaceutically acceptable salt thereof is intended for use in the treatment of bacterial infections, parasitic infections or viral infections, it may be used in combination with medicaments alleged to be useful as symptomatic treatments that directly target the infectious agent.

When a compound of Formula (I) or a pharmaceutically acceptable salt thereof is used in combination with other therapeutic agents, the compound may be administered either sequentially or simultaneously by any convenient route.

The invention also provides, in a further aspect, a combination comprising a compound of Formula (I) or a pharmaceutically acceptable salt thereof together with one or more further therapeutic agent or agents.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention. The individual components of such combinations may be administered either sequentially or simultaneously in separate or combined pharmaceutical formulations.

When a compound of Formula (I) or a pharmaceutically acceptable salt thereof is used in combination with a second therapeutic agent active against the same disease state the dose of each compound may differ from that when the compound is used alone. Appropriate doses will be readily appreciated by those skilled in the art.

D. Composition

Compounds of Formula (I) or pharmaceutically acceptable salts thereof may be formulated into pharmaceutical compositions prior to administration to a subject. According to one aspect, the invention provides a pharmaceutical composition comprising a compound of Formula (I) or a pharmaceutically acceptable salt thereof and a pharmaceutically acceptable excipient. According to another aspect, the invention provides a process for the preparation of a pharmaceutical composition comprising admixing a compound of Formula (I) or a pharmaceutically acceptable salt thereof, with a pharmaceutically acceptable excipient.

Pharmaceutical compositions may be presented in unit dose forms containing a predetermined amount of active ingredient per unit dose. Such a unit may contain, for example, 0.1 mg, 0.5 mg, or 1 mg to 50 mg, 100 mg, 200 mg, 250 mg, 500 mg, 750 mg or 1 g of a compound of the present invention, depending on the disease being treated, the route of administration and the age, weight and condition of the subject, or pharmaceutical compositions may be presented in unit dose forms containing a predetermined amount of active ingredient per unit dose. In other embodiments, the unit dosage compositions are those containing a daily dose or sub-dose as described herein, or an appropriate fraction thereof, of an active ingredient. Furthermore, such pharmaceutical compositions may be prepared by any of the methods well-known to one skilled in the art.

A therapeutically effective amount of a compound of Formula (I) will depend upon a number of factors including, for example, the age and weight of the intended recipient, the precise condition requiring treatment and its severity, the nature of the formulation, and the route of administration, and will ultimately be at the discretion of the attendant prescribing the medication. However, a therapeutically effective amount of a compound of formula (I) for the treatment of diseases described in the present invention will generally be in the range of 0.1 to 100 mg/kg body weight of recipient per day and more usually in the range of 1 to 10 mg/kg body weight per day. Thus, for a 70 kg adult mammal, the actual amount per day would usually be from 70 to 700 mg and this amount may be given in a single dose per day or in a number of sub-doses per day as such as two, three, four, five or six doses per day. Or the dosing can be done intermittently, such as once every other day, once a week or once a month. A therapeutically effective amount of a pharmaceutically acceptable salt or solvate, etc., may be determined as a proportion of the therapeutically effective amount of the compound of Formula (I) per se. It is envisaged that similar dosages would be appropriate for treatment of the other diseases referred to above.

The pharmaceutical compositions of the invention may contain one or more compounds of Formula (I). In some embodiments, the pharmaceutical compositions may contain more than one compound of the invention. For example, in some embodiments, the pharmaceutical compositions may contain two or more compounds of Formula (I). In addition, the pharmaceutical compositions may optionally further comprise one or more additional pharmaceutically active compounds.

As used herein, "pharmaceutically acceptable excipient" means a pharmaceutically acceptable material, composition or vehicle involved in giving form or consistency to the pharmaceutical composition. Each excipient may be compatible with the other ingredients of the pharmaceutical composition when commingled such that interactions which would substantially reduce the efficacy of the compound of the invention when administered to a subject and interactions which would result in pharmaceutical compositions that are not pharmaceutically acceptable are avoided.

The compounds of the invention and the pharmaceutically-acceptable excipient or excipients may be formulated into a dosage form adapted for administration to the subject by the desired route of administration. For example, dosage forms include those adapted for (1) oral administration (including buccal or sublingual) such as tablets, capsules, caplets, pills, troches, powders, syrups, elixers, suspensions, solutions, emulsions, sachets, and cachets; (2) parenteral administration (including subcutaneous, intramuscular, intravenous or intradermal) such as sterile solutions, suspensions, and powders for reconstitution; (3) transdermal administration such as transdermal patches; (4) rectal administration such as suppositories; (5) nasal inhalation such as dry powders, aerosols, suspensions, and solutions; and (6) topical administration (including buccal, sublingual or transdermal) such as creams, ointments, lotions, solutions, pastes, sprays, foams, and gels. Such compositions may be prepared by any methods known in the art of pharmacy, for example by bringing into association a compound of Formula (I) with the carrier(s) or excipient(s). Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

Suitable pharmaceutically-acceptable excipients may vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically acceptable excipients may be chosen for their ability to facilitate carrying or transporting the compound or compounds of the invention once administered to the subject from an organ, or a portion of the body, to another organ, or a portion of the body. Certain pharmaceutically-acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a therapeutically effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

In certain embodiment, the present invention is directed to a pharmaceutical composition comprising 0.01 to 1000 mg of one or more of a compound of Formula (I) or a pharmaceutically acceptable salt thereof and 0.01 to 5 g of one or more pharmaceutically acceptable excipients.

In another embodiment, the present invention is directed a pharmaceutical composition for the treatment of neurodegeneration disease comprising a compound described herein or a pharmaceutically acceptable salt thereof and a pharmaceutically acceptable excipient. In another embodiment, the present invention is directed a pharmaceutical composition for the treatment of Parkinson's disease comprising a compound described herein or a pharmaceutically acceptable salt thereof and a pharmaceutically acceptable excipient.

E. Process of Preparing Compounds

The process to be utilized in the preparation of compounds of formula (I) described herein depends upon the desired compounds. Such factors as the selection of the specific substituent and various possible locations of the specific substituent all play a role in the path to be followed in the preparation of the specific compounds of this invention. Those factors are readily recognized by one of ordinary skill in the art.

In general, the compounds of the present invention may be prepared by standard techniques known in the art and by known processes analogous thereto. General methods for preparing compounds of formula (I) are set forth below. All starting material and reagents described in the below general experimental schemes are commercially available or can be prepared by methods known to one skilled in the art.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

General Scheme 1 provides exemplary processes of synthesis for preparing compounds of the present invention.

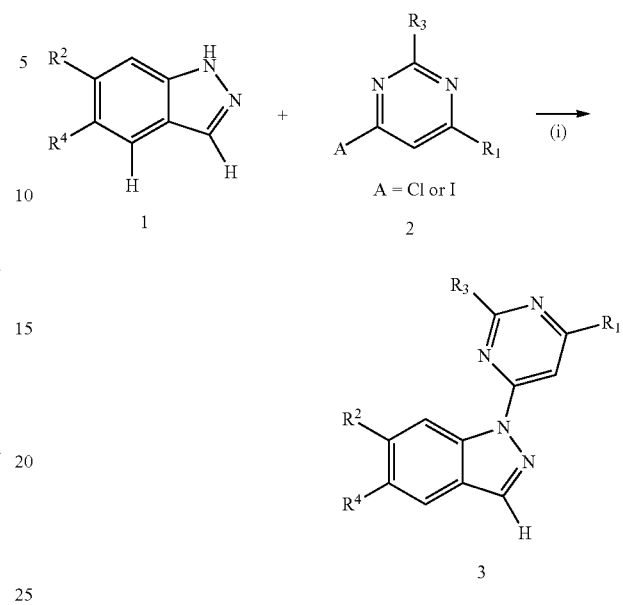

General Scheme 1 provides an exemplary synthesis for preparing compound 3 which represents compounds of Formula (I). In Scheme 1, $R_1$, $R_2$, $R_3$ and R4 are as defined in Formula I.

Step (i) may be a substitution reaction by reacting compound 1 with compound 2 using appropriate base such as $Cs_2CO_3$ in an appropriate solvent such as N, N-dimethylformamide (DMF) under suitable temperature such as about 100° C. to provide compound 3.

Step (i) may alternatively be a coupling reaction using appropriate reagents such as CuI and N,N'-dimethyl-cyclohexane-1,2-diamine in the presence of suitable base such as $K_3PO_4$ in a suitable solvent such as toluene at suitable temperature such as reflux condition to provide compound 3.

Step (i) may alternatively be a coupling reaction using appropriate reagents such as $Pd_2dba_3$ and di-tert-butyl(2',4',6'-triisopropyl-[1,1'-biphenyl]-2-yl)phosphine in the presence of suitable base such as sodium tert-butoxide in a suitable solvent such as toluene at suitable temperature such as 100° C. to provide compound 3.

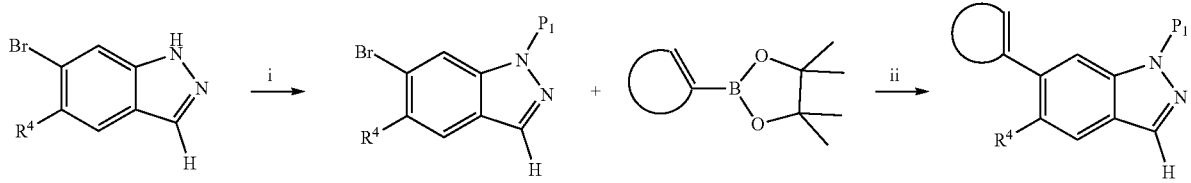

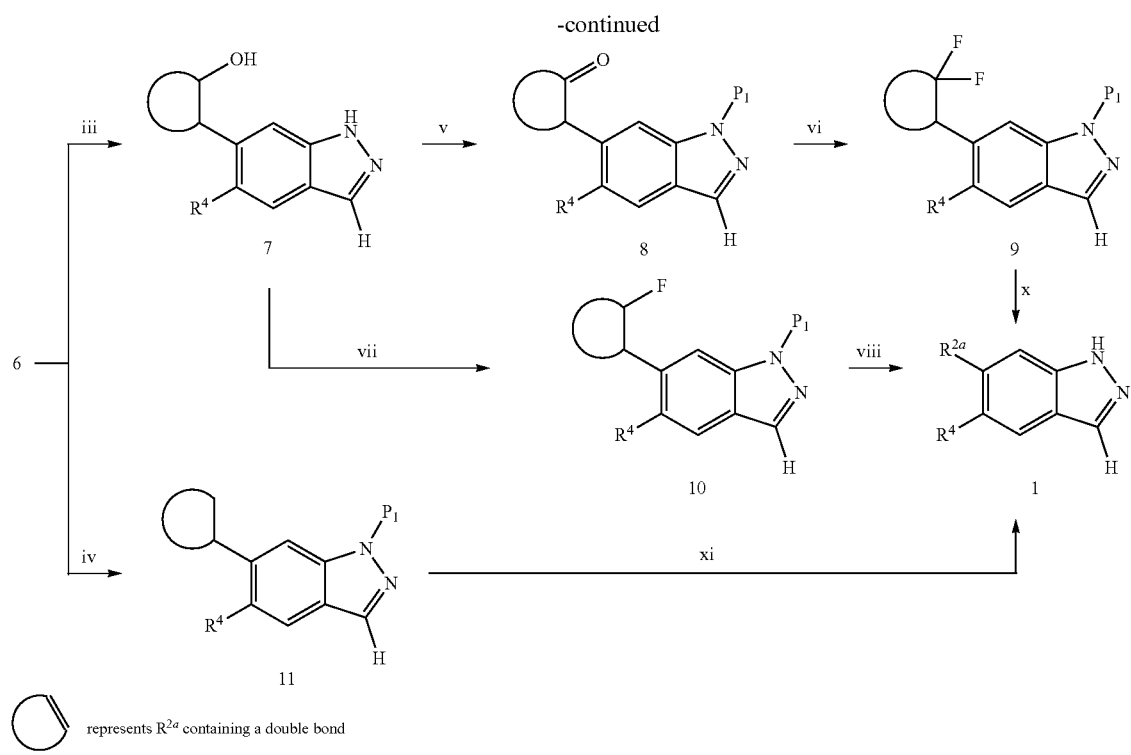

General Scheme 2 provides an exemplary synthesis for preparing intermediate 1 where $R^2$ is connected to the indazole ring though a carbon atom of $R^2$. $R^{2a}$ represents $R^2$ where this is connected to the indazole ring though a carbon atom of $R^2$. The protecting group, $P_1$, can be any suitable protecting groups for example, tetrahydro-2H-pyran-2-yl (THP), (trimethylsilyl)ethoxy)methyl (SEM) or Acetyl (Ac).

Intermediate 5 can be obtained in step (i) by reacting starting material 4 with suitable reagents such as DHP in the presence of suitable acids such as TsOH in appropriate solvents such as DCM under suitable temperatures such as 20° C. to 40° C.

Step (ii) is a cross-coupling reaction between intermediate 5 and boronic acid or esters using appropriate palladium catalysts such as Pd(dppf)Cl₂ in the presence of suitable bases such as $Na_2CO_3$ in appropriate solvents such as 1,4-dioxane at suitable temperatures such as 60° C. to 100° C.

Step (iii) involves reaction with suitable oxidation reagents such as $H_2O_2$ in a suitable solvent such as THF under suitable temperatures such as −60° C. to −10° C. to provide intermediate 7.

Step (iv) is a reaction with a suitable reducing reagent such as hydrogen in the presence of suitable catalysts such as Pd/C in polar solvents such as MeOH at appropriate temperatures such as 25° C. to 80° C.

Step (v) may be an oxidation reaction with oxidants such as DMP in suitable solvents such as DCM under suitable temperatures such as 0° C. to 25° C. to give intermediate 8.

Steps (vi) and (viii) involve reaction with a fluridizer such as DAST in suitable solvents such as DCM under suitable temperatures such as −78° C. to 0° C.

Steps (viii) (x) and (xi) are de-protection reactions. Typically, the intermediate is reacted with suitable acids such as HCl in suitable solvents such as 1,4-dioxane under suitable temperatures such as 25° C. to 40° C. to give intermediate 1.

General scheme 3

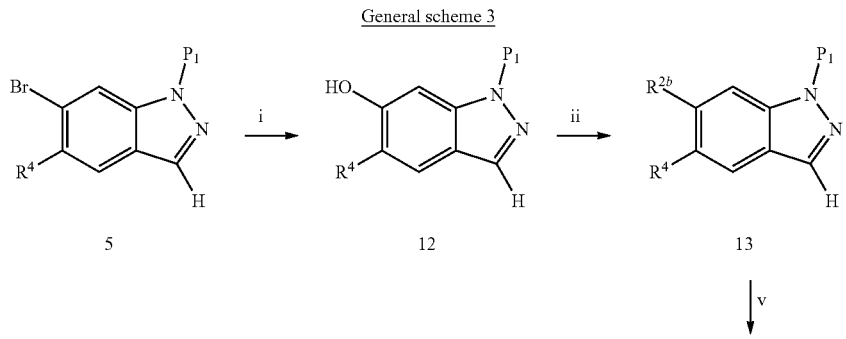

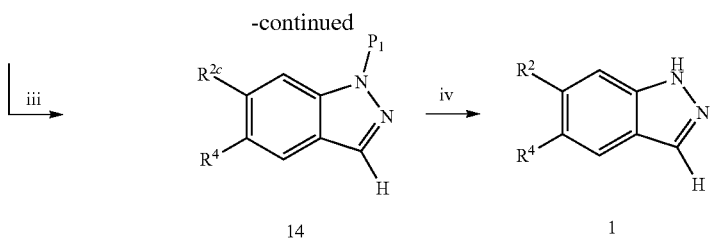

General Scheme 3 provides an exemplary synthesis for preparing intermediate 1. when $R^2$ connects to the indazole ring through an oxygen or nitrogen atom of $R^2$. $R^{2b}$ represents $R^2$ when $R^2$ connects to the indazole ring through an oxygen atom of $R^2$. $R^{2c}$ represents $R^2$ when $R^2$ connects to the indazole ring through the nitrogen atom of $R^2$. The protecting group, $P_1$, can be any suitable protecting group for example, tetrahydro-2H-pyran-2-yl (THP), (trimethylsilyl)ethoxy)methyl (SEM) or Acetyl (Ac).

Step (i) is a reaction with suitable reagents such as 4,4,4',4',5,5,5',5'-octamethyl-2,2'-bi(1,3,2-dioxaborolane) using appropriate catalysts such as $Pd(PPh_3)_4$ in the presence of appropriate bases such as KOAc in appropriate solvents such as DMF at a suitable temperatures such as 80° C. to 120° C., followed by reaction with suitable reagents such $H_2O_2$ in the presence of appropriate bases such as NaOH in suitable solvents such as THF at appropriate temperatures such as 25° C. to 80° C.

Step (ii) is a reaction with a suitable alkylating reagent such as 2-iodopropane in the presence of suitable bases such as $Cs_2CO_3$ in appropriate solvents such as $CH_3CN$ at a suitable temperatures such as 25° C. to 100° C.

Step (iii) can be a Buchwald coupling reaction with different amines such as 1-methylpiperazine using appropriate palladium catalysts such as $Pd_2(dba)_3$ in the presence of appropriate bases such as $Cs_2CO_3$ and appropriate ligands such as BINAP in appropriate solvents such as PhMe under suitable temperatures such as 80° C. to 130° C., or an Ullman coupling reaction with different amides such as 4-hydroxy-4-methylpiperidin-2-one using appropriate copper catalysts such as Cu(OAc)2 in the presence of appropriate bases such as LiHMDS and appropriate ligands such as DMEDA (or in absence of ligand) in appropriate solvents such as DCM under suitable temperatures such as 80° C. to 130° C.

Steps (iv) and (v) are deprotection reactions with suitable acids such HCl in suitable solvents such as 1,4-dioxane under suitable temperatures such as 25° C. to 40.

General scheme 4

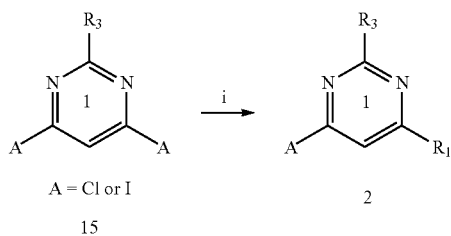

General Scheme 4 provides an exemplary synthesis for preparing intermediates 2. Step (i) can be a reaction with different amines using appropriate bases such as TEA in appropriate solvents such as EtOH under suitable temperatures such as 25° C. to 100° C. to provide intermediate 2.

EXAMPLES

General Experimental Procedures

The following descriptions and examples illustrate the invention. These examples are not intended to limit the scope of the present invention, but rather to provide guidance to the skilled chemist to prepare and use the compounds, compositions and methods of the present invention. While particular embodiments of the present invention are described, the skilled chemist will appreciate that various changes and modifications can be made without departing from the spirit and scope of the invention.

The chemical names of compounds described in the present application follows the principle of IUPAC nomenclature.

Heating of reaction mixtures with microwave irradiations was carried out on a Smith Creator (purchased from Personal Chemistry, Forboro/MA, now owned by Biotage), an Emrys Optimizer (purchased from Personal Chemistry) or an Explorer (provided by CEM Discover, Matthews/NC) microwave.

Conventional techniques may be used herein for work up of reactions and purification of the products of the Examples.

References in the Examples below relating to the drying of organic layers or phases may refer to drying the solution over magnesium sulfate or sodium sulfate and filtering off the drying agent in accordance with conventional techniques. Products may generally be obtained by removing the solvent by evaporation under reduced pressure.

Purification of the compounds in the examples may be carried out by conventional methods such as chromatography and/or re-crystallization using suitable solvents. Chromatographic methods are known to the skilled person and include e.g. column chromatography, flash chromatography, HPLC (high performance liquid chromatography), and MDAP (mass directed auto-preparation, also referred to as mass directed LCMS purification). MDAP is described in e.g. W. Goetzinger et al, Int. J. Mass Spectrom., 2004, 238, 153-162.

Analtech Silica Gel GF and E. Merck Silica Gel 60 F-254 thin layer plates were used for thin layer chromatography. Both flash and gravity chromatography were carried out on E. Merck Kieselgel 60 (230-400 mesh) silica gel. Preparative HPLC were performed using a Gilson Preparative System using a Luna 5 u C18(2) 100A reverse phase column eluting with a 10-80 gradient (0.1% TFA in acetonitrile/0.1% aqueous TFA) or a 10-80 gradient (acetonitrile/water). The CombiFlash system used for purification in this application was purchased from Isco, Inc. CombiFlash purification was carried out using a pre-packed SiO$_2$ column, a detector with UV wavelength at 254 nm and mixed solvents.

The terms "CombiFlash", "Biotage®", "Biotage 75" and "Biotage SP4®" when used herein refer to commercially available automated purification systems using pre-packed silica gel cartridges.

Final compounds were characterized with LCMS (conditions listed below) or NMR. $^1$H NMR or $^{19}$FNMR spectra were recorded using a Bruker Avance 400 MHz spectrometer. CDCl$_3$ is deuteriochloroform, DMSO-d$_6$ is hexadeuteriodimethylsulfoxide, and CD$_3$OD is tetradeuteriomethanol. Chemical shifts are reported in parts per million (ppm) downfield from the internal standard tetramethylsilane (TMS) or the NMR solvent. Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz.

All temperatures are reported in degrees Celsius. All other abbreviations are as described in the ACS Style Guide (American Chemical Society, Washington, D.C., 1986).

Absolute stereochemistry can be determined by methods known to one skilled in the art, for example X-ray or Vibrational circular dichroism (VCD).

When an enantiomer or a diasteroisomer is described and the absolute stereochemistry of a chiral center is not known, the use of "*" at the chiral centre denotes that the absolute stereochemistry of the chiral center is not known, i.e. the compound as drawn may be either a single R enantiomer or a single S enantiomer. Where the absolute stereochemistry at a chiral center of an enantiomer or a diasteroisomer is known, a bold wedge symbol (━━) or a hashed wedge symbol (┉┉) is used as appropriate, without the use of "*" at the chiral centre.

When a geometric or cis-trans isomer is described and the absolute configuration of the isomer is not known, the use of "*" at one of the atoms relevant to the geometric or cis-trans isomerism denotes that the absolute configuration at or around that atom is not known, i.e. the compound as drawn may be either a single cis isomer or a single trans enantiomer.

In the procedures that follow, after each starting material, reference to an intermediate is typically provided. This is provided merely for assistance to the skilled chemist. The starting material may not necessarily have been prepared from the batch referred to.

LCMS Conditions:
1) Acidic method:
a. Instruments: HPLC: Waters UPC2 and MS: Qda
Mobile phase: water containing 0.1% FA/0.1% MeCN
Column: ACQUITY UPLC BEH C$_{18}$ 1.7 μm 2.1×50 mm and 1.7 μm 2.1×100 mm
Detection: MS and photodiode array detector (PDA)
b. Instruments: HPLC: Shimadzu and MS: 2020
Mobile phase: water containing 0.1% FA/0.1% MeCN
Column: Sunfire C$_{18}$ 5 μm 50×4.6 mm and Sunfire C$_{18}$ 5 μm 150×4.6 mm
Detection: MS and photodiode array detector (PDA)
2) Basic conditions:
Instruments: HPLC: Agilent 1260 and MS: 6120
Mobile phase: 0.1% NH$_4$OH in H$_2$O/0.1% NH$_4$OH in ACN
Column: Xbridge C$_{18}$ 5 μm 50×4.6 mm and Xbridge C$_{18}$ 5 μm 150×4.6 mm
Detection: MS and photodiode array detector (DAD)
Prep-HPLC Conditions
Instrument: Waters instrument
Column: Xbridge Prep C$_{18}$ column OBD (10 μm, 19×250 mm), Xbrige prep C$_{18}$ 10 μm OBD™ 19×150 mm, Sunfire Prep C$_{18}$ 10×25 0 mm 5 μm, XBRIDGE Prep C$_{18}$ 10×150 mm 5 μm, etc
Acidic method:
Mobile phase: water containing 0.1% TFA/acetonitrile.
Basic method:
Mobile phase: water containing 0.1% NH$_4$OH/acetonitrile.
Chiral Prep-HPLC:
Thar SFC Prep 80 (TharSFC ABPR1, TharSFC SFC Prep 80 CO$_2$ Pump, TharSFC Co-Solvent Pump, TharSFC Cooling Heat Exchanger and Circulating Bath, TharSFC Mass Flow Meter, TharSFC Static Mixer, TharSFC Injection Module, Gilson UV Detector, TharSFC Fraction Collection Module
Chiral-HPLC Analysis:
Instrument: Thar SFC Prep 80 (TharSFC ABPR1, TharSFC SFC Prep 80 CO$_2$Pump, TharSFC Co-Solvent Pump, TharSFC Cooling Heat Exchanger and Circulating Bath, TharSFC Mass Flow Meter, TharSFC Static Mixer, TharSFC Injection Module, Gilson UV Detector, TharSFC Fraction Collection Module
Column and mobile phase: are described in below examples.

Abbreviations and Resource Sources

The following abbreviations and resources are used herein below:
Ac—acetyl
MeCN—acetonitrile
Atm—atmosphere
Aq.—aqueous
BINAP—2,2'-bis(diphenylphosphino)-1,1'-binaphthyl
Boc—tert-butyloxycarbonyl
Boc$_2$O—di-tert-butyl dicarbonate
Bn—benzyl
t-Bu—tert-butyl
conc.—concentrated
DAST—N,N-diethylaminosulfur trifluoride
DCE—1,2-dichloroethane
DCM—dichloromethane
DEA—diethanolamine
DMEDA—N,N'-Dimethylethylenediamine
Dess-Martin—1,1,1-Tris(acetyloxy)-1,1-dihydro-1,2-benziodoxol-3-(1H)-one
DHP—3,4-dihydro-2H-pyran
DIBAL-H—diisobutylaluminum hydride
DIEA—N,N-diisopropylethylamine
DIPEA—N, N-diisopropylethylamine
DMA—N, N-dimethylacetamide
DMAP—4-dimethylaminopyridine
DMEDA—N,N'-dimethylethylenediamine
DMF—N, N-dimethylformamide
DMP—Dess-Martin periodinane
DMSO—dimethyl sulfoxide
DPPF—1,1'-bis(diphenylphosphino)ferrocene
EA—ethyl acetate
EDC—1-ethyl-3-(3-dimethylaminopropyl)carbodiimide hydrochloride
EDCl—3-(ethyliminomethyleneamino)-N,N-dimethylpropan-1-amine
EtOH/EtOH—ethanol
Et$_2$O—diethyl ether
EtOAc—ethyl acetate
Et$_3$N—triethylamine FA—formic acid
HEP—heptane
Hex—hexane
HOAc-acetic acid
HATU—2-(1H-7-azabenzotriazol-1-yl)-1,1,3,3-tetramethyl uranium hexafluorophosphate
HOBT—hydroxybenzotriazole
IPA—isopropyl alcohol
$^i$PrOH/iPrOH—isopropyl alcohol
m-CPBA—meta-chloroperoxybenzoic acid
MOMCl—monochlorodimethyl ether
Me—methyl
MeOH—methanol
MsCl—methanesulfonyl chloride
NaHMDS—sodium bis(trimethylsilyl)amide
NIS—N-iodosuccinimide
NMP—1-methyl-2-pyrrolidone
NMO—4-methylmorpholine 4-oxide
PE—petroleum ether
PMB—p-methoxybenzyl
Pd$_2$(dba)$_3$—Tris(dibenzylideneacetone)dipalladium
Pd(dppf)Cl$_2$—1,1'-Bis(diphenylphosphino)ferrocenepalladium(II)dichloride dichloromethane complex
Ph$_3$P—triphenylphosphine
PhNTf$_2$—N,N-bis-(Trifluoromethanesulfonyl)aniline
PPTS—pyridinium p-toluenesulfonate
PTSA—p-toluenesulfonic acid
rt/RT—room temperature
Rt—retention time
sat.—saturated
SEM-Cl—2-(trimethylsilyl)ethoxymethyl chloride
SFC—Supercritical Fluid Chromatography
TBAI—Tetrabutylammonium iodide
TBDPSCl—tert-Butyl(chloro)diphenylsilane
TEA—triethylamine
TFA—trifluoroacetic acid
TFAA—trifluoroacetic anhydride
THF—tetrahydrofuran
TLC—thin layer chromatography
TsCl—4-toluenesulfonyl chloride
TsOH—p-toluenesulfonic acid Description A-1

4,6-Diiodo-2-methylpyrimidine (D A-1)

To a solution of NaI (11.9 g, 79.7 mmol) in HI (55%, 50 mL) was added 4,6-dichloro-2-methylpyrimidine (10.0 g, 61.3 mmol) in portions. The resulting suspension was heated to 40° C. and stirred for 1 hour. The reaction mixture was cooled and filtered. The solid was washed with water and then triturated with methanol (50 mL). The mixture was filtered to give the title compound (9.0 g, yield 42%) as white solid.

$^1$H NMR (400 MHz, CDCl$_3$): δ 8.07 (s, 1H), 2.67 (s, 3H).
LCMS (mobile phase: 5-95% acetonitrile in 2.5 min): Rt=1.59 min, MS Calcd: 346; MS Found: 347 [M+H]$^+$.

Description A-2

4,6-Diiodo-2-methoxypyrimidine (D A-2)

To a solution of NaI (5.5 g, 36.3 mmol) in HI (55% in water, 30 mL) was added 4,6-dichloro-2-methoxypyrimidine (5 g, 27.9 mmol). The mixture was heated to 40° C. and stirred for 14 h. The reaction mixture was cooled to room temperature and poured into ice water (50 mL). The filtered was washed with ice water three times to give product as a white solid (3.2 g, yield 32%).

LC-MS [mobile phase: from 80% water (0.1% TFA) and 20% CH3CN (0.1% TFA) to 20% water (0.1% TFA) and 80% CH$_3$CN (0.1% TFA) in 10 min]: purity 100%, Rt=4.72 min; MS Calcd.: 362, MS Found: 363 [M+H]$^+$.

Description A-3

(R)-2-(6-Iodo-2-methoxypyrimidin-4-yl)octahydro-pyrrolo[1,2-a]pyrazine (D A-3)

To a solution of (R)-octahydropyrrolo[1,2-a]pyrazine (209 mg, 1.66 mmol) and DIPEA (643 mg, 4.97 mmol) in EtOH (20 mL) was added 4,6-diiodo-2-methoxypyrimidine (600 mg, 1.66 mmol). The reaction was stirred at room temperature for 36 h. Solvent was removed in vacuum and the residue was purified by silica gel chromatography (eluted with PE/EtOAc=1:1) to give product (377 mg, yield 63.1%) as a pale yellow solid.

$^1$H NMR (400 MHz, CDCl$_3$): δ 6.65 (s, 1H), 4.54~4.17 (m, 2H), 3.90 (s, 3H), 3.14~3.02 (m, 3H), 2.67 (t, J=11.2 Hz, 1H), 2.23~2.13 (m, 2H), 1.98~1.74 (m, 4H), 1.51~1.41 (m, 1H).

Description A-4

(S)-2-(6-Iodo-2-methoxypyrimidin-4-yl)octahydro-pyrrolo[1,2-a]pyrazine (D A-4)

To a solution of (S)-octahydropyrrolo[1,2-a]pyrazine (209 mg, 1.66 mmol) and DIPEA (643 mg, 4.97 mmol) in EtOH (20 mL) was added 4,6-diiodo-2-methoxypyrimidine (600 mg, 1.66 mmol). The reaction was stirred at room temperature for 36 h. Solvent was removed in vacuum and the residue was purified by silica gel chromatography (eluted with PE/EtOAc=1:1) to give product (385 mg, yield 65%) as a pale yellow solid.

$^1$H NMR (400 MHz, CDCl$_3$): δ 6.65 (s, 1H), 4.49~4.17 (m, 2H), 3.90 (s, 3H), 3.14~3.00 (m, 3H), 2.67 (t, J=10.0 Hz, 1H), 2.23~2.13 (m, 2H), 1.98~1.75 (m, 4H), 1.51~1.41 (m, 1H).

Description A-5

(R)-2-(6-Iodo-2-methylpyrimidin-4-yl)octahydropyrrolo[1,2-a]pyrazine (D A-5)

To a solution of 4,6-diiodo-2-methylpyrimidine (300 mg, 0.87 mmol) and (R)-octahydropyrrolo[1,2-a]pyrazine (110 mg, 0.87 mmol) in THF/EtOH (5 mL/5 mL) was added DIEA (338 mg, 2.61 mmol). Then the reaction was stirred at room temperature for one day. Then the reaction was concentrated and purified by column (PE:EtOAc=7:1-4:1-1:1) to get a yellow solid (270 mg, yield: 90.5%).

LC-MS [mobile phase: from 60% water (0.1% TFA) and 40% CH$_3$CN (0.1% TFA) to 5% water (0.1% TFA) and 95% CH$_3$CN (0.1% TFA) in 2 min]: Rt=0.24 min; MS Calcd: 344, MS Found: 345 [M+H]$^+$.

Description A-6

(S)-2-(6-Iodo-2-methylpyrimidin-4-yl)octahydropyrrolo[1,2-a]pyrazine (D A-6)

To a solution of 4,6-diiodo-2-methylpyrimidine (200 mg, 0.58 mmol) and (S)-octahydropyrrolo[1,2-a]pyrazine dihydrochloride (115 mg, 0.58 mmol) in THF/EtOH (5 mL/5 mL) was added DIPEA (225 mg, 1.74 mmol). Then the reaction was stirred at room temperature for two days. Then the reaction was concentrated and purified by column chromatography (PE:EtOAc=4:1-1:1) to get desired product as off-white solid (90 mg, yield: 45).

LC-MS [mobile phase: from 60% water (0.1% TFA) and 40% CH$_3$CN (0.1% TFA) to 5% water (0.1% TFA) and 95% CH$_3$CN (0.1% TFA) in 2 min]: Rt=0.26 min; MS Calcd: 344, MS Found: 345 [M+H]$^+$.

Description A-7 cis-5-(6-Iodo-2-methylpyrimidin-4-yl)hexahydro-2H-furo[2,3-c]pyrrole (D A-7)

Run 1: To a stirred solution of rel-(3aR,6aR)-hexahydro-2H-furo[3,2-c]pyrrole (98 mg, 0.866 mmol) in DMF (1.0 ml) were added 4,6-diiodo-2-methylpyrimidine (300 mg, 0.866 mmol) and DIPEA (0.70 ml, 4.24 mmol). The reaction was stirred at room temperature overnight. The reaction mixture was combined with reaction mixture of next run for further workup procedures.

Run 2: To a stirred solution of rel-(3aR,6aR)-hexahydro-2H-furo[3,2-c]pyrrole (130 mg, 1.16 mmol) in DMF (1.5 ml) were added 4,6-diiodo-2-methylpyrimidine (400 mg, 1.16 mmol) and DIPEA (1.0 ml, 6.05 mmol). The reaction was stirred at room temperature overnight. The reaction solution was combined with reaction mixture of previous run, concentrated to dryness and the yellow residue oil was diluted with ice sat. aqueous Na$_2$CO$_3$ (20 ml). The resultant was extracted with EtOAc (3×25 ml) and the combined organic layers were washed by brine (20 ml), dried over anhydrous Na$_2$SO$_4$ and filtered. The filtrate was concentrated and the residue was purified by silica gel chromatography (wet-loaded with CH$_2$Cl$_2$) eluted with PE/EtOAc=3/1 afforded pure desired product as a yellow thick oil (514 mg, yield over 2 batches: 76%).

LC-MS [mobile phase: from 90% water (0.1% TFA) and 10% CH$_3$CN (0.1% TFA) to 5% water (0.1% TFA) and 95% CH$_3$CN (0.1% TFA) in 2.6 min]: Rt=1.08 min; MS Calcd: 331, MS Found: 332 [M+H]$^+$.

$^1$H NMR (400 MHz, CDCl$_3$) δ6.59 (s, 1H), 4.60 (s, 1H), 3.99 (q, J=7.6 Hz, 1H), 3.92-3.86 (m, 1H), 3.72 (br s, 2H), 3.52 (br s, 1H), 3.29 (br s, 1H), 3.00 (t, J=6.0 Hz, 1H), 2.46 (s, 3H), 2.23-2.14 (m, 1H), 1.92-1.88 (m, 1H).

Description A-8 tert-Butyl 3-(pyrazin-2-yl)propanoate (D A-8)

A solution of 2-methylpyrazine (6.58 g, 70.0 mmol) in THF (20 mL) was added dropwise to a solution of LDA (2.0 M in THF, 45.5 mL, 91.0 mmol) in THF (60 mL) at −78° C. under nitrogen atmosphere. After the mixture was stirred at −78° C. for 30 min, tert-butyl 2-bromoacetate (13.7 g, 70.0 mmol) was added and the resulting mixture was stirred at −78° C. for 2 hrs. Then the mixture was poured into water (100 mL) and extracted with EtOAc (100 mL×2). The combined organic layers were washed with brine, dried over anhydrous sodium sulfate and concentrated in reduced pressure. The residue was purified by column chromatography (petroleum ether:EtOAc=6:1) to give the title compound (5.4 g, yield 37%) as a pale yellow oil.

$^1$H NMR (300 MHz, CDCl$_3$): δ 8.49-8.47 (m, 2H), 8.40 (s, 1H), 3.09 (t, J=7.2 Hz, 2H), 2.72 (t, J=6.9 Hz, 2H), 1.40 (s, 9H).

Description A-9 tert-Butyl 3-(piperazin-2-yl)propanoate (D A-9)

A suspension of tert-butyl 3-(pyrazin-2-yl)propanoate (5.49 g, 26.4 mmol) and Pd/C (10% wet, 1.5 g) in methanol (150 mL) was hydrogenated over 55 psi at 50° C. for 18 hrs. The reaction mixture was filtered and the filtrate was concentrated in reduced pressure to give the title compound (4.7 g, 83%) as pale yellow oil which was used for the next step without further purification.

$^1$H NMR (300 MHz, CDCl$_3$): δ 2.97-2.59 (m, 6H), 2.39-2.24 (m, 3H), 1.60-1.53 (m, 2H), 1.43 (s, 9H).

Description A-10 tert-Butyl 3-(4-(6-iodo-2-methoxypyrimidin-4-yl)piperazin-2-yl)propanoate (D A-10)

A mixture of tert-butyl 3-(piperazin-2-yl)propanoate (0.57 g, 2.66 mmol) and 4,6-diiodo-2-methoxypyrimidine (962 mg, 2.66 mmol) and triethylamine (0.40 g, 4.0 mmol) in methanol (10 mL) was stirred at 70° C. for 1 h. The reaction mixture was directly concentrated in reduced pressure. The residue was partitioned with water (80 mL) and EtOAc (60 mL). The organic layer was separated and the aqueous layer was extracted with EtOAc (50 mL). The combined organic layers were washed with brine, dried over anhydrous sodium sulfate and concentrated. The residue was purified by column chromatography (EtOAc) to give the title compound (0.84 g, yield 70%) as pale yellow oil.

$^1$H NMR (300 MHz, CDCl$_3$): δ 6.62 (s, 1H), 4.13-4.08 (m, 2H), 3.90 (s, 3H), 3.09-2.60 (m, 5H), 2.36-2.32 (m, 2H), 1.77-1.66 (m, 2H), 1.45 (s, 9H).

Description A-11 tert-Butyl 2-(3-(tert-butoxy)-3-oxopropyl)-4-(6-iodo-2-methoxypyrimidin-4-yl)piperazine-1-carboxylate (D A-11)

To a solution of tert-butyl 3-(4-(6-iodo-2-methoxypyrimidin-4-yl)piperazin-2-yl)propanoate (840 mg, 1.88 mmol) and triethylamine (380 mg, 3.75 mmol) in THF (10 mL) was added Boc$_2$O (490 mg, 2.25 mmol). The reaction mixture was stirred at room temperature for 5 hrs. The mixture was poured into water (70 mL) and extracted with EtOAc (50 mL×2). The combined organic layers were washed with brine (100 mL), dried over Na$_2$SO$_4$ and concentrated in reduced pressure. The residue was purified by column chromatography (petroleum ether:EtOAc=6:1) to give the title compound (0.92 g, yield 90%) as a pale yellow oil.

$^1$H NMR (300 MHz, CDCl$_3$): δ 6.61 (s, 1H), 4.25-3.98 (m, 4H), 3.90 (s, 3H), 3.19-2.99 (m, 3H), 2.29-2.16 (m, 2H), 1.90-1.87 (m, 1H), 1.73-1.68 (m, 1H), 1.48 (s, 9H), 1.43 (s, 9H).

Description A-12

6-Bromo-5-methyl-1H-indazole (D A-12)

To a solution of 5-bromo-2,4-dimethylaniline (15.0 g, 75.0 mmol) in chloroform (150 mL) was added Ac$_2$O (15.0, 150 mmol) under ice bath. KOAc (8.00 g, 82.5 mmol), 18-crown-6 (10.0 g, 37.5 mmol) and isoamyl nitrite (26.3 g, 225 mmol) were added. The mixture was refluxed for 36 hrs. The reaction mixture was concentrated and the residue was dissolved in EtOAc (500 mL). The organic solution was washed with water (100 mL), dried over $Na_2SO_4$ and concentrated. The residue was dissolved in THF (100 mL) and NaOH (4 M, 40.0 mL, 160 mmol) was added. The mixture was stirred at rt for 1 h. The solvent was removed under vacuum and the residue was partitioned between EtOAc (400 mL) and water (200 mL). The organic layer was washed with brine, dried over $Na_2SO_4$ and concentrated. The crude was purified by column chromatography (PE:EtOAc from 10:1 to 5:1) to give the title compound (5.1 g, yield 32%) as an orange solid.

$^1$H NMR (300 MHz, $CDCl_3$): δ 10.20 (br, 1H), 7.99 (s, 1H), 7.75 (s, 1H), 7.61 (s, 1H), 2.50 (s, 3H).

Description A-13

6-Bromo-5-methyl-1-(tetrahydro-2H-pyran-2-yl)-1H-indazole (D A-13)

To a solution of 6-bromo-5-methyl-1H-indazole (5.10 g, 24.2 mmol) in dry DCM (120 mL) was added DHP (4.10 g, 48.4 mmol), TsOH (0.800 g, 4.80 mmol) and $Mg_2SO_4$ (5.0 g) at rt. The reaction mixture was heated to 35° C. and stirred for an hour. The reaction mixture was filtered and the filtrate was washed with $Na_2CO_3$ (10%, 100 mL), dried over $Na_2SO_4$ and concentrated. The crude was purified by column chromatography (PE:EtOAc from 50:1 to 20:1) to give the title compound (6.0 g, yield 84%) as an orange solid.

$^1$H NMR (300 MHz, $CDCl_3$): δ 7.90 (s, 1H), 7.84 (s, 1H), 7.55 (s, 1H), 5.63 (dd, J=9.6, 3.0 Hz, 1H), 4.05-4.00 (m, 1H), 3.78-3.70 (m, 1H), 2.58-2.44 (m, 4H), 2.20-2.02 (m, 2H), 1.78-1.65 (m, 3H).

LCMS (mobile phase: 5-95% $CH_3CN$): Rt=2.19 min in 3 min; MS Calcd: 294; MS Found: 295 [M+H]$^+$.

Description A-14 tert-Butyl 4-(5-methyl-1-(tetrahydro-2H-pyran-2-yl)-1H-indazol-6-yl)-5,6-dihydropyridine-1(2H)-carboxylate (D A-14)

To a suspension of 6-bromo-5-methyl-1-(tetrahydro-2H-pyran-2-yl)-1H-indazole (5.50 g, 18.6 mmol), tert-butyl 4-(4,4,5,5-tetramethyl-1,3,2-dioxaborolan-2-yl)-5,6-dihydropyridine-1(2H)-carboxylate (6.90 g, 22.3 mmol) and $Na_2CO_3$ (4.90 g, 46.5 mmol) in dioxane (150 mL) and water (130 mL) was added Pd(dppf)$Cl_2$ (658 mg, 0.900 mmol). The mixture was degassed with $N_2$ for 3 times and then stirred at 80° C. overnight. The solvent was removed under vacuum and the residue was partitioned between EtOAc (300 mL) and water (200 mL). The combined organic layers were washed with brine, dried over $Na_2SO_4$ and concentrated. The crude was purified by column chromatography (PE:EtOAc=10:1) to give the title compound (7.3 g, yield 99%) as a slight brown solid.

$^1$H NMR (400 MHz, $CDCl_3$): b 7.92 (s, 1H), 7.48 (s, 1H), 7.28 (s, 1H), 5.67 (dd, J=9.6, 2.8 Hz, 1H), 5.63 (br s, 1H), 4.07-4.01 (m, 3H), 3.78-3.70 (m, 1H), 3.67-3.64 (m, 2H), 2.62-2.53 (m, 1H), 2.45-2.39 (m, 2H), 2.34 (s, 3H), 2.18-2.12 (m, 1H), 2.07-2.02 (m, 1H), 1.81-1.73 (m, 2H), 1.69-1.61 (m, 1H), 1.52 (s, 9H).

Descriptions A-15 and A-16

Trans-tert-butyl 3-hydroxy-4-(5-methyl-1-(tetrahydro-2H-pyran-2-yl)-1H-indazol-6-yl)piperidine-1-carboxylate (D A-15 and D A-16)

To a solution of tert-butyl 4-(5-methyl-1-(tetrahydro-2H-pyran-2-yl)-1H-indazol-6-yl)-5,6-dihydropyridine-1(2H)-carboxylate (33.0 g, 83.0 mmol) in dry THF (300 mL) was added $BH_3$-THF (1 M, 332 mL, 332 mmol) at 10° C. The mixture was gradually warmed to rt and stirred overnight. The reaction mixture was cooled to 0° C. and NaOH (aq, 2 M, 125 mL, 249 mmol) was added carefully. $H_2O_2$(30%, 87 mL, 830 mmol) was followed. The temperature was kept below 10° C. during the addition of NaOH and $H_2O_2$. The mixture was stirred for an hour at rt. $Na_2SO_3$ (10%, 100 mL) was added to the reaction mixture and stirred for 20 min. The organic layer was separated and the aqueous was extracted with EtOAc (100 mL×2). The combined organic layers were washed with brine, dried over $Na_2SO_4$ and evaporated. The crude was purified by column chromatography (PE:EtOAc from 3:1 to 1:1) to give tert-butyl 3-hydroxy-4-(5-methyl-1-(tetrahydro-2H-pyran-2-yl)-1H-indazol-6-yl)piperidine-1-carboxylate as major product (D A-15) (23 g, yield 67%) as a white solid and tert-butyl 4-(5-methyl-1-(tetrahydro-2H-pyran-2-yl)-1H-indazol-6-yl)piperidine-1-carboxylate (D A-16) as minor product (6.7 g, yield 20%) as a slight brown solid.

$^1$H NMR (300 MHz, $CDCl_3$): δ 7.90 (s, 1H), 7.48 (s, 1H), 7.34 (s, 1H), 5.68 (dd, J=9.6 Hz, 2.7 Hz, 1H), 4.33-4.28 (m, 2H), 4.06-4.02 (m, 1H), 3.80-3.72 (m, 1H), 3.00-2.82 (m, 3H), 2.65-2.51 (m, 1H), 2.44 (s, 3H), 2.22-2.11 (m, 1H), 2.08-2.00 (m, 1H), 1.88-1.80 (m, 2H), 1.77-1.63 (m, 5H), 1.51 (s, 9H).

Description A-17

5-Methyl-6-(piperidin-4-yl)-1H-indazole hydrochloride (D A-17)

tert-Butyl 4-(5-methyl-1-(tetrahydro-2H-pyran-2-yl)-1H-indazol-6-yl)piperidine-1-carboxylate (1.0 g, 2.5 mmol) was dissolved in HCl/MeOH (5 mol/L, 10 mL). Then the mixture was stirred for 6 hrs. The mixture was concentrated under reduced pressure to afford the title compound (820 mg, yield >100%) as a light yellow solid used for next step without purification.

LC-MS: 5-95% $CH_3CN$, Rt=1.13 min, MS Calcd.: 215, MS Found: 216 [M+H]$^+$.

Description A-18 tert-Butyl 4-(5-methyl-1H-indazol-6-yl)piperidine-1-carboxylate (D A-18)

To a solution of 5-methyl-6-(piperidin-4-yl)-1H-indazole hydrochloride (600 mg, 2.39 mmol) in $CH_3OH$ (10 mL) and $H_2O$ (2 mL) was added KOH (268 mg, 4.78 mmol) and (Boc)$_2$O (781 mg, 3.58 mmol) under ice bath. The reaction mixture was stirred at rt for 2 hrs. The reaction mixture was diluted with water (50 mL) and extracted with EtOAc (50 mL×3). The combined organic layers were dried over $Na_2SO_4$ and concentrated. The residue was purified by column chromatograph (PE:EtOAc from 10:1 to 4:1) to give the title compound (353 mg, yield 47%) as a yellow oil.

$^1$H NMR (300 MHz, $CDCl_3$): δ 10.15 (br s, 1H), 7.95 (s, 1H), 7.53 (s, 1H), 7.29 (s, 1H), 4.34 (br s, 2H), 2.95-2.81 (m, 3H), 2.45 (s, 3H), 1.86-1.81 (m, 2H), 1.69-1.61 (m, 2H), 1.51 (s, 9H).

Description A-19

(cis)-tert-Butyl 3-fluoro-4-(5-methyl-1-(tetrahydro-2H-pyran-2-yl)-1H-indazol-6-yl) piperidine-1-carboxylate (D A-19)

To a solution of (trans)-tert-Butyl 3-hydroxy-4-(5-methyl-1-(tetrahydro-2H-pyran-2-yl)-1H-indazol-6-yl)piperidine- 1-carboxylate (24.5 g, 59.0 mmol) in dry DCM (200 mL) was added DAST (38.0 g, 236 mmol) under $N_2$ at −65° C. The mixture was gradually warmed to rt and stirred for 2 hrs. The reaction mixture was carefully poured into $Na_2CO_3$ aqueous solution (10%, 300 mL) and stirred for 20 min. The organic layer was separated and the aqueous was extracted with DCM (250 mL×2). The combined organic layers were washed with brine, dried over $Na_2SO_4$ and evaporated. The crude was purified by column chromatography (PE:EtOAc=10:1) to give the title compound (11.8 g, yield 48%) as a white solid.

$^1$H NMR (400 MHz, $CDCl_3$): δ7.92 (s, 1H), 7.52 (s, 1H), 7.41 (s, 1H), 5.74-5.67 (m, 1H), 4.80-4.59 (m, 2H), 4.21 (br, 1H), 4.07-3.99 (m, 1H), 3.80-3.71 (m, 1H), 3.25-3.19 (m, 1H), 2.89-2.79 (m, 2H), 2.65-2.51 (m, 1H), 2.45 (s, 3H), 2.19-2.15 (m, 1H), 2.15-2.04 (m, 1H), 1.93-1.88 (m, 1H), 1.80-1.74 (m, 5H), 1.52 (s, 9H).

LCMS: 5-95% $CH_3CN$, Rt=2.25 min in 3 min; MS Calcd: 417; MS Found: 418 $[M+H]^+$.

Description A-20

(cis)-6-(3-Fluoropiperidin-4-yl)-5-methyl-1H-indazole hydrochloride (D A-20)

A mixture of (cis)-tert-butyl 3-fluoro-4-(5-methyl-1-(tetrahydro-2H-pyran-2-yl)-1H-indazol-6-yl) piperidine-1-carboxylate (2.50 g, 6.00 mmol) in HCl/dioxane (6 mol/L, 40 mL) was stirred at rt for 6 hrs. The reaction mixture was cooled to 0° C. and filtered. The solid was washed with cold 1,4-dioxane (5 mL) to get the title compound (1.4 g, yield 100%) as a white solid which was used for next step directly.

LC-MS: 5-95% $CH_3CN$, Rt=1.73 min; MS Calcd.: 233, MS Found: 234 $[M+H]^+$.

Description A-21

(cis)-6-(3-Fluoro-1-(oxetan-3-yl)piperidin-4-yl)-5-methyl-1H-indazole (D A-21)

To a solution of (cis)-6-(3-fluoropiperidin-4-yl)-5-methyl-1H-indazole hydrochloride (1.40 g, 6.00 mmol) and oxetan-3-one (2.16 g, 30.0 mmol) in methanol (5 mL) and 1,2-dichloroethane (50 mL) was added $NaBH_3CN$ (1.13 g, 18.0 mmol). Then the mixture was stirred at rt for 3 hrs. The reaction mixture was diluted with water (100 mL) and extracted with dichloromethane (100 mL×3). The combined organic layers were dried over $MgSO_4$, filtered and concentrated. The crude was purified by column chromatography (DCM:MeOH=30:1) to give the title compound (1.0 g, yield 57.6%) as a white solid.

LC-MS: 5%-95% $CH_3CN$, Rt=1.85 min; MS Calcd.: 289, MS Found: 290 $[M+H]^+$.

Description A-22

6-(3,6-Dihydro-2H-pyran-4-yl)-5-methyl-1-(tetrahydro-2H-pyran-2-yl)-1H-indazole (D A-22)

To a mixture of 2-(3,6-dihydro-2H-pyran-4-yl)-4,4,5,5-tetramethyl-1,3,2-dioxaborolane (939 mg, 4.47 mmol), 6-bromo-5-methyl-1-(tetrahydro-2H-pyran-2-yl)-1H-indazole (1200 mg, 4.07 mmol), $PdCl_2(dppf)\cdot CH_2Cl_2$ adduct (332 mg, 0.407 mmol) and tripotassium phosphate (2589 mg, 12.20 mmol) was added DMF (10 mL) and water (2.500 mL). The reaction mixture was heated to 100° C. for 3 h. The reaction mixture was diluted with ethyl acetate and filtered, the filtrate was concentrated and purified by silica column (30% EA in PE) to give 6-(3,6-dihydro-2H-pyran-4-yl)-5-methyl-1-(tetrahydro-2H-pyran-2-yl)-1H-indazole (610 mg, 2.044 mmol, 50.3% yield).

MS: 299.0 $[M+H]^+$.

Description A-23

5-Methyl-1-(tetrahydro-2H-pyran-2-yl)-6-(tetrahydro-2H-pyran-4-yl)-1H-indazole (D A-23)

A mixture of 6-(3,6-dihydro-2H-pyran-4-yl)-5-methyl-1-(tetrahydro-2H-pyran-2-yl)-1H-indazole (610 mg, 2.044 mmol), Pd—C (435 mg, 0.409 mmol, 10%) and methanol (10 mL) was stirred under hydrogen balloon atmosphere at rt for 16 h, then filtered. The filtrate was concentrated to afford a crude 5-methyl-1-(tetrahydro-2H-pyran-2-yl)-6-(tetrahydro-2H-pyran-4-yl)-1H-indazole (614 mg, 2.044 mmol, 100% yield).

MS: 301.1 $[M+H]^+$.

Description A-24

5-Methyl-6-(tetrahydro-2H-pyran-4-yl)-1H-indazole (D A-24)

A solution of 5-methyl-1-(tetrahydro-2H-pyran-2-yl)-6-(tetrahydro-2H-pyran-4-yl)-1H-indazole (610 mg, 2.031 mmol), HCl (4.06 mL, 20.31 mmol) and methanol (5 mL) was stirred at rt for 16 h. The reaction solution was neutralized by aq. $NaHCO_3$ to pH=7 and extracted with ethyl acetate. The combined organic phases were dried and concentrated to give 5-methyl-6-(tetrahydro-2H-pyran-4-yl)-1H-indazole (430 mg, 1.988 mmol, 98% yield).

MS: 217.1 $[M+H]^+$.

Description A-25 tert-Butyl 2-(3-(tert-butoxy)-3-oxopropyl)-4-(2-methoxy-6-(5-methyl-6-(tetrahydro-2H-pyran-4-yl)-1H-indazol-1-yl)pyrimidin-4-yl)piperazine-1-carboxylate (D A-25)

A mixture of 5-methyl-6-(tetrahydro-2H-pyran-4-yl)-1H-indazole (0.22 g, 1.0 mmol) and tert-butyl 2-(3-(tert-butoxy)-3-oxopropyl)-4-(6-iodo-2-methoxypyrimidin-4-yl)piperazine-1-carboxylate (0.55 g, 1.0 mmol), CuI (0.15 g. 0.80 mmol), N,N'-dimethyl-cyclohexane-1,2-diamine (0.23 g, 1.6 mmol) and potassium phosphate (0.34 g, 1.6 mmol) in toluene (8 mL) was stirred at 110° C. nitrogen atmosphere for 18 hrs. After cooled down to rt the mixture was poured into diluted ammonia solution (10%, 50 mL) and extracted with ethyl acetate (30 mL×3). The combined organic layers were washed with brine (50 mL), dried over $Na_2SO_4$ and concentrated. The residue was purified by column chromatography (petroleum ether:EtOAc=4:1) to give the mixture of the crude product, which was further purified by prep-HPLC ($ACN/H_2O$, 20-95%) to give the title compound (0.22 g, yield 35%) as a white solid.

$^1$H NMR (300 MHz, $CDCl_3$): δ 8.76 (s, 1H), 8.06 (d, J=3.0 Hz, 1H), 7.52 (s, 1H), 6.84 (s, 1H), 4.38-3.99 (m, 9H), 3.65-3.57 (m, 2H), 3.27-3.06 (m, 4H), 2.48 (s, 3H), 2.30-2.19 (m, 2H), 1.99-1.79 (m, 6H), 1.49 (s, 9H), 1.41 (s, 9H).

Descriptions A-26 and A-27 tert-Butyl 2-(3-(tert-butoxy)-3-oxopropyl)-4-(2-methoxy-6-(5-methyl-6-(tetrahydro-2H-pyran-4-yl)-1H-indazol-1-yl)pyrimidin-4-yl)piperazine-1-carboxylate (peak 1, D A-26; peak 2, D A-27)

tert-Butyl 2-(3-(tert-butoxy)-3-oxopropyl)-4-(2-methoxy-6-(5-methyl-6-(tetrahydro-2H-pyran-4-yl)-1H-indazol-1-yl)pyrimidin-4-yl)piperazine-1-carboxylate (0.22 g, 0.35 mmol) was purified by chiral prep. column (IC, Hex; EtOH=60:40, 12 mL/min, 254 nm) to give Peak 1 (D A-26, 85 mg, yield 39%) as white solid and Peak 2 (D A-27, 80 mg, yield 36%) as white solid.

Peak 1: $^1$H NMR (300 MHz, CDCl$_3$): δ 8.76 (s, 1H), 8.06 (s, 1H), 7.52 (s, 1H), 6.84 (s, 1H), 4.38-4.11 (m, 8H), 4.02-4.00 (m, 1H), 3.65-3.57 (m, 2H), 3.27-3.04 (m, 4H), 2.48 (s, 3H), 2.30-2.19 (m, 2H), 1.97-1.75 (m, 6H), 1.49 (s, 9H), 1.41 (s, 9H). Chiral HPLC: Chiral pak IC 5 μm 4.6×250 mm, Hex:EtOH=60:40, Flow: 1.0 ml/min, 230 nm, T=30° C. Rt=10.189 min, 100% ee.

Peak 2: $^1$H NMR (300 MHz, CDCl$_3$): δ 8.76 (s, 1H), 8.07 (s, 1H), 7.52 (s, 1H), 6.83 (s, 1H), 4.38-4.14 (m, 8H), 4.03-4.00 (m, 1H), 3.64-3.57 (m, 2H), 3.27-3.04 (m, 4H), 2.48 (s, 3H), 2.30-2.19 (m, 2H), 1.99-1.75 (m, 6H), 1.49 (s, 9H), 1.41 (s, 9H). Chiral condition: Chiral pak IC 5 μm 4.6×250 mm, Hex:EtOH=60:40, Flow: 1.0 ml/min, 230 nm, T=30° C. Rt=12.626 min, 100% ee.

Description A-28

5-Methyl-6-(1-(oxetan-3-yl)piperidin-4-yl)-1H-indazole (D A-28)

To a solution of 5-methyl-6-(piperidin-4-yl)-1H-indazole hydrochloride (820 mg of crude, 2.50 mmol) in DCE (15 mL) was added oxetan-3-one (1.80 g, 25.0 mmol). The mixture was stirred at room temperature for 40 min. Then the mixture was cooled under ice bath and NaBH$_3$CN (473 mg, 7.50 mmol) was added to the mixture. The mixture was warmed to room temperature and stirred for 2 hrs. Then the reaction mixture was poured into Na$_2$CO$_3$ aqueous solution (10%, 100 mL) and stirred for 15 min. Then the mixture was extracted with EtOAc (30 mL×3). The combined organic layers were washed with brine, dried over Na$_2$SO$_4$ and concentrated. The residue was purified by column chromatography (DCM:MeOH=40:1) to afford the title compound (473 mg, yield 70%) as a white solid $^1$H NMR (300 MHz, CDCl$_3$): δ 10.11 (br, 1H), 7.96 (s, 1H), 7.53 (s, 1H), 7.38 (s, 1H), 4.72-4.69 (m, 4H), 3.61-3.52 (m, 1H), 2.96-2.93 (m, 2H), 2.88-2.78 (m, 1H), 2.44 (s, 3H), 2.06-1.98 (m, 2H), 1.90-1.82 (m, 4H).

LC-MS: [mobile phase: 5-95% Acetonitrile in 2.5 min]: Rt=1.37 min; MS Calcd: 271; MS Found: 272 [M+H]$^+$.

Description A-29

3-Benzyl-3-azabicyclo[3.1.0]hexan-1-ol (D A-29)

To a solution of ethyl 2-(allyl(benzyl)amino)acetate (2.00 g, 8.58 mmol) in THF (160 mL) was added TiCl(O$^i$Pr)$_3$ (1.0 mL, 3.42 mmol) in one portion at rt. Then isopropylmagnesium chloride (2 M in THF, 21.6 mL, 43.0 mmol) was added dropwise via a syringe pump over 3 hrs. After the addition, the mixture was stirred at rt overnight. The reaction was quenched with water (20 mL). The mixture was diluted with ethyl acetate (300 mL) and water (100 mL). The organic solution was washed brine (100 mL×2), dried over Na$_2$SO$_4$ and concentrated. The residue was purified by reverse phase chromatography (ACN/water: 30-100%) to give the crude (710 mg with 70% purity by NMR). The crude was further purified by normal phase chromatography (CH$_2$Cl$_2$:methanol=80:1) to give the desired compound (320 mg, yield 20%) as a slight yellow oil.

$^1$H NMR (300 MHz, CDCl$_3$): δ 7.30-7.22 (m, 5H), 3.65 (s, 2H), 3.16-3.13 (m, 1H), 2.80-2.77 (m, 1H), 2.67-2.61 (m, 2H), 1.47-1.41 (m, 1H), 1.19-1.16 (m, 1H), 0.95-0.91 (m, 1H).

Description A-30

3-Azabicyclo[3.1.0]hexan-1-ol (D A-30)

To a solution of 3-benzyl-3-azabicyclo[3.1.0]hexan-1-ol (320 mg, 1.69 mmol) in methanol (20 mL) was added Pd(OH)$_2$ (50 mg) at rt. The mixture was stirred under H$_2$ (balloon) for 3 hrs. The mixture was filtered and the filtrate was concentrated under vacuum to give the desired compound (150 mg, yield 90%) with 90% purity by NMR as a colorless oil.

$^1$H NMR (300 MHz, CDCl$_3$): δ 3.15-3.08 (m, 2H), 3.01-2.97 (m, 1H), 2.74-2.70 (m, 1H), 1.43-1.38 (m, 1H), 1.09-1.04 (m, 1H), 0.67-0.64 (m, 1H).

Description A-31 tert-Butyl 4-(1-(6-iodo-2-methylpyrimidin-4-yl)-5-methyl-1H-indazol-6-yl)piperidine-1-carboxylate (D A-31)

To a mixture of tert-butyl 4-(5-methyl-1H-indazol-6-yl)piperidine-1-carboxylate (780 mg, 2.48 mmol) in toluene (20 mL) was added 4,6-diiodo-2-methylpyrimidine (1.10 g, 3.22 mmol), K$_3$PO$_4$ (2.60 g, 12.40 mmol), CuI (476 mg, 2.50 mmol) and N,N'-dimethyl-cyclohexane-1,2-diamine (298 mg, 2.09 mmol). The reaction mixture was heated to 100° C. and stirred for 3 hrs. The reaction mixture was cooled to room temperature and poured into water (100 mL). The desired was extracted with EtOAc (50 mL×3). The combined organic layers were washed with brine (30 mL), dried over Na$_2$SO$_4$ and concentrated. The residue was purified by column (PE:EtOAc=12:1) to give the title compound (800 mg, yield 62%) as a white solid.

$^1$H NMR (300 MHz, CDCl$_3$): δ 8.65 (s, 1H), 8.26 (s, 1H), 8.11 (s, 1H), 7.53 (s, 1H), 4.39-4.24 (m, 2H), 2.99-2.81 (m, 3H), 2.77 (s, 3H), 2.49 (s, 3H), 1.90-1.1.79 (m, 2H), 1.77-1.63 (m, 2H), 1.51 (s, 9H).

Description A-32 tert-Butyl 4-(1-(6-(1-hydroxy-3-azabicyclo[3.1.0]hexan-3-yl)-2-methylpyrimidin-4-yl)-5-methyl-1H-indazol-6-yl)piperidine-1-carboxylate (D A-32)

To a mixture of tert-butyl 4-(1-(6-iodo-2-methylpyrimidin-4-yl)-5-methyl-1H-indazol-6-yl)piperidine-1-carboxylate (400 mg, 0.750 mmol), 3-azabicyclo[3.1.0]hexan-1-ol (150 mg crude, 1.21 mmol), Pd$_2$(dba)$_3$ (69 mg, 0.075 mmol) and Cs$_2$CO$_3$ (975 mg, 3.00 mmol) in THF (20 mL) was added Xphos (38 mg, 0.079 mmol) under N$_2$ atmosphere. The reaction mixture was refluxed for 8 hrs. The reaction mixture was concentrated. The residue was partitioned with EtOAc (100 mL) and water (50 mL). The organic layer was washed with brine, dried over Na$_2$SO$_4$ and concentrated.

The residue was purified by column (PE:EtOAc=5:1) to give crude product (75 mg) as a brown oil. The crude was further purified by prep. TLC (PE:EtOAc=2:1) to give the title compound (40 mg, yield 11%) as a slight yellow solid. $^1$H NMR (300 MHz, CDCl$_3$): δ 8.74 (s, 1H), 8.04 (s, 1H), 7.49 (s, 1H), 6.66 (s, 1H), 4.37-4.25 (m, 2H), 3.68-3.63 (m, 2H), 2.97-2.84 (m, 3H), 2.60 (s, 3H), 2.46 (s, 3H), 1.90-1.76 (m, 6H), 1.51 (s, 9H), 1.30-1.26 (m, 2H), 0.71-0.67 (m, 1H).

Description A-33

8-(6-Iodo-2-methoxypyrimidin-4-yl)octahydropyrazino[2,1-c][1,4]oxazine (D A-33)

A mixture of 4,6-diiodo-2-methoxypyrimidine (200 mg, 0.55 mmol), octahydropyrazino[2,1-c][1,4]oxazine (119 mg, 0.55 mmol) and DIEA (357 mg, 2.76 mmol) in THF (20 mL) and i-PrOH (20 mL) was stirred at 50° C. overnight. The reaction solution was concentrated and the residue was diluted with EtOAc (30 mL). The resulting mixture was washed with brine (30 mL), dried over anhydrous Na$_2$SO$_4$ and concentrated. The residue was purified by silica gel chromatography column (CH$_2$Cl$_2$:MeOH=20:1) to give product as a yellow solid (160 mg, 77% yield)

LC-MS [mobile phase: from 60% water (0.1% FA) and 40% CH$_3$CN (0.1% FA) to 5% water (0.1% FA) and 95% CH$_3$CN (0.1% FA) in 2.0 min]: Rt=0.49 min; MS Calcd.: 376, MS Found: 377 [M+H]$^+$.

Description B-1

4,6-Diiodo-2-methylpyrimidine (D B-1)

To a solution of NaI (11.9 g, 79.7 mmol) in HI (55%, 50 mL) was added 4,6-dichloro-2-methylpyrimidine (10.0 g, 61.3 mmol) in portions. The resulting suspension was heated to 40° C. and stirred for 1 hour. The reaction mixture was cooled and filtered. The solid was washed with water and then triturated with methanol (50 mL). The mixture was filtered to give the title compound (9.0 g, yield 42%) as white solid.

$^1$H NMR (400 MHz, CDCl$_3$): δ 8.07 (s, 1H), 2.67 (s, 3H).
LCMS (mobile phase: 5-95% acetonitrile in 2.5 min): Rt=1.59 min, MS Calcd: 346; MS Found: 347 [M+H]$^+$.

Description B-2

4,6-Diiodo-2-methoxypyrimidine (D B-2)

To a solution of NaI (5.5 g, 36.3 mmol) in HI (55% in water, 30 mL) was added 4,6-dichloro-2-methoxypyrimidine (5 g, 27.9 mmol). The mixture was heated to 40° C. and stirred for 14 h. The reaction mixture was cooled to room temperature and poured into ice water (50 mL). The filtered was washed with ice water three times to give product as a white solid (3.2 g, yield 32%).

LC-MS [mobile phase: from 80% water (0.1% TFA) and 20% ACN (0.1% TFA) to 20% water (0.1% TFA) and 80% ACN (0.1% TFA) in 10 min]: Rt=4.72 min; MS Calcd.: 362, MS Found: 363 [M+H]$^+$.

Description B-3

8-(6-Iodo-2-methylpyrimidin-4-yl)-2,5-dioxa-8-azaspiro[3.5]nonane (D B-3)

To a solution of 4,6-diiodo-2-methylpyrimidine (300 mg, 0.87 mmol) and 2,5-dioxa-8-azaspiro[3.5]nonane hemioxalate (303 mg, 0.87 mmol) in THF/EtOH (5 mL/5 mL) was added DIPEA (338 mg, 2.61 mmol). The reaction was stirred at room temperature for 48 hours. The reaction was heated to 40° C. and stirred another 4 hours. The reaction mixture was concentrated and purified by column chromatography (PE:EtOAc=7:1-4:1) to get desired product as yellow solid (230 mg, yield: 76%).

LC-MS [mobile phase: from 60% water (0.1% TFA) and 40% ACN (0.1% TFA) to 5% water (0.1% TFA) and 95% ACN (0.1% TFA) in 2 min]: Rt=0.33 min; MS Calcd: 347, MS Found: 348 [M+H]$^+$.

Description B-4

8-(6-Iodo-2-methylpyrimidin-4-yl)-3-oxa-1,8-diazaspiro[4.5]decan-2-one (D B-4)

DIPEA (496 mL, 3.0 mmol) was added to a solution of 4,6-diiodo-2-methylpyrimidine (488 mg, 1.4 mmol) and 3-oxa-1,8-diazaspiro[4.5]decan-2-one (200 mg, 1.4 mmol) in EtOH/THF (7 mL/7 mL). The reaction was stirred at rt. for 2 days. The solvent was removed and the residue was purified by column chromatography (PE:EtOAc=6:1) to gave desired product as a white solid (300 mg, yield: 57%).

LC-MS [mobile phase: from 60% water (0.1% FA) and 40% ACN (0.1% FA) to 5% water (0.1% FA) and 95% ACN (0.1% FA) in 2.0 min]: Rt=0.25 min; MS Calcd: 374, MS Found: 375 [M+H]$^+$.

Description B-5

8-(6-Iodo-2-methylpyrimidin-4-yl)-1,8-diazaspiro[4.5]decan-2-one (D B-5)

A suspension of 4,6-diiodo-2-methylpyrimidine (0.5 g, 1.45 mmol) and 1,8-diazaspiro[4.5]decan-2-one hydrochloride (275 mg, 1.45 mmol) in EtOH/THF (8 mL/8 mL) was added DIPEA (561 mg, 4.35 mmol). The mixture was stirred at rt. for 2 days. The reaction mixture was concentrated. The residue was purified by column chromatography on silica gel (DCM:MeOH=50:1) to give title compound as a yellow solid (380 mg, yield: 70%).

LC-MS [mobile phase: from 90% water (0.1% FA) and 10% ACN (0.1% FA) to 5% water (0.1% FA) and 95% ACN (0.1% FA) in 2 min]: Rt=1.01 min; MS Calcd: 372 MS Found: 373 [M+H]$^+$.

Description B-6

7-(6-Iodo-2-methylpyrimidin-4-yl)-4-oxa-7-azaspiro[2.5]octane (D B-6)

To a stirred solution of 4,6-diiodo-2-methylpyrimidine (300 mg, 0.867 mmol) and 4-oxa-7-azaspiro[2.5]octane hydrochloride (130 mg, 0.869 mmol) in THF/EtOH (5 ml/5 ml) was added DIPEA (450 mg, 3.48 mmol). The reaction was stirred at room temperature overnight. The mixture was concentrated and the residue was purified by column chromatography eluted with PE/EtOAc=7/1 to afford the desired product as pink solid (210 mg, yield: 73%). LC-MS [mobile phase: from 60% water (0.1% TFA) and 40% ACN (0.1% TFA) to 5% water (0.1% TFA) and 95% ACN (0.1% TFA) in 2.0 min]: Rt=0.61 min; MS Calcd: 331, MS Found: 332 [M+H]$^+$.

Description B-7

8-(6-Iodo-2-methylpyrimidin-4-yl)-2,8-diazaspiro[4.5]decan-1-one (D B-7)

A mixture of 1 4,6-diiodo-2-methylpyrimidine (346 mg, 1.0 mmol) and 2,8-diazaspiro[4.5]decan-1-one (272 mg, 1.2 mmol) and TEA (303 mg, 3.0 mmol) in DMSO (6 mL) was stirred at 60° C. for 4 hours. The mixture was diluted with $H_2O$ (30 mL) and extracted with EtOAc (30 mL×3). The extracts were combined and dried over $Na_2SO_4$. The organic phase was filtered and concentrated. The residue was purified by silica gel chromatography column (petroleum ether/EtOAc=10:1) to give the title compound (319 mg, 86%) as a yellow solid.

$^1$HNMR (300 MHz, $CDCl_3$): δ 6.80 (s, 1H), 6.09 (br, 1H), 4.16 (d, J=10.5 Hz, 2H), 3.40-3.29 (m, 4H), 2.44 (s, 3H), 2.12-2.07 (m, 2H), 1.96-1.88 (m, 4H).

Description B-8

Benzyl 3-oxo-1-oxa-4,8-diazaspiro[4.5]decane-8-carboxylate (D B-8)

A mixture of benzyl 4-oxopiperidine-1-carboxylate (2.33 g, 10 mmol), 2-hydroxyacetamide (825 mg, 11 mmol) and TsOH—$H_2O$ (95 mg, 0.5 mmol) in benzene (25 ml) was stirred at 120° C. under Ar for 72 hours with Dean-Stark apparatus. The reaction mixture was concentrated and the residue was purified by reverse phase HPLC (MeCN/$H_2O$=0:100-100:0) to give desired product as white solid (725 mg, yield: 25%).

LC-MS [mobile phase: from 80% water (0.1% FA) and 20% ACN (0.1% FA) to 5% water (0.1% FA) and 95% ACN (0.1% FA) in 2.0 min]: Rt=1.11 min; MS Calcd: 290, MS Found: 291 [M+H]$^+$.

Description B-9

1-Oxa-4,8-diazaspiro[4.5]decan-3-one (D B-9)

A mixture of benzyl 3-oxo-1-oxa-4,8-diazaspiro[4.5]decane-8-carboxylate (725 mg, 2.5 mmol) and Pd(OH)$_2$ (100 mg) in MeOH (50 mL) was stirred at room temperature under $H_2$ for 18 hours. The reaction mixture was filtered and the filtrate was concentrated to give crude desired product as oil (351 mg, yield: 90%).

LC-MS [mobile phase: from 90% water (0.1% FA) and 10% ACN (0.1% FA) to 5% water (0.1% FA) and 95% ACN (0.1% FA) in 2.0 min]: Rt=0.23 min; MS Calcd: 156, MS Found: 157 [M+H]$^+$.

Description B-10

8-(6-Iodo-2-methylpyrimidin-4-yl)-1-oxa-4,8-diazaspiro[4.5]decan-3-one (D B-10)

To a solution of 1-oxa-4,8-diazaspiro[4.5]decan-3-one (351 mg, 2.25 mmol) and 4,6-diiodo-2-methylpyrimidine (778 mg, 2.25 mmol) in THF/EtOH (40 ml/40 ml) was added DIPEA (887 mg, 6.88 mmol). The reaction was stirred at room temperature for 18 hours. The reaction mixture was concentrated and the residue was purified by column chromatography (eluent: PE/EtOAc=6/1 to 1/1, followed by $CH_2Cl_2$/MeOH=40/1) to get desired product as a solid (680 mg, yield: 81%).

LC-MS [mobile phase: from 70% water (0.1% FA) and 30% ACN (0.1% FA) to 5% water (0.1% FA) and 95% ACN (0.1% FA) in 2.0 min]: Rt=0.36 min; MS Calcd: 374, MS Found: 375 [M+H]$^+$.

Description B-11

6-Bromo-5-methyl-1H-indazole (D B-11)

To a solution of 5-bromo-2,4-dimethylaniline (15.0 g, 75.0 mmol) in chloroform (150 mL) was added Ac$_2$O (15.0, 150 mmol) under ice bath. KOAc (8.00 g, 82.5 mmol), 18-crown-6 (10.0 g, 37.5 mmol) and isoamyl nitrite (26.3 g, 225 mmol) were added. The mixture was refluxed for 36 hrs. The reaction mixture was concentrated and the residue was dissolved in EtOAc (500 mL). The organic solution was washed with water (100 mL), dried over $Na_2SO_4$ and concentrated. The residue was dissolved in THF (100 mL) and NaOH (4 M, 40.0 mL, 160 mmol) was added. The mixture was stirred at rt for 1 h. The solvent was removed under vacuum and the residue was partitioned between EtOAc (400 mL) and water (200 mL). The organic layer was washed with brine, dried over $Na_2SO_4$ and concentrated. The crude was purified by column chromatography (PE: EtOAc from 10:1 to 5:1) to give the title compound (5.1 g, yield 32%) as an orange solid.

$^1$H NMR (300 MHz, $CDCl_3$): δ 10.20 (br, 1H), 7.99 (s, 1H), 7.75 (s, 1H), 7.61 (s, 1H), 2.50 (s, 3H).

Description B-12

6-Bromo-5-methyl-1-(tetrahydro-2H-pyran-2-yl)-1H-indazole (D B-12)

To a solution of 6-bromo-5-methyl-1H-indazole (5.10 g, 24.2 mmol) in dry DCM (120 mL) was added DHP (4.10 g, 48.4 mmol), TsOH (0.800 g, 4.80 mmol) and Mg$_2$SO$_4$(5.0 g) at rt. The reaction mixture was heated to 35° C. and stirred for an hour. The reaction mixture was filtered and the filtrate was washed with Na$_2$CO$_3$ (10%, 100 mL), dried over Na$_2$SO$_4$ and concentrated. The crude was purified by column chromatography (PE:EtOAc from 50:1 to 20:1) to give the title compound (6.0 g, yield 84%) as an orange solid.

$^1$H NMR (300 MHz, CDCl$_3$): δ 7.90 (s, 1H), 7.84 (s, 1H), 7.55 (s, 1H), 5.63 (dd, J=9.6, 3.0 Hz, 1H), 4.05-4.00 (m, 1H), 3.78-3.70 (m, 1H), 2.58-2.44 (m, 4H), 2.20-2.02 (m, 2H), 1.78-1.65 (m, 3H).

LCMS: (mobile phase: 5-95% ACN), Rt=2.19 min in 3 min; MS Calcd: 294; MS Found: 295 [M+H]$^+$.

Description B-13 tert-butyl 4-(5-methyl-1-(tetrahydro-2H-pyran-2-yl)-1H-indazol-6-yl)-5,6-dihydropyridine-1(2H)-carboxylate (D B-13)

To a suspension of 6-bromo-5-methyl-1-(tetrahydro-2H-pyran-2-yl)-1H-indazole (5.50 g, 18.6 mmol), tert-butyl 4-(4,4,5,5-tetramethyl-1,3,2-dioxaborolan-2-yl)-5,6-dihydropyridine-1 (2H)-carboxylate (6.90 g, 22.3 mmol) and Na$_2$CO$_3$ (4.90 g, 46.5 mmol) in dioxane (150 mL) and water (130 mL) was added Pd(dppf)Cl$_2$ (658 mg, 0.900 mmol). The mixture was degassed with N$_2$ for 3 times and then stirred at 80° C. overnight. The solvent was removed under vacuum and the residue was partitioned between EtOAc (300 mL) and water (200 mL). The combined organic layers were washed with brine, dried over Na$_2$SO$_4$ and concentrated. The crude was purified by column chromatography (PE:EtOAc=10:1) to give the title compound (7.3 g, yield 99%) as a slight brown solid.

$^1$H NMR (400 MHz, CDCl$_3$): δ 7.92 (s, 1H), 7.48 (s, 1H), 7.28 (s, 1H), 5.67 (dd, J=9.6, 2.8 Hz, 1H), 5.63 (br, 1H), 4.07-4.01 (m, 3H), 3.78-3.70 (m, 1H), 3.67-3.64 (m, 2H), 2.62-2.53 (m, 1H), 2.45-2.39 (m, 2H), 2.34 (s, 3H), 2.18-2.12 (m, 1H), 2.07-2.02 (m, 1H), 1.81-1.73 (m, 2H), 1.69-1.61 (m, 1H), 1.52 (s, 9H).

Description B-14 and B-15 trans-tert-Butyl 3-hydroxy-4-(5-methyl-1-(tetrahydro-2H-pyran-2-yl)-1H-indazol-6-yl)piperidine-1-carboxylate (D B-14 and D B-15)

To a solution of tert-butyl 4-(5-methyl-1-(tetrahydro-2H-pyran-2-yl)-1H-indazol-6-yl)-5,6-dihydropyridine-1(2H)-carboxylate (33.0 g, 83.0 mmol) in dry THF (300 mL) was added BH$_3$-THF (1 M, 332 mL, 332 mmol) at 10° C. The mixture was gradually warmed to rt and stirred overnight. The reaction mixture was cooled to 0° C. and NaOH (aq, 2 M, 125 mL, 249 mmol) was added carefully. H$_2$O$_2$(30%, 87 mL, 830 mmol) was followed. The temperature was kept below 10° C. during the addition of NaOH and H$_2$O$_2$. The mixture was stirred for an hour at rt. Na$_2$SO$_3$ (10%, 100 mL) was added to the reaction mixture and stirred for 20 min. The organic layer was separated and the aqueous was extracted with EtOAc (100 mL×2). The combined organic layers were washed with brine, dried over Na$_2$SO$_4$ and evaporated. The crude was purified by column chromatography (PE:EtOAc from 3:1 to 1:1) to give trans tert-butyl 3-hydroxy-4-(5-methyl-1-(tetrahydro-2H-pyran-2-yl)-1H-indazol-6-yl)piperidine-1-carboxylate as major product (D B-14) (23 g, yield 67%) as a white solid and tert-butyl 4-(5-methyl-1-(tetrahydro-2H-pyran-2-yl)-1H-indazol-6-yl)piperidine-1-carboxylate (D B-15) as minor product (6.7 g, yield 20%) as a slight brown solid.

D B-14: $^1$H NMR (300 MHz, CDCl$_3$): δ 7.90 (s, 1H), 7.48 (s, 1H), 7.34 (s, 1H), 5.68 (dd, J=9.6 Hz, 2.7 Hz, 1H), 4.33-4.28 (m, 2H), 4.06-4.02 (m, 1H), 3.80-3.72 (m, 1H), 3.00-2.82 (m, 3H), 2.65-2.51 (m, 1H), 2.44 (s, 3H), 2.22-2.11 (m, 1H), 2.08-2.00 (m, 1H), 1.88-1.80 (m, 2H), 1.77-1.63 (m, 5H), 1.51 (s, 9H).

Description B-16

5-Methyl-6-(piperidin-4-yl)-1H-indazole hydrochloride (D B-16)

tert-Butyl 4-(5-methyl-1-(tetrahydro-2H-pyran-2-yl)-1H-indazol-6-yl)piperidine-1-carboxylate (1.0 g, 2.5 mmol) was dissolved in HCl/MeOH (5 mol/L, 10 mL). Then the mixture was stirred for 6 hrs. The mixture was concentrated under reduced pressure to afford the title compound (820 mg, yield >100%) as a light yellow solid used for next step without purification.

LC-MS: 5-95% ACN, Rt=1.13 min, MS Calcd.: 215, MS Found: 216 [M+H]$^+$.

Description B-17

5-Methyl-6-(piperidin-4-yl)-1H-indazole (D B-17)

HCl/MeOH (5M, 200 mL) was added to a solution of tert-butyl 4-(5-methyl-1-(tetrahydro-2H-pyran-2-yl)-1H-indazol-6-yl)piperidine-1-carboxylate (55.4 g, 138.8 mmol) in MeOH (150 mL). The reaction was stirred at rt overnight. The solution was concentrated and then Na$_2$CO$_3$ aq. and NaOH aq. were added until pH >12. The mixture was filtered and the solid was dried to give product as a white solid. (29.3 g, yield=98%)

LC-MS [mobile phase: from 90% water (0.1% FA) and 10% ACN (0.1% FA) to 5% water (0.1% FA) and 95% ACN (0.1% FA) in 2.0 min]: Rt=0.85 min; MS Calcd.: 215, MS Found: 216 [M+H]$^+$.

Description B-18 tert-Butyl 4-(5-methyl-1H-indazol-6-yl)piperidine-1-carboxylate (D B-18)

To a solution of 5-methyl-6-(piperidin-4-yl)-1H-indazole hydrochloride (600 mg, 2.39 mmol) in CH$_3$OH (10 mL) and H$_2$O (2 mL) was added KOH (268 mg, 4.78 mmol) and (Boc)$_2$O (781 mg, 3.58 mmol) under ice bath. The reaction mixture was stirred at rt for 2 hrs. The reaction mixture was diluted with water (50 mL) and extracted with EtOAc (50 mL×3). The combined organic layers were dried over Na$_2$SO$_4$ and concentrated. The residue was purified by column chromatograph (PE:EtOAc from 10:1 to 4:1) to give the title compound (353 mg, yield 47%) as a yellow oil.

$^1$H NMR (300 MHz, CDCl$_3$): b 10.15 (br, 1H), 7.95 (s, 1H), 7.53 (s, 1H), 7.29 (s, 1H), 4.34 (br, 2H), 2.95-2.81 (m, 3H), 2.45 (s, 3H), 1.86-1.81 (m, 2H), 1.69-1.61 (m, 2H), 1.51 (s, 9H).

Description B-19

5-Methyl-6-(1-(oxetan-3-yl)piperidin-4-yl)-1H-indazole (D B-19)

To a solution of 5-methyl-6-(piperidin-4-yl)-1H-indazole hydrochloride (820 mg of crude, 2.50 mmol) in DCE (15 mL) was added oxetan-3-one (1.80 g, 25.0 mmol). The mixture was stirred at room temperature for 40 min. Then the mixture was cooled under ice bath and NaBH$_3$CN (473 mg, 7.50 mmol) was added to the mixture. The mixture was warmed to room temperature and stirred for 2 hrs. Then the reaction mixture was poured into Na$_2$CO$_3$ aqueous solution (10%, 100 mL) and stirred for 15 min. Then the mixture was extracted with EtOAc (30 mL×3). The combined organic layers were washed with brine, dried over Na$_2$SO$_4$ and concentrated. The residue was purified by column chromatography (DCM:MeOH=40:1) to afford the title compound (473 mg, yield 70%) as a white solid $^1$H NMR (300 MHz, CDCl$_3$): δ 10.11 (br, 1H), 7.96 (s, 1H), 7.53 (s, 1H), 7.38 (s, 1H), 4.72-4.69 (m, 4H), 3.61-3.52 (m, 1H), 2.96-2.93 (m, 2H), 2.88-2.78 (m, 1H), 2.44 (s, 3H), 2.06-1.98 (m, 2H), 1.90-1.82 (m, 4H).

LC-MS [mobile phase: 5-95% Acetonitrile in 2.5 min]: Rt=1.37 min; MS Calcd: 271; MS Found: 272 [M+H]$^+$.

Description B-20

1,4-dioxaspiro[4.5]dec-7-en-8-yl trifluoromethanesulfonate (D B-20)

To a solution of 1,4-dioxaspiro[4.5]decan-8-one (10 g, 64.1 mmol) and N,N-bis(trifluoromethylsulfonyl)aniline (25.2 g, 70.5 mmol) in THF (150 mL) was added LiHMDS (70.5 mL, 70.5 mmol) drop-wise under N$_2$ at −78° C. The mixture was stirred at −78° C. for 30 min and warmed to room temperature. The reaction was quenched with aq.NH$_4$Cl (150 mL) and the mixture was extracted with EtOAc (150 mL×3). The combined organic layers were washed with brine (150 mL×3), dried over anhydrous Na$_2$SO$_4$ and concentrated to dryness. The residue was purified by silica gel chromatography (PE→PE:EtOAc=10:1) to give the product 1,4-dioxaspiro[4.5]dec-7-en-8-yltrifluoromethanesulfonate as a light yellow oil. (22.9 g, quantitative).

$^1$H NMR (400 MHz, CDCl$_3$): δ 5.66 (t, J=4.0 Hz, 1H), 3.99 (br, 4H), 2.53 (t, J=6.0 Hz, 2H), 2.41 (s, 2H), 1.91 (t, J=6.4 Hz, 2H).

Description B-21

5-Methyl-1-(tetrahydro-2H-pyran-2-yl)-6-(4,4,5,5-tetramethyl-1,3,2-dioxaborolan-2-yl)-1H-indazole (D B-21)

To a mixture of 6-bromo-5-methyl-1-(tetrahydro-2H-pyran-2-yl)-1H-indazole (5.78 g, 19.6 mmol), bis(pinacolato)diboron (9.95 g, 39.2 mmol) and CH$_3$COO$^-$ K$^+$ (7.68 g, 78.3 mmol) in dioxane (50 mL) was added Pd(PPh$_3$)$_4$(6.60 g, 5.09 mmol). The mixture was heated to 90° C. and stirred under N$_2$ overnight. The mixture was filtered and the filtrate was concentrated under vacuum. The residue was purified by silica column (PE:EtOAc from 100:1 to 60:1) to give the desired product (2.7 g, yield 41%) as a yellow solid.

$^1$H NMR (400 MHz, CDCl$_3$): δ 7.98 (s, 1H), 7.94 (s, 1H), 7.47 (s, 1H), 5.77 (dd, J=9.6, 2.8 Hz, 1H), 4.05-4.02 (m, 1H), 3.81-3.75 (m, 1H), 2.61 (s, 3H), 2.19-2.13 (m, 1H), 2.04-2.00 (m, 1H), 1.84-1.72 (m, 2H), 1.65-1.59 (m, 2H), 1.38 (s, 12H).

LC-MS: [mobile phase: from 90% water (0.02% NH$_4$OAc) and 10% ACN to 5% water (0.02% NH$_4$OAc) and 95% ACN in 4 min], Rt=2.914 min MS Calcd.: 342, MS Found: 343 [M+H]$^+$.

Description B-22

5-Methyl-6-(1,4-dioxaspiro[4.5]dec-7-en-8-yl)-1-(tetrahydro-2H-pyran-2-yl)-1H-indazole (D B-22)

To a solution of 5-methyl-1-(tetrahydro-2H-pyran-2-yl)-6-(4,4,5,5-tetramethyl-1,3,2-dioxaborolan-2-yl)-1H-indazole (3.0 g, 8.77 mmol), 1,4-dioxaspiro[4.5]dec-7-en-8-yl trifluoromethanesulfonate (3.0 g, 10.52 mmol) and K$_2$CO$_3$ (3.6 g, 26.30 mmol) in 1,4-dioxane/H$_2$O (50 mL/10 mL) was added Pd(dppf)Cl$_2$ (642 mg, 0.88 mmol). The mixture was stirred at 100° C. for 4 hrs under N$_2$. The reaction mixture was poured into water (300 mL) and the mixture was extracted with EtOAc (100 mL×3). The combined organic layers were washed with brine (100 mL), dried over anhydrous Na$_2$SO$_4$, filtered and concentrated to dryness. The residue was purified by silica gel chromatography eluted with EtOAc: Petroleum Ether=1:10 to 1:3 to give the product 5-methyl-6-(1,4-dioxaspiro[4.5]dec-7-en-8-yl)-1-(tetrahydro-2H-pyran-2-yl)-1H-indazole (2.3 g, 74.0% yield) as a white solid.

LC-MS [mobile phase: from 90% water (0.1% FA) and 10% ACN (0.1% FA) to 5% water (0.1% FA) and 95% ACN (0.1% FA) in 2.5 min]: Rt=1.30 min; MS Calcd.: 354; MS Found: 355 [M+H]$^+$.

Description B-23

5-Methyl-6-(1,4-dioxaspiro[4.5]decan-8-yl)-1-(tetrahydro-2H-pyran-2-yl)-1H-indazole (D B-23)

The mixture of 5-methyl-6-(1,4-dioxaspiro[4.5]dec-7-en-8-yl)-1-(tetrahydro-2H-pyran-2-yl)-1H-indazole (2.3 g, 6.49 mmol) and 10% Pd/C (230 mg) in MeOH (30 mL) was stirred at room temperature overnight under H$_2$. The reaction mixture was filtered and the filter cake was washed with MeOH (30 mL×3). The filtrate was concentrated to dryness to give the product 5-methyl-6-(1,4-dioxaspiro[4.5]decan-8-yl)-1-(tetrahydro-2H-pyran-2-yl)-1H-indazole (1.8 g, 77.6% yield) as a white solid.

LC-MS [mobile phase: mobile phase: from 90% water (0.1% FA) and 10% ACN (0.1% FA) to 5% water (0.1% FA) and 95% ACN (0.1% FA) in 2.5 min]: Rt=1.295 min; MS Calcd: 356, MS Found: 357 [M+H]$^+$ Description B-24

4-(5-Methyl-1H-indazol-6-yl)cyclohexanone (D B-24)

To a solution of 5-methyl-6-(1,4-dioxaspiro[4.5]decan-8-yl)-1-(tetrahydro-2H-pyran-2-yl)-1H-indazole (120 mg, 0.34 mmol) in CH$_2$Cl$_2$(10 mL) was added TFA (4 mL). The reaction mixture was stirred at room temperature overnight. The reaction was concentrated to dryness, the residue was dissolved in CH$_2$Cl$_2$(100 mL). The solution was washed with sat. NaHCO$_3$ (50 mL) and brine (50 mL), dried over anhydrous Na$_2$SO$_4$ and filtered. The filtrate was concentrated to dryness. The residue was purified by silica gel chromatography (eluted with, EtOAc: Petroleum Ether=1:10 to 1:2) to give the product 4-(5-methyl-1H-indazol-6-yl)cyclohexanone (60 mg, 77.3% yield) as a yellow oil.

$^1$H NMR (400 MHz, CDCl$_3$): δ 7.97 (s, 1H), 7.56 (s, 1H), 7.32 (s, 1H), 3.36-3.28 (m, 1H), 2.59-2.55 (m, 4H), 2.51 (s, 3H), 2.26-2.21 (m, 2H), 1.96-1.89 (m, 2H).

LC-MS [mobile phase: from 90% water (0.1% FA) and 10% ACN (0.1% FA) to 5% water (0.1% FA) and 95% ACN (0.1% FA) in 2.5 min]: Rt=1.23 min; MS Calcd.: 228; MS Found: 229 [M+H]$^+$.

Description B-25

4-(1-(6-Iodo-2-methylpyrimidin-4-yl)-5-methyl-1H-indazol-6-yl)cyclohexanone (D B-25)

The solution of 4-(5-methyl-1H-indazol-6-yl)cyclohexanone (7.0 g, 30.7 mmol), 4,6-diiodo-2-methylpyrimidine (20.0 g, 57.8 mmol) in THF (500 mL) was degassed and then CuI (2.0 g, 10.5 mmol) and K$_3$PO$_4$ (21.2 g, 100.00 mmol) were added. The mixture was degassed and N$^1$,N$^2$-dimethylethane-1,2-diamine (2 g, 22.7 mmol) was added. The reaction was stirred at RT overnight and then the reaction was diluted with EtOAc (500 mL). The mixture was washed with aq. NH$_4$Cl (200 mL×2) and brine (200 mL). The solution was dried and concentrated. The residue was purified by chromatography (silica EtOAc:DCM=0:100~5:100) to give a white solid. The solid was re-crystallized with DMF/water to give the product as a white solid (4.5 g, 33% yield).

$^1$H NMR (400 MHz, CDCl$_3$): δ 8.70 (s, 1H), 8.27 (s, 1H), 8.13 (s, 1H), 7.57 (s, 1H), 3.37 (t, J=12.0 Hz, 1H), 2.76 (s, 3H), 2.62-2.59 (m, 4H), 2.55 (s, 3H), 2.30-2.26 (m, 2H), 2.09-1.98 (m, 2H).

Description B-26 and B-27 cis-4-(1-(6-Iodo-2-methylpyrimidin-4-yl)-5-methyl-1H-indazol-6-yl)-1-methylcyclohexanol (D B-26, Rt: 2.153 min; D B-27, Rt: 2.027 min)

MeMgBr (0.4 mL, 1.2 mmol) was added to the solution of 4-(1-(6-iodo-2-methylpyrimidin-4-yl)-5-methyl-1H-indazol-6-yl)cyclohexanone (223 mg, 0.5 mmol) in THF (5 mL) at RT and the reaction was stirred at rt for 10 min. The reaction was quenched with sat. NH$_4$Cl (20 mL) and the mixture was extracted with EtOAc (2×20 mL). The solution was dried and concentrated. The residue was purified by chromatography (EtOAc:PE=1:3, 15 g of silica gel) to give two white solids.

Peak 1: 99 mg, 43% yield

LC-MS [mobile phase: from 70% water (0.1% FA) and 30% ACN (0.1% FA) to 5% water (0.1% FA) and 95% ACN (0.1% FA) in 10 min]: Rt=2.153 min; MS Calcd: 462, MS Found: 463 [M+H]$^+$.

Peak 2: 80 mg, 35% yield

LC-MS [mobile phase: from 70% water (0.1% FA) and 30% ACN (0.1% FA) to 5% water (0.1% FA) and 95% ACN (0.1% FA) in 10 min]: Rt=2.027 min; MS Calcd: 462, MS Found: 463 [M+H]$^+$.

Description B-28

5-Methyl-1-(tetrahydro-2H-pyran-2-yl)-1H-indazol-6-ol (D B-28)

To a solution of 5-methyl-1-(tetrahydro-2H-pyran-2-yl)-6-(4,4,5,5-tetramethyl-1,3,2-dioxaborolan-2-yl)-1H-indazole (2.70 g, 7.89 mmol) in THF (80 mL) and NaOH aqueous solution (1 N, 40 mL) was added H$_2$O$_2$ aqueous (37%, 4.48 g, 39.5 mmol) at 0-15° C. The mixture was diluted with sat. NaHSO$_3$ (100 mL) and extracted with EtOAc (3×50 mL). The combined organic layers were washed with brine, dried over Na$_2$SO$_4$ and concentrated under vacuum. The residue was purified by silica column (PE:EtOAc=6:1) and the crude was slurried with PE (3.5 mL) to give the desired product (1.70 g, yield 94%) as a yellow solid.

$^1$H NMR (300 MHz, CDCl$_3$): δ 7.85 (s, 1H), 7.42 (s, 1H), 6.93 (s, 1H), 5.58 (dd, J=9.6, 2.7 Hz, 1H), 5.44 (s, 1H), 4.04-3.99 (m, 1H), 3.75-3.66 (m, 1H), 2.60-2.47 (m, 1H), 2.32 (s, 3H), 2.17-2.01 (m, 2H), 1.81-1.63 (m, 3H).

LC-MS [mobile phase: from 90% water (0.02% NH$_4$OAc) and 10% ACN to 5% water (0.02% NH$_4$OAc) and 95% ACN in 4 min]: Rt=2.113 min, MS Calcd.: 232, MS Found: 233 [M+H]$^+$.

Description B-29

Tetrahydrofuran-3-yl methanesulfonate (D B-29)

To a solution of tetrahydrofuran-3-ol (500 mg, 5.68 mmol) and Et$_3$N (860 mg, 8.52 mmol) in CH$_2$Cl$_2$ (10 mL) at 0° C. was added MsCl (842 mg, 7.39 mmol) dropwise. The reaction was stirred at room temperature for 4 hours. The reaction mixture was diluted with CH$_2$Cl$_2$ (150 mL), washed with sat. NaHCO$_3$ (50 mL), dried over Na$_2$SO$_4$ and concentrated to give the title compound (700 mg, 74%) as yellow oil.

$^1$H NMR (300 MHz, CDCl$_3$): δ 5.36-5.31 (m, 1H), 4.06-3.86 (m, 4H), 3.06 (s, 3H), 2.29-2.22 (m, 2H).

Description B-30

5-Methyl-1-(tetrahydro-2H-pyran-2-yl)-6-((tetrahydrofuran-3-yl)oxy)-1H-indazole (D B-30)

A mixture of 5-methyl-1-(tetrahydro-2H-pyran-2-yl)-1H-indazol-6-ol (150 mg, 0.65 mmol), tetrahydrofuran-3-yl methanesulfonate (129 mg, 0.78 mmol) and K$_2$CO$_3$ (180 mg, 1.3 mmol) in DMF (2.0 mL) was stirred at 80° C. overnight under N$_2$ atmosphere. The reaction was diluter with water (50 mL), extracted with EtOAc (150 mL×2), washed with brine (50 mL), dried over Na$_2$SO$_4$, filtered and concentrated. The residue was purified by silica gel chromatography (Petroleum ether:EtOAc=3:1) to give the title compound (150 mg, 77%) as yellow oil.

$^1$H NMR (300 MHz, CDCl$_3$): δ 7.86 (s, 1H), 7.44 (s, 1H), 6.82 (s, 1H), 5.66 (dd, J=9.3, 2.1 Hz, 1H), 5.09-5.04 (m, 1H), 4.14-3.96 (m, 5H), 3.79-3.71 (m, 1H), 2.63-2.51 (m, 1H), 2.28 (s, 3H), 2.17-2.04 (m, 4H), 1.81-1.69 (m, 3H).

Description B-31

5-Methyl-6-((tetrahydrofuran-3-yl)oxy)-1H-indazole (D B-31)

To a solution of 5-methyl-1-(tetrahydro-2H-pyran-2-yl)-6-((tetrahydrofuran-3-yl)oxy)-1H-indazole (150 mg, 0.5 mmol) in DCM (2 mL) was added TFA (2 mL). The resulting mixture was stirred at room temperature for 5 hours. The reaction was dilutre with DCM (100 mL), washed with brine (100 mL), dried over Na$_2$SO$_4$, filtered and concentrated. The residue was purified by silica gel chromatography (Petroleum ether:EtOAc=2:3) to give the title compound (95 mg, 86%) as a yellow solid.

$^1$H NMR (300 MHz, CDCl$_3$): δ 7.92 (s, 1H), 7.48 (s, 1H), 6.74 (s, 1H), 5.02-4.96 (m, 1H), 4.13-3.93 (m, 4H), 2.29 (s, 3H), 2.27-2.20 (m, 2H).

Description B-32

8-(6-Iodo-2-methoxypyrimidin-4-yl)-2,5-dioxa-8-azaspiro[3.5]nonane (D B-32)

A mixture of 2,5-dioxa-8-azaspiro[3.5]nonane oxalate (500 mg, 1.44 mmol), 4,6-diiodo-2-methoxypyrimidine (453 mg, 1.37 mmol), TEA (415 mg, 4.11 mmol) in i-PrOH (10 mL) and DMSO (4 mL) was stirred at room temperature for 4 hours. The mixture was added H$_2$O (50 mL), extracted EtOAc with (30*3 mL). The combined organic layer was dried over Na$_2$SO$_4$, filtered and concentrated. The crude was purified by flash chromatography (petroleum ether/EtOAc=2:1) to give compound (408 mg, 82%) as a white solid.

$^1$H NMR (400 MHz, CDCl$_3$): δ 6.70 (s, 1H), 4.63 (d, J=7.2 Hz, 2H), 4.42 (d, J=7.2 Hz, 2H), 3.93 (s, 3H), 3.86 (s, 2H), 3.71 (t, J=4.8 Hz, 2H), 3.54 (s, 2H).

Description B-33 tert-Butyl 4-(1-(2-methoxy-6-(2,5-dioxa-8-azaspiro[3.5]nonan-8-yl)pyrimidin-4-yl)-5-methyl-1H-indazol-6-yl)piperidine-1-carboxylate (D B-33)

A mixture of 8-(6-iodo-2-methoxypyrimidin-4-yl)-2,5-dioxa-8-azaspiro[3.5]nonane (127 mg, 0.35 mmol), tert-butyl-4-(5-methyl-1H-indazol-6-yl) piperidine-1-carboxylate (100 mg, 0.32 mmol), CuI (30 mg, 0.15 mmol), K$_3$PO$_4$ (133 mg, 0.63 mmol) and N,N'-dimethylcyclohexane-1,2-diamine (45 mg, 0.32 mmol) in toluene (3 mL) was stirred at 100° C. for 5 hours. The mixture was added EtOAc (50 mL), washed with NH$_3$H$_2$O (30 mL×3). The organic layer was dried over Na$_2$SO$_4$, filtered and concentrated. The crude was purified by flash chromatography (petroleum ether/EtOAc=1/1) to give compound (170 mg, 97%) as a yellow oil. $^1$HNMR (400 MHz, CDCl$_3$): δ 8.71 (s, 1H), 8.09 (s, 1H), 7.53 (s, 1H), 6.91 (s, 1H), 4.64 (d, J=6.8 Hz, 2H), 4.48 (d, J=7.2 Hz, 2H), 4.31 (br, 2H), 4.12 (s, 3H), 3.96 (s, 2H), 3.76-3.74 (m, 6H), 3.69-3.67 (m, 6H), 3.63-3.61 (m, 4H), 3.58-3.56 (m, 4H), 2.48 (s, 3H).

Example A-1

6-(3-fluoro-1-(oxetan-3-yl)piperidin-4-yl)-1-(6-((R)-hexahydropyrrolo[1,2-a]pyrazin-2(1H)-yl)-2-methoxypyrimidin-4-yl)-5-methyl-1H-indazole (Single unknown isomer 1)

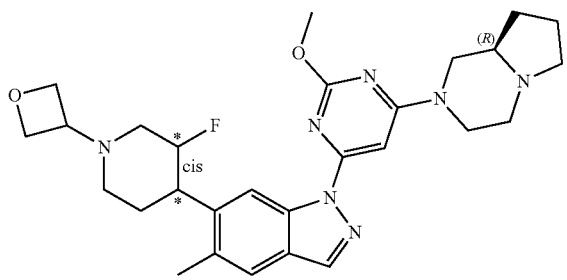

To a suspension of 6-cis-3-fluoro-1-(oxetan-3-yl)piperidin-4-yl)-5-methyl-1H-indazole (70 mg, 0.24 mmol) (peak 1), (R)-2-(6-iodo-2-methoxypyrimidin-4-yl)octahydropyrrolo[1,2-a]pyrazine (104 mg, 0.29 mmol), CuI (46 mg, 0.24 mmol) and K$_3$PO$_4$ (108 mg, 0.51 mmol) in dry toluene (5 mL) was added N,N-dimethyl-1,2-ethanediamine (43 mg, 0.48 mmol). The suspension was degassed with N$_2$ and stirred at 85° C. for 2 h. EtOAc (50 mL) was added and the resulting mixture was washed with brine (2×50 mL), dried over anhydrous Na$_2$SO$_4$ and concentrated under reduced pressure. The residue was purified by pre-HPLC (Waters 2767 Sepax Amethyst 21.2×100 mm 5 μm, Phase: MeCN/H$_2$O (0.1% TFA): 5%~95%, Flow rate: 15 mL/min, 214 nm/254 nm) to give product (24 mg, yield 19.0%) as a white solid.

$^1$H NMR (400 MHz, CDCl$_3$): δ 8.88 (s, 1H), 8.07 (s, 1H), 7.54 (s, 1H), 6.87 (s, 1H), 4.95-4.81 (m, 1H), 4.81-4.63 (m, 4H), 4.48-4.41 (br, 1H), 4.14 (s, 3H), 3.69-3.62 (m, 1H), 3.25-3.07 (m, 5H), 2.84-2.72 (m, 2H), 2.48 (s, 3H), 2.31-1.70 (m, 10H), 1.55-1.45 (m, 2H).

$^{19}$F NMR (376 MHz, CDCl$_3$): δ −184.0 (s, 1F).

LC-MS [mobile phase: from 90% water (0.1% FA) and 10% CH$_3$CN (0.1% FA) to 5% water (0.1% FA) and 95% CH$_3$CN (0.1% FA) in 10 min]: Rt=5.17 min; MS Calcd.: 521, MS Found: 522 [M+H]$^+$.

Chiral purity: Rt=8.915 min; ee %=99.5%.

Chiral method: Chiralpak AD-H 5 μm 4.6×250 mm, Phase: Hexane:Isopropanol (0.2% diethylamine)=65/35, F: 1.0 mL/min, W: 214 nm, T: 25° C.

Example A-2

6-(3-fluoro-1-(oxetan-3-yl)piperidin-4-yl)-1-(6-((S)-hexahydropyrrolo[1,2-a]pyrazin-2(1H)-yl)-2-methoxypyrimidin-4-yl)-5-methyl-1H-indazole (Single unknown isomer 2)

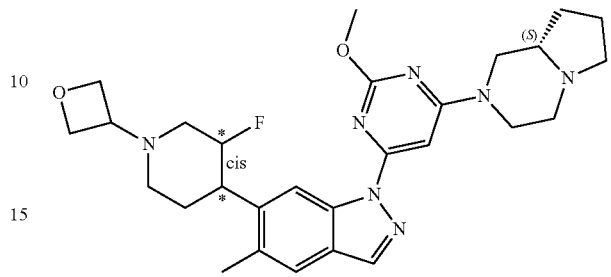

To a suspension of (cis)-6-(3-Fluoro-1-(oxetan-3-yl)piperidin-4-yl)-5-methyl-1H-indazole (70 mg, 0.24 mmol) (peak 2), (S)-2-(6-iodo-2-methoxypyrimidin-4-yl)octahydropyrrolo[1,2-a]pyrazine (104 mg, 0.29 mmol), CuI (46 mg, 0.24 mmol) and K$_3$PO$_4$ (108 mg, 0.51 mmol) in dry toluene (5 mL) was added N,N-dimethyl-1,2-ethanediamine (43 mg, 0.48 mmol). The suspension was degassed with N$_2$ and stirred at 85° C. for 2 h. EtOAc (50 mL) was added and the resulting mixture was washed with brine (2×50 mL), dried over anhydrous Na$_2$SO$_4$ and concentrated under reduced pressure. The residue was purified by pre-HPLC (Waters 2767, Sepax Amethyst 21.2×100 mm 5 μm, Phase: MeCN/H$_2$O (0.1% TFA): 5%-95%, Flow rate: 15 mL/min, 214 nm/254 nm) to give product (50 mg, yield 39.7%) as a white solid. $^1$H NMR (400 MHz, CDCl$_3$): δ 8.88 (s, 1H), 8.07 (s, 1H), 7.54 (s, 1H), 6.87 (s, 1H), 4.95-4.81 (m, 1H), 4.81-4.63 (m, 4H), 4.48-4.41 (br, 1H), 4.14 (s, 3H), 3.69-3.62 (m, 1H), 3.25-3.07 (m, 5H), 2.84-2.72 (m, 2H), 2.48 (s, 3H), 2.31-1.70 (m, 10H), 1.55-1.45 (m, 2H).

$^{19}$F NMR (376 MHz, CDCl$_3$): δ −184.0 (s, 1F).

LC-MS [mobile phase: from 90% water (0.1% FA) and 10% CH$_3$CN (0.1% FA) to 5% water (0.1% FA) and 95% CH$_3$CN (0.1% FA) in 10 min]: Rt=5.35 min; MS Calcd.: 521, MS Found: 522 [M+H]$^+$.

Chiral purity: Rt=12.450 min; ee %=99.1%.

Chiral method: Chiralpak AD-H 5 μm 4.6×250 mm, Phase: Hexane:Isopropanol (0.2% diethylamine)=65/35, F: 1.0 mL/min, W: 214 nm, T: 25° C.

Example A-3

6-(3-fluoro-1-(oxetan-3-yl)piperidin-4-yl)-1-(6-((S)-hexahydropyrrolo[1,2-a]pyrazin-2(1H)-yl)-2-methoxypyrimidin-4-yl)-5-methyl-1H-indazole (Single unknown isomer 1)

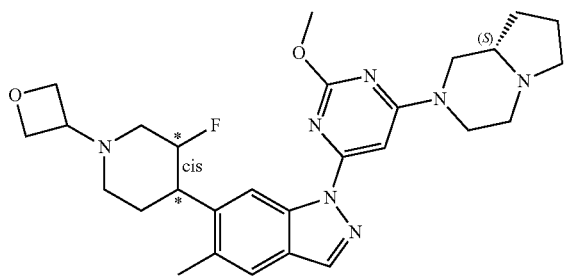

To a suspension of (cis)-6-(3-Fluoro-1-(oxetan-3-yl)piperidin-4-yl)-5-methyl-1H-indazole (70 mg, 0.24 mmol) (peak 1), (S)-2-(6-iodo-2-methoxypyrimidin-4-yl)octahydropyrrolo[1,2-a]pyrazine (104 mg, 0.29 mmol), CuI (46 mg, 0.24 mmol) and $K_3PO_4$ (108 mg, 0.51 mmol) in dry toluene (5 mL) was added N,N-dimethyl-1,2-ethanediamine (43 mg, 0.48 mmol). The suspension was degassed with $N_2$ and stirred at 85° C. for 2 h. EtOAc (50 mL) was added and the resulting mixture was washed with brine (2×50 mL), dried over anhydrous $Na_2SO_4$ and concentrated under reduced pressure. The residue was purified by pre-HPLC (Waters 2767/Qda, Waters XBridge 30×150 mm 5 μm, Phase: MeCN/$H_2O$ (0.1% TFA): 5%~95%, Flow rate: 20 mL/min, 214 nm/254 nm) to give product (70 mg, yield 55.5%) as a white solid.

$^1$H NMR (400 MHz, $CDCl_3$): δ 8.88 (s, 1H), 8.07 (s, 1H), 7.54 (s, 1H), 6.87 (s, 1H), 4.95-4.81 (m, 1H), 4.81-4.63 (m, 4H), 4.48-4.41 (br, 1H), 4.14 (s, 3H), 3.69-3.62 (m, 1H), 3.25-3.07 (m, 5H), 2.84-2.72 (m, 2H), 2.48 (s, 3H), 2.31-1.70 (m, 10H), 1.55-1.45 (m, 2H).

$^{19}$F NMR (376 MHz, $CDCl_3$): δ −184.0 (s, 1F).

LC-MS (mobile phase: from 90% water (0.1% FA) and 10% $CH_3CN$ (0.1% FA) to 5% water (0.1% FA) and 95% $CH_3CN$ (0.1% FA) in 10 min]: Rt=5.15 min; MS Calcd.: 521, MS Found: 522 [M+H]$^+$.

Chiral purity: Rt=9.697 min; ee %=99.8%.

Chiral method: Chiralpak AD-H 5 μm 4.6×250 mm, Phase: Hexane:Isopropanol (0.2% diethylamine)=65/35, F: 1.0 mL/min, W: 214 nm, T: 25° C.

Example A-4

6-(3-fluoro-1-(oxetan-3-yl)piperidin-4-yl)-1-(6-((R)-hexahydropyrrolo[1,2-a]pyrazin-2(1H)-yl)-2-methoxypyrimidin-4-yl)-5-methyl-1H-indazole (Single unknown isomer 2)

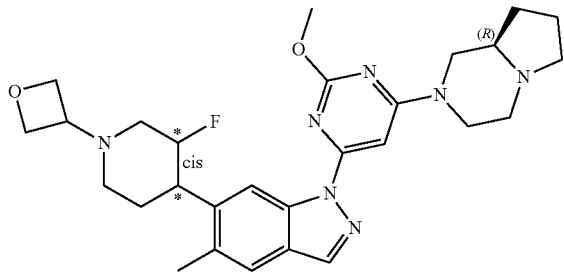

To a suspension of (cis)-6-(3-Fluoro-1-(oxetan-3-yl)piperidin-4-yl)-5-methyl-1H-indazole (70 mg, 0.24 mmol) (peak 2), (R)-2-(6-iodo-2-methoxypyrimidin-4-yl)octahydropyrrolo[1,2-a]pyrazine (104 mg, 0.29 mmol), CuI (46 mg, 0.24 mmol) and $K_3PO_4$ (108 mg, 0.51 mmol) in dry toluene (5 mL) was added N,N-dimethyl-1,2-ethanediamine (43 mg, 0.48 mmol). The suspension was degassed with $N_2$ and stirred at 85° C. for 2 h. EtOAc (50 mL) was added and the resulting mixture was washed with brine (2×50 mL), dried over anhydrous $Na_2SO_4$ and concentrated under reduced pressure. The residue was purified by pre-HPLC (Waters 2767 Sepax Amethyst 21.2×100 mm 5 μm, Phase: MeCN/$H_2O$ (0.1% TFA): 5%~95%, Flow rate: 15 mL/min, 214 nm/254 nm) to give product (70 mg, yield 55.5%) as a white solid.

$^1$H NMR (400 MHz, $CDCl_3$): δ 8.88 (s, 1H), 8.07 (s, 1H), 7.54 (s, 1H), 6.87 (s, 1H), 4.95~4.81 (m, 1H), 4.81~4.63 (m, 4H), 4.48~4.41 (br, 1H), 4.14 (s, 3H), 3.69~3.62 (m, 1H), 3.25~3.07 (m, 5H), 2.84~2.72 (m, 2H), 2.48 (s, 3H), 2.31~1.70 (m, 10H), 1.55~1.45 (m, 2H).

$^{19}$F NMR (376 MHz, $CDCl_3$): δ−184.0 (s, 1F).

LC-MS (mobile phase: from 90% water (0.1% FA) and 10% $CH_3CN$ (0.1% FA) to 5% water (0.1% FA) and 95% $CH_3CN$ (0.1% FA) in 10 min]: Rt=5.16 min; MS Calcd.: 521, MS Found: 522 [M+H]$^+$.

Chiral purity: Rt=11.898 min; ee %=99.4%.

Chiral method: Chiralpak AD-H 5 μm 4.6×250 mm, Phase: Hexane:Isopropanol (0.2% diethylamine)=65/35, F: 1.0 mL/min, W: 214 nm, T: 25° C.

Example A-5

2-(2-methoxy-6-(5-methyl-6-(tetrahydro-2H-pyran-4-yl)-1H-indazol-1-yl)pyrimidin-4-yl)hexahydropyrrolo[1,2-a]pyrazin-6(2H)-one (Enantiomer 1)

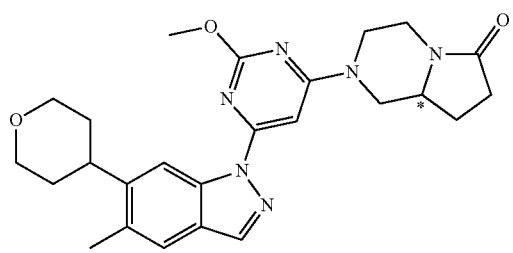 [SMILES: COc1nc(N2CCN3C(=O)CCC3C2)cc(-n2ncc3cc(C)c(C4CCOCC4)cc32)n1]

A solution of tert-butyl 2-(3-(tert-butoxy)-3-oxopropyl)-4-(2-methoxy-6-(5-methyl-6-(tetrahydro-2H-pyran-4-yl)-1H-indazol-1-yl)pyrimidin-4-yl)piperazine-1-carboxylate (85 mg, 0.13 mmol, Peak 1) in MeOH (5 mL) was added HCl/MeOH (7 M, 5 mL). The mixture was stirred at rt for 1 h. The mixture was directly concentrated in reduced pressure to give the crude solid as a mixture of the desired acid and the corresponding methyl ester (62 mg). The crude solid was treated with lithium hydroxide monohydrate (42 mg, 1.0 mmol) in THF/$H_2O$ (2 mL/2 mL) and stirred for 1 h. The reaction mixture was purified by prep-HPLC (ACN/$H_2O$, 05-95%) to give example 5 (Enantiomer 1, 7 mg, yield 11%) as a white solid.

$^1$H NMR (300 MHz, DMSO-$d_6$): δ 8.65 (s, 1H), 8.32 (s, 1H), 7.62 (s, 1H), 6.92 (s, 1H), 4.60-4.46 (m, 2H), 4.01-3.85 (m, 6H), 3.57-3.46 (m, 3H), 3.12-3.05 (m, 1H), 2.89-2.69 (m, 3H), 2.43 (s, 3H), 2.28-2.12 (m, 3H), 1.76-1.58 (m, 5H).

LC-MS [XB-$C_{18}$, ¢4.6×50 mm 5 μm; mobile phase: from 95% water (0.02% $NH_4OAc$) and 5% $CH_3CN$ to 5% water (0.02% $NH_4OAc$) and 95% $CH_3CN$ in 6.5 min]: Rt=4.180 min; MS Calcd.: 462; MS Found: 463 [M+H]$^+$.

Example A-6

2-(2-methoxy-6-(5-methyl-6-(tetrahydro-2H-pyran-4-yl)-1H-indazol-1-yl)pyrimidin-4-yl)hexahydropyrrolo[1,2-a]pyrazin-6(2H)-one (Enantiomer 2)

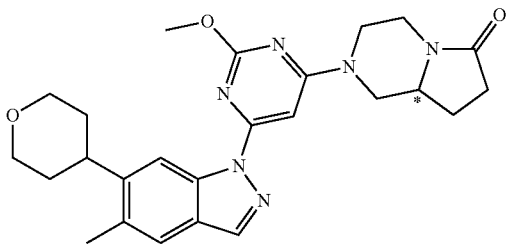 [SMILES: COc1nc(N2CCN3C(=O)CCC3C2)cc(-n2ncc3cc(C)c(C4CCOCC4)cc32)n1]

A solution of tert-butyl 2-(3-(tert-butoxy)-3-oxopropyl)-4-(2-methoxy-6-(5-methyl-6-(tetrahydro-2H-pyran-4-yl)-1H-indazol-1-yl)pyrimidin-4-yl)piperazine-1-carboxylate (80 mg, 0.13 mmol) (Peak 2) in MeOH (5 mL) was added HCl/MeOH (7 M, 5 mL). The mixture was stirred at rt for 1 h. The reaction was directly concentrated in reduced pressure to give the crude yellow solid as the mixtures of the desired acid and the corresponding methyl ester. The crude solid was treated with lithium hydroxide monohydrate (42 mg, 1.0 mmol) in THF/H$_2$O (2 mL/2 mL) and stirred for 1 h. The mixture was purified by prep-HPLC (ACN/H$_2$O, 05-95%) to give example E A-6 (Enantiomer 2, 7 mg, yield 12%) as a white solid.

$^1$H NMR (300 MHz, DMSO-d$_6$): δ 8.67 (s, 1H), 8.32 (s, 1H), 7.62 (s, 1H), 6.92 (s, 1H), 4.61-4.45 (m, 2H), 4.01-3.84 (m, 6H), 3.57-3.45 (m, 3H), 3.12-3.06 (m, 1H), 2.89-2.69 (m, 3H), 2.43 (s, 3H), 2.27-2.12 (m, 3H), 1.72-1.57 (m, 5H).

LC-MS [XB-C$_{18}$, ¢4.6×5 0 mm 5 µm; mobile phase: from 95% water (0.02% NH$_4$OAc) and 5% CH$_3$CN to 5% water (0.02% NH$_4$OAc) and 95% CH$_3$CN in 6.5 min]: Rt=4.176 min; MS Calcd.: 462; MS Found: 463 [M+H]$^+$.

Example A-7

(R)-1-(6-(hexahydropyrrolo[1,2-a]pyrazin-2(1H)-yl)-2-methylpyrimidin-4-yl)-5-methyl-6-(1-(oxetan-3-yl)piperidin-4-yl)-1H-indazole

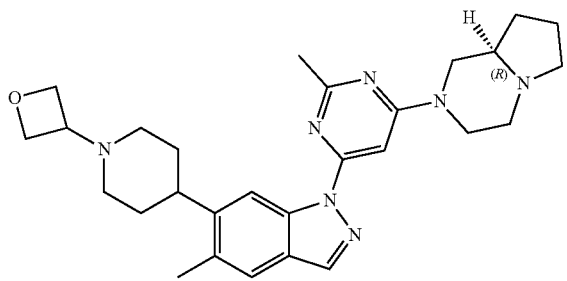

To a solution of 5-methyl-6-(1-(oxetan-3-yl)piperidin-4-yl)-1H-indazole (79 mg, 0.29 mmol) and (R)-2-(6-iodo-2-methylpyrimidin-4-yl)octahydropyrrolo[1,2-a]pyrazine (100 mg, 0.29 mmol), K$_3$PO$_4$ (123 mg, 0.58 mmol), CuI (55 mg, 0.29 mmol) in toluene(4 ml) was added N$^1$,N$^2$-dimethylethane-1,2-diamine (51 mg, 0.58 mmol) under Ar. Then the reaction mixture was stirred at 95° C. for 3 hours. TLC showed the reaction was completed. Then it was filtered and washed with DCM. The filtrate was concentrated and purified by column(PE:EtOAc=1:1 followed by DCM:MeOH=50:1-40:1-30:1-20:1) to give desired product as a white solid (94 mg, yield: 66.3%).

$^1$H NMR (400 MHz, CDCl$_3$): δ 8.78 (s, 1H), 8.05 (s, 1H), 7.50 (s, 1H), 6.95 (s, 1H), 4.71 (d, J=6.8 Hz, 4H), 4.70-4.49 (m, 2H), 3.56 (t, J=6.4 Hz, 1H), 3.17-3.15 (m, 4H), 2.98-2.95 (m, 2H), 2.85-2.78 (m, 3H), 2.65 (s, 3H), 2.45 (s, 3H), 2.31-2.22 (m, 3H), 2.17 (s, 1H), 2.06-2.04 (m, 3H), 1.84-1.80 (m, 2H), 1.56-1.52 (m, 2H).

LC-MS [mobile phase: from 90% water (0.1% TFA) and 10% CH$_3$CN (0.1% TFA) to 5% water (0.1% TFA) and 95% CH$_3$CN (0.1% TFA) in 10 min]: Rt=4.60 min; MS Calcd: 487.31, MS Found: 488.0 [M+H]$^+$.

Example A-8

(S)-1-(6-(hexahydropyrrolo[1,2-a]pyrazin-2(1H)-yl)-2-methylpyrimidin-4-yl)-5-methyl-6-(1-(oxetan-3-yl)piperidin-4-yl)-1H-indazole

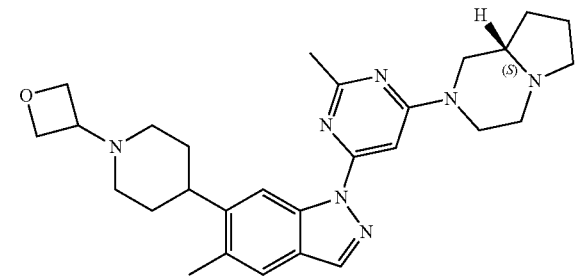

To a solution of 5-methyl-6-(1-(oxetan-3-yl)piperidin-4-yl)-1H-indazole (71 mg, 0.26 mmol) and (S)-2-(6-iodo-2-methylpyrimidin-4-yl)octahydropyrrolo[1,2-a]pyrazine (90 mg, 0.26 mmol), K$_3$PO$_4$ (110 mg, 0.52 mmol), CuI (50 mg, 0.26 mmol) in toluene (2 ml) was added N$^1$,N$^2$-dimethylethane-1,2-diamine (46 mg, 0.52 mmol) under Ar. Then the reaction was stirred at 95° C. for 4 hours. TLC showed the reaction was completed. Then it was filtered and washed with DCM. The filtrate was concentrated and purified by column(DCM:MeOH=50:1-40:1-30:1-20:1) to get a yellow solid. (20 mg, Yield: 15.7%).

$^1$H NMR (400 MHz, CDCl$_3$): δ 8.78 (br, 1H), 8.07 (s, 1H), 7.50 (s, 1H), 6.95 (s, 1H), 4.71 (d, J=6.8 Hz, 4H), 4.70-4.49 (m, 2H), 3.56 (t, J=6.4 Hz, 1H), 3.17-3.15 (m, 2H), 2.98-2.95 (m, 2H), 2.85-2.78 (m, 2H), 2.65 (s, 3H), 2.45 (s, 3H), 2.31-2.22 (m, 2H), 2.07-1.94 (m, 8H), 1.70-1.65 (m, 1H), 1.70-1.50 (m, 3H).

LC-MS [mobile phase: from 90% water (0.1% TFA) and 10% CH$_3$CN (0.1% TFA) to 5% water (0.1% TFA) and 95% CH$_3$CN (0.1% TFA) in 10 min]: Rt=4.58 min; MS Calcd: 487, MS Found: 488 [M+H]$^+$.

Example A-9

Step 1

3-(2-methyl-6-(5-methyl-6-(piperidin-4-yl)-1H-indazol-1-yl)pyrimidin-4-yl)-3-azabicyclo[3.1.0]hexan-1-ol 2,2,2-trifluoroacetate

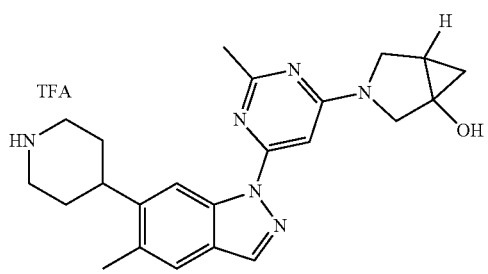 [SMILES: Cc1nc(N2CC3CC3(O)C2)cc(-n2ncc3cc(C)c(C4CCNCC4)cc32)n1]

To a solution of tert-butyl 4-(1-(6-(1-hydroxy-3-azabicyclo[3.1.0]hexan-3-yl)-2-methylpyrimidin-4-yl)-5-methyl-1H-indazol-6-yl)piperidine-1-carboxylate (70 mg, 0.13 mmol) in CH$_2$Cl$_2$ (2 mL) was added TFA (1 mL) at 0° C. After added the mixture was warmed to rt and stirred for 2 hrs. The mixture was concentrated to give the title compound (35 mg, yield >100%) which was used for next step directly.

LCMS (mobile phase: 5-95% Acetonitrile in 4 min): Rt=2.565 min; MS Calcd: 404; MS Found: 405 [M+H]$^+$.

Step 2

3-(2-Methyl-6-(5-methyl-6-(1-(oxetan-3-yl)piperidin-4-yl)-1H-indazol-1-yl)pyrimidin-4-yl)-3-azabicyclo[3.1.0]hexan-1-ol

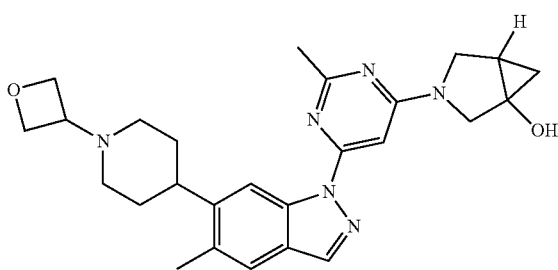 [SMILES: Cc1nc(N2CC3CC3(O)C2)cc(-n2ncc3cc(C)c(C4CCN(C5COC5)CC4)cc32)n1]

To a solution of 3-(2-methyl-6-(5-methyl-6-(piperidin-4-yl)-1H-indazol-1-yl)pyrimidin-4-yl)-3-azabicyclo[3.1.0]hexan-1-ol 2,2,2-trifluoroacetate (70 mg, 0.13 mmol) in ClCH$_2$CH$_2$Cl (4 mL) and methanol (0.5 mL) was added oxetan-3-one (13 mg, 0.18 mmol) at rt. The solution was stirred at rt for 30 min and then NaBH$_3$CN (22 mg, 0.35 mmol) was added. The resulting mixture was stirred at rt overnight. The mixture was poured into sat. Na$_2$CO$_3$ solution (5 mL). The desired was extracted with ethyl acetate (5 mL×3). The combined organic layers were washed with brine (5 mL), dried over Na$_2$SO$_4$ and concentrated. The residue was purified by prep. TLC (CH$_2$Cl$_2$:methanol=30:1) to give the title compound (4.7 mg) as a white solid.

$^1$H NMR (300 MHz, CDCl$_3$): δ 8.81 (s, 1H), 8.04 (s, 1H), 7.49 (s, 1H), 6.65 (s, 1H), 4.72-4.70 (m, 4H), 3.67-3.55 (m, 4H), 2.99-2.96 (m, 2H), 2.87-2.83 (m, 1H), 2.63 (s, 3H), 2.45 (s, 3H), 2.08-1.94 (m, 7H), 1.88-1.79 (m, 1H), 1.30-1.27 (m, 1H), 0.72-0.68 (m, 1H).

LC-MS [mobile phase: from 95% water (0.1% TFA) and 5% CH$_3$CN to 5% water (0.1% TFA) and 95% CH$_3$CN in 6.5 min]: Rt=2.992 min; MS Calcd.: 460; MS Found: 461 [M+H]$^+$.

Examples A-10 and A-11

Synthesis of cis-5-(2-methyl-6-(5-methyl-6-(1-(oxetan-3-yl)piperidin-4-yl)-1H-indazol-1-yl)pyrimidin-4-yl)hexahydro-2H-furo[2,3-c]pyrrole (Peak 1, Single unknown enantiomer, Rt=5.893 min; Peak 2, Single unknown enantiomer, Rt=7.095 min)

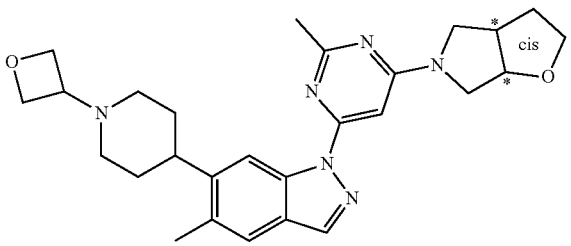 [SMILES: Cc1nc(N2CC3CCOC3C2)cc(-n2ncc3cc(C)c(C4CCN(C5COC5)CC4)cc32)n1]

N,N'-dimethylethylenediamine (80 mg, 0.90 mmol) was added to a mixture of cis-5-(6-iodo-2-methylpyrimidin-4-yl)hexahydro-2H-furo[2,3-c]pyrrole (183 mg, 0.553 mmol), 5-methyl-6-(1-(oxetan-3-yl)piperidin-4-yl)-1H-indazole (150 mg, 0.553 mmol), CuI (86 mg, 0.453 mmol) and K$_3$PO$_4$ (289 mg, 1.360 mmol) in toluene (4 ml) under Ar. The reaction was stirred at 100° C. for 3 h. The cooled reaction mixture was filtered and the filtrate was concentrated. The residue was purified by column chromatography (eluent: CH$_2$Cl$_2$:MeOH=20:1) to afford the desired product as a white solid (200 mg, yield: 76%).

$^1$H NMR (400 MHz, CDCl$_3$) δ 8.83 (s, 1H), 8.05 (s, 1H), 7.49 (s, 1H), 6.71 (s, 1H), 4.71 (d, J=6.8 Hz, 4H), 4.65 (t, J=5.2 Hz, 1H), 4.02 (q, J=7.6 Hz, 1H), 3.93-3.83 (m, 3H), 3.66 (dd, J=12.4, 4.8 Hz, 1H), 3.56 (t, J=5.2 Hz, 1H), 3.46-3.42 (m, 1H), 3.06-3.03 (m, 1H), 2.97 (d, J=9.2 Hz, 2H), 2.85-2.82 (m, 1H), 2.65 (s, 3H), 2.45 (s, 3H), 2.20-2.17 (m, 1H), 2.03-1.94 (m, 7H).

LC-MS [mobile phase: from 90% water (0.1% TFA) and 10% CH$_3$CN (0.1% TFA) to 5% water (0.1% TFA) and 95% CH$_3$CN (0.1% TFA) in 12.0 min]: Rt=5.01 min; MS Calcd: 474, MS Found: 475 [M+H]$^+$.

Chiral separation of racemic cis-5-(2-methyl-6-(5-methyl-6-(1-(oxetan-3-yl)piperidin-4-yl)-1H-indazol-1-yl)pyrimidin-4-yl)hexahydro-2H-furo[2,3-c] (202 mg) by chiral prep-HPLC (Method: Column: AD-H; Column size: 0.46 cm I.D.×15 cm L; Mobile phase: CO$_2$:ETOH (0.1% NH$_3$.H$_2$O)=60:40; Flow rate: 0.5 ml/min; Wave length: UV 254 nm; Temperature: 25° C.; Sample solution in EtOH) afforded peak 1 as a pale yellow solid (Rt=5.893 min, 79.9 mg, yield: 39%) and peak 2 as a pale yellow solid (Rt=7.095 min, 90.8 mg, yield: 44%)

Example A-10

Peak 1: $^1$H NMR (400 MHz, CDCl$_3$) δ 8.83 (s, 1H), 8.05 (s, 1H), 7.49 (s, 1H), 6.71 (s, 1H), 4.71 (d, J=6.4 Hz, 4H), 4.65 (t, J=5.2 Hz, 1H), 4.02 (q, J=7.6 Hz, 1H), 3.93-3.88 (m, 3H), 3.66 (dd, J=12.4, 4.4 Hz, 1H), 3.56 (t, J=6.6 Hz, 1H), 3.46-3.42 (m, 1H), 3.06-3.03 (m, 1H), 2.97 (d, J=11.8 Hz, 2H), 2.85-2.81 (m, 1H), 2.65 (s, 3H), 2.45 (s, 3H), 2.20-2.17 (m, 1H), 2.04-1.94 (m, 7H).

LC-MS [mobile phase: from 90% water (0.1% TFA) and 10% $CH_3CN$ (0.1% TFA) to 5% water (0.1% TFA) and 95% $CH_3CN$ (0.1% TFA) in 12.0 min]: Rt=4.88 min; MS Calcd: 474, MS Found: 475 $[M+H]^+$.

Example A-11

Peak 2 $^1H$ NMR (400 MHz, $CDCl_3$) δ 8.83 (s, 1H), 8.05 (s, 1H), 7.49 (s, 1H), 6.71 (s, 1H), 4.71 (d, J=6.8 Hz, 4H), 4.65 (t, J=5.6 Hz, 1H), 4.02 (q, J=7.6 Hz, 1H), 3.93-3.86 (m, 3H), 3.66 (dd, J=12.4, 4.4 Hz, 1H), 3.56 (t, J=6.6 Hz, 1H), 3.46-3.42 (m, 1H), 3.06-3.03 (m, 1H), 2.97 (d, J=11.2 Hz, 2H), 2.85-2.81 (m, 1H), 2.65 (s, 3H), 2.45 (s, 3H), 2.20-2.17 (m, 1H), 2.04-1.94 (m, 7H).

LC-MS [mobile phase: from 90% water (0.1% TFA) and 10% $CH_3CN$ (0.1% TFA) to 5% water (0.1% TFA) and 95% $CH_3CN$ (0.1% TFA) in 12.0 min]: Rt=4.96 min; MS Calcd: 474, MS Found: 475 $[M+H]^+$.

Examples A-12 and A-13

8-(2-methoxy-6-(5-methyl-6-(1-(oxetan-3-yl)piperidin-4-yl)-1H-indazol-1-yl)-pyrimidin-4-yl)octahydropyrazino[2,1-c][1,4]oxazine (Single unknown enantiomer 1, Rt=2.471 min; Single unknown enantiomer 2, Rt=2.873 min)

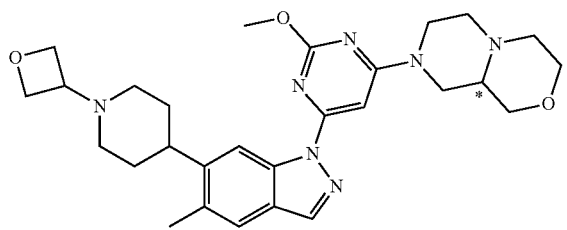 [SMILES: COc1nc(N2CCN3CCOCC3C2)cc(-n2ncc3cc(C)c(C4CCN(C5COC5)CC4)cc32)n1]

To a suspension of 5-methyl-6-(1-(oxetan-3-yl)piperidin-4-yl)-1H-indazole (115 mg, 1.43 mmol), 8-(6-iodo-2-methoxypyrimidin-4-yl)octahydropyrazino[2,1-c][1,4]oxazine (160 mg, 0.63 mmol), CuI (81 mg, 0.43 mmol) and $K_3PO_4$ (181 mg, 0.85 mmol) in toluene/THF (10 mL/2 mL) was added DMEDA (75 mg, 0.85 mmol). The resulting mixture was degassed with $N_2$ three times. The reaction was stirred at 80° C. for 2 hour. EtOAc (40 mL) was added and the resulting mixture was washed with sat. $NH_4Cl$ (30 mL) and brine (30 mL). The organic solution was dried over anhydrous $Na_2SO_4$ and concentrated. The residue was purified by prep-HPLC (Gilson 281, YMC-Actus Triart Prep $C_{18}$-S 250×20 mm 10 μm, Mobile Phase: MeCN/$H_2O$ (0.05% TFA): 15-95%, Flow rate: 20 ml/min, 254 nm) to give the product as a pale yellow solid (200 mg, yield: 91%).

LC-MS [mobile phase: from 90% water (0.1% FA) and 10% $CH_3CN$ (0.1% FA) to 5% water (0.1% FA) and 95% $CH_3CN$ (0.1% FA) in 2.0 min]: Rt=1.13 min; MS Calcd.: 519, MS Found: 520 $[M+H]^+$.

The compound 8-(2-methoxy-6-(5-methyl-6-(1-(oxetan-3-yl)piperidin-4-yl)-1H-indazol-1-yl) pyrimidin-4-yl)octahydropyrazino[2,1-c][1,4]oxazine (200 mg, 0.38 mmol) was purified by chiral prep-HPLC (AD-H, 0.46 cm I.D.×15 cm L, Mobile phase: $CO_2$:EtOH (0.1% $NH_3.H_2O$)=60:40, Flow rate: 0.5 mL/min, Wave length: UV 254 nm, Temperature: 25° C.) to give product as two pale yellow solids.

Example A-12 (Single unknown enantiomer 1, Rt=2.471 min)

(1.4 mg, yield: 1%).

$^1H$ NMR (400 MHz, $CDCl_3$): δ 8.76 (s, 1H), 8.07 (s, 1H), 7.51 (s, 1H), 6.84 (s, 1H), 4.70 (d, J=6.4 Hz, 4H), 4.40-4.27 (m, 2H), 4.15 (s, 3H), 3.89~3.81 (m, 2H), 3.76~3.71 (m, 1H), 3.59~3.52 (m, 1H), 3.32 (t, J=10.8 Hz, 1H), 3.18 (t, J=11.6 Hz, 1H), 2.93 (d, J=10.4 Hz, 2H), 2.87~2.80 (m, 2H), 2.74 (d, J=11.2 Hz, 1H), 2.68~2.61 (m, 1H), 2.45 (s, 3H), 2.44~2.27 (m, 3H), 2.05~1.99 (m, 2H), 1.92~1.83 (m, 4H).

LC-MS [mobile phase: from 90% water (0.1% FA) and 10% $CH_3CN$ (0.1% FA) to 5% water (0.1% FA) and 95% $CH_3CN$ (0.1% FA) in 9 min]: Rt=3.79 min; MS Calcd: 519, MS Found: 520 $[M+H]^+$.

Chiral HPLC [AD 4.6×250 mm, 5 μm (Daicel) (CA-HPLC-023), Phase: Hexane/EtOH (0.2% DEA)=60/40, flow rate: 0.5 mL/min, temperature: 35° C.]: Rt: 2.471 min, ee: 100%

Example A-13 (Single Unknown Enantiomer 1, Rt=2.873 Min)

(109.3 mg, yield: 55%)

$^1H$ NMR (400 MHz, $CDCl_3$): δ 8.76 (s, 1H), 8.06 (s, 1H), 7.51 (s, 1H), 6.84 (s, 1H), 4.70 (d, J=6.4 Hz, 4H), 4.40-4.27 (m, 2H), 4.15 (s, 3H), 3.90-3.81 (m, 2H), 3.74 (t, J=10.0 Hz, 1H), 3.58~3.51 (m, 1H), 3.32 (t, J=10.4 Hz, 1H), 3.18 (t, J=12.0 Hz, 1H), 2.94 (d, J=10.8 Hz, 2H), 2.87~2.80 (m, 2H), 2.73 (d, J=11.6 Hz, 1H), 2.65 (t, J=11.2 Hz, 1H), 2.45 (s, 3H), 2.42~2.27 (m, 3H), 2.04~1.98 (m, 2H), 1.91~1.85 (m, 4H).

LC-MS [mobile phase: from 90% water (0.1% FA) and 10% $CH_3CN$ (0.1% FA) to 5% water (0.1% FA) and 95% $CH_3CN$ (0.1% FA) in 9 min]: Rt=3.77 min; MS Calcd: 519, MS Found: 520 $[M+H]^+$.

Chiral HPLC [AD 4.6×250 mm, 5 μm (Daicel) (CA-HPLC-023), Phase: Hexane/EtOH (0.2% DEA)=60/40, flow rate: 0.5 mL/min, temperature: 35° C.]: Rt: 2.873 min, ee: 99.71%

Example B-1

8-(2-Methyl-6-(5-methyl-6-(1-(oxetan-3-yl)piperidin-4-yl)-1H-indazol-1-yl)pyrimidin-4-yl)-1-oxa-4,8-diazaspiro[4.5]decan-3-one

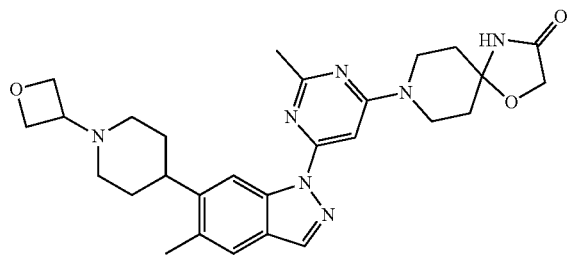

To a mixture of 5-methyl-6-(1-(oxetan-3-yl)piperidin-4-yl)-1H-indazole (217 mg, 0.8 mmol), 8-(6-iodo-2-methylpyrimidin-4-yl)-1-oxa-4,8-diazaspiro[4.5]decan-3-one (300 mg, 0.8 mmol), K$_3$PO$_4$ (339 mg, 1.6 mmol) and CuI (152 mg, 0.8 mmol) in toluene (8 ml) under Ar was added N,N'-dimethylethylenediamine (141 mg, 1.6 mmol). The reaction was stirred at 100° C. for 3 hours. TLC showed reaction was complete. The reaction mixture was filtered and the filter cake was washed with CH$_2$Cl$_2$. The combined filtrate was concentrated and the residue was purified by column chromatography (eluent: PE/EtOAc=1/1 to 0/1, followed by CH$_2$Cl$_2$/MeOH=30/1 to 25/1) afforded pure desired product as yellow solid (30 mg, yield: 7%).

$^1$H NMR (400 MHz, CDCl$_3$) δ 8.81 (s, 1H), 8.05 (s, 1H), 7.50 (s, 1H), 7.00 (s, 1H), 6.66 (s, 1H), 4.71 (d, J=6.4 Hz, 4H), 4.32 (s, 2H), 4.32-4.25 (m, 2H), 3.58-3.48 (m, 3H), 2.97 (d, J=10.4 Hz, 2H), 2.84 (br, 1H), 2.64 (s, 3H), 2.45 (s, 3H), 2.05-1.93 (m, 8H), 1.86-1.79 (m, 2H).

LC-MS [mobile phase: from 60% water (0.1% NH$_4$OH) and 40% ACN (0.1% NH$_4$OH) to 5% water (0.1% NH$_4$OH) and 95% ACN (0.1% NH$_4$OH) in 10.0 min]: Rt=3.61 min; MS Calcd: 517, MS Found: 518 [M+H]$^+$.

Example B-2

8-(2-Methyl-6-(5-methyl-6-(1-(oxetan-3-yl)piperidin-4-yl)-1H-indazol-1-yl)pyrimidin-4-yl)-3-oxa-1,8-diazaspiro[4.5]decan-2-one

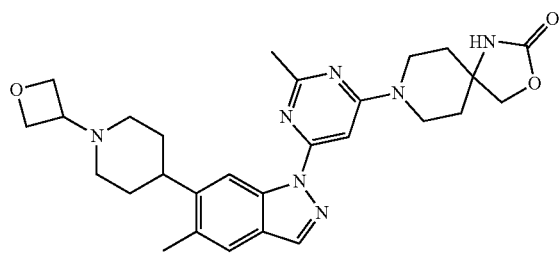

DMEDA (65 mg, 0.74 mmol) was added to a solution of 8-(6-iodo-2-methylpyrimidin-4-yl)-3-oxa-1,8-diazaspiro[4.5]decan-2-one (118 mg, 0.31 mmol), 5-methyl-6-(1-(oxetan-3-yl)piperidin-4-yl)-1H-indazole (100 mg, 0.37 mmol), CuI (70 mg, 0.37 mmol) and K$_3$PO$_4$ (156 mg, 0.74 mmol) in toluene (8 mL) under Ar. The reaction was stirred at 100° C. for 3.5 h. The mixture was filtered and purified by column chromatography (DCM:MeOH=50:1) to gave product as a white solid (50 mg, yield: 31%).

LC-MS [mobile phase: from 90% water (0.1% FA) and 10% ACN (0.1% FA) to 5% water (0.1% FA) and 95% ACN (0.1% FA) in 10.0 min]: Rt=5.612 min; MS Calcd: 517, MS Found: 518 [M+H]$^+$.

$^1$H NMR (400 MHz, CDCl$_3$) δ 8.81 (s, 1H), 8.05 (s, 1H), 7.50 (s, 1H), 6.99 (s, 1H), 6.31 (s, 1H), 4.71 (d, J=6.5 Hz, 4H), 4.22 (s, 2H), 3.96-3.79 (m, 2H), 3.79-3.63 (m, 2H), 3.64-3.45 (m, 1H), 2.97 (d, J=10.3 Hz, 2H), 2.89-2.77 (m, 1H), 2.64 (s, 3H), 2.45 (s, 3H), 2.07-1.82 (m, 10H).

Example B-3

2-(6-(6-(cis-4-Hydroxy-4-methylcyclohexyl)-5-methyl-1H-indazol-1-yl)-2-methylpyrimidin-4-yl)-2,6-diazaspiro[3.4]octan-7-one (Rt=6.47 min)

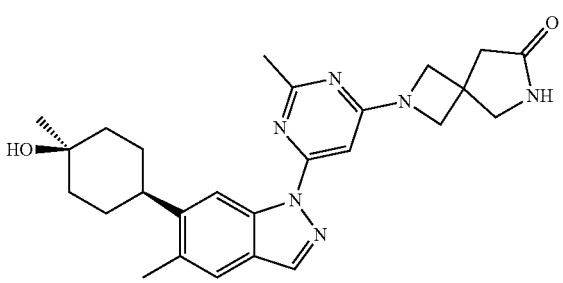 [SMILES: Cc1nc(N2CC3(CNC(=O)C3)C2)cc(-n2ncc3cc(C)c([C@H]4CC[C@@](C)(O)CC4)cc32)n1]

A mixture of cis-4-(1-(6-iodo-2-methylpyrimidin-4-yl)-5-methyl-1H-indazol-6-yl)-1-methylcyclohexanol (70 mg, 0.15 mmol), 2,6-diazaspiro[3.4]octan-7-one hydrochloride (122 mg, 0.75 mmol) and DIEA (194 mg, 1.50 mmol) in NMP (3 mL) was stirred at 30° C. overnight, then poured into water (20 mL) and extracted with EtOAc (3×20 mL). The combined organic phase was washed with brine (3×50 mL), dried over Na$_2$SO$_4$ and concentrated to obtain the crude. The crude was purified by prep-HPLC to give product as a white solid (35 mg, yield: 50%)

$^1$H NMR (400 MHz, CDCl$_3$): δ 8.851 (s, 1H), 8.061 (s, 1H), 7.492 (s, 1H), 6.615 (s, 1H), 6.218 (s, 1H), 4.180-4.250 (m, 4H), 2.781 (s, 1H), 2.629 (s, 3H), 2.454 (s, 6H), 1.987-1.924 (t, 2H), 1.866-1.764 (m, 4H), 1.661-1.603 (t, 4H), 1.324 (s, 3H).

LC-MS [mobile phase: from 70% water (0.1% TFA) and 30% ACN (0.1% TFA) to 95% water (0.1% TFA) and 5% ACN (0.1% TFA) in 10 min]: Rt=6.47 min; MS Calcd.: 460, MS Found: 461 [M+H]$^+$.

Prep-HPLC method:

Waters 2767/Qda, Waters XBridge 30×150 mm 5 μm 20 ml/min A: H$_2$O, B: ACN

| Time | B % |
| --- | --- |
| 0 | 20 |
| 2 | 45 |
| 12 | 75 |
| 12.5 | 95 |
| 15 | 95 |
| 15.2 | 10 |
| 18 | 10 |

Example B-4

8-(2-Methyl-6-(5-methyl-6-(1-(oxetan-3-yl)piperidin-4-yl)-1H-indazol-1-yl)pyrimidin-4-yl)-2,5-dioxa-8-azaspiro[3.5]nonane

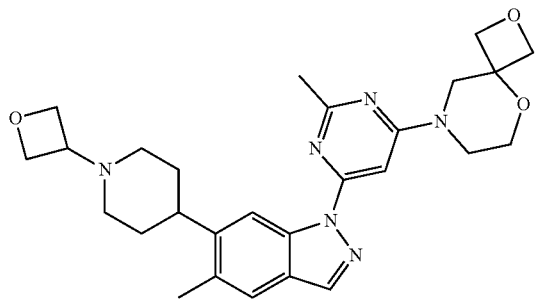 [SMILES: Cc1nc(N2CCOC3(COC3)C2)cc(-n2ncc3cc(C)c(C4CCN(C5COC5)CC4)cc32)n1]

To a solution of 5-methyl-6-(1-(oxetan-3-yl)piperidin-4-yl)-1H-indazole (179 mg, 0.66 mmol) and 8-(6-iodo-2-methylpyrimidin-4-yl)-2,5-dioxa-8-azaspiro[3.5]nonane (230 mg, 0.66 mmol), $K_3PO_4$ (280 mg, 1.32 mmol), CuI (126 mg, 0.66 mmol) in toluene (4 ml) was added $N^1,N^2$-dimethylethane-1,2-diamine (116 mg, 1.32 mmol) under Ar. The reaction was stirred at 95° C. for 3.5 hours. TLC showed the reaction was complete. The reaction mixture was filtered and washed with DCM. The filtrate was concentrated and purified by column chromatography (PE:EtOAc=1:1 followed by DCM:MeOH=50:1) to get desired product as white solid (240 mg, yield: 74%).

$^1$H NMR (400 MHz, $CDCl_3$) δ 8.82 (s, 1H), 8.07 (s, 1H), 7.51 (s, 1H), 7.02 (s, 1H), 4.71 (d, J=6.4 Hz, 4H), 4.65 (d, J=6.8 Hz, 2H), 4.49 (d, J=7.2 Hz, 2H), 3.98 (s, 2H), 3.76 (t, J=4.6 Hz, 2H), 3.67 (d, J=4.8 Hz, 2H), 3.58-3.55 (m, 1H), 2.98 (d, J=10.4 Hz, 2H), 2.90-2.85 (m, 1H), 2.67 (s, 3H), 2.46 (s, 3H), 2.05-1.84 (m, 6H).

LC-MS [mobile phase: from 80% water (0.1% TFA) and 20% ACN (0.1% TFA) to 5% water (0.1% TFA) and 95% ACN (0.1% TFA) in 10 min]: Rt=4.85 min; MS Calcd: 490, MS Found: 491 [M+H]$^+$.

Example B-5

8-(2-Methyl-6-(5-methyl-6-(1-(oxetan-3-yl)piperidin-4-yl)-1H-indazol-1-yl)pyrimidin-4-yl)-1,8-diazaspiro[4.5]decan-2-one trifluoroacetate

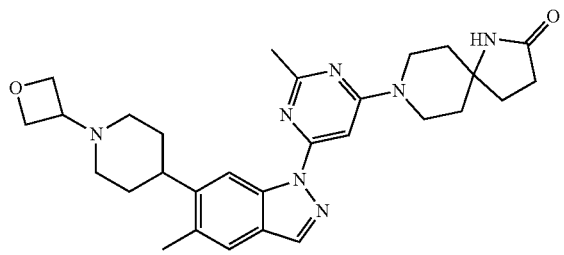 [SMILES: Cc1nc(N2CCC3(CCC(=O)N3)CC2)cc(-n2ncc3cc(C)c(C4CCN(C5COC5)CC4)cc32)n1]

A mixture of 8-(6-iodo-2-methylpyrimidin-4-yl)-1,8-diazaspiro[4.5]decan-2-one (223 mg, 0.6 mmol) and 5-methyl-6-(1-(oxetan-3-yl)piperidin-4-yl)-1H-indazole (164 mg, 0.6 mmol) in toluene (10 mL) was added $K_3PO_4$ (254 mg, 1.2 mmol), CuI (114 mg, 0.6 mmol) and $N^1,N^2$-dimethylethane-1,2-diamine (53 mg, 0.6 mmol). The mixture was degassed and protected with Ar then heated at 100° C. for 5 h. the reaction mixture was filtered and the filtrate was concentrated. The residue was purified by prep-HPLC to give title compound as a yellow solid as a TFA salt (50 mg)

$^1$H NMR (400 MHz, DMSO-d6): δ 10.60 (br, 1H), 8.73 (s, 1H), 8.35 (s, 1H), 8.09 (s, 1H), 7.68 (d J=8.8 Hz, 1H), 7.02 (s, 1H), 4.86-4.78 (m, 4H), 4.34-4.32 (m, 1H), 3.82-3.57 (m, 6H), 3.24-3.10 (m, 3H), 2.64 (s, 3H), 2.47 (s, 3H), 2.27-1.63 (m, 12H).

LC-MS [mobile phase: from 80% water (0.1% FA) and 20% ACN (0.1% FA) to 5% water (0.1% FA) and 95% ACN (0.1% FA) in 10 min]: Rt=4.44 min; MS Calcd: 515, MS Found: 516 [M+H]$^+$.

Instrument: Waters 2767/Qda
Column: Waters sunfire C18 20×250 mm 10 μm, Rate: 30 ml/min
Wavelength: 214 nm/254 nm, Trigger: 254 nm
Mobile Phase A: $H_2$ (0.1% TFA), Mobile Phase B: ACN
Gradient Method:

| Time | B % |
| --- | --- |
| 0 | 15 |
| 10 | 30 |
| 10.2 | 95 |
| 13.2 | 95 |
| 13.5 | 10 |
| 15 | 10 |

Example B-6

8-(2-Methyl-6-(5-methyl-6-(1-(oxetan-3-yl)piperidin-4-yl)-1H-indazol-1-yl)pyrimidin-4-yl)-2,8-diazaspiro[4.5]decan-1-one

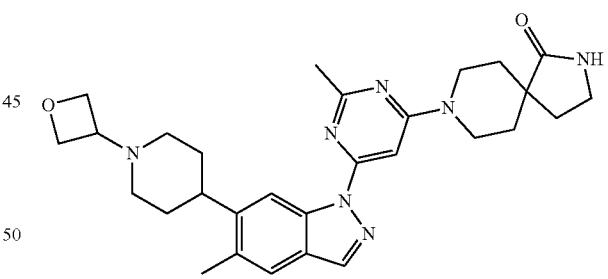

To a solution of 8-(6-iodo-2-methylpyrimidin-4-yl)-2,8-diazaspiro[4.5]decan-1-one (140 mg, 0.376 mmol) in toluene (15 mL) were added 5-methyl-6-(1-(oxetan-3-yl)piperidin-4-yl)-1H-indazole (103 mg, 0.376 mmol), CuI (108 mg, 0.57 mmol), N,N'-dimethylethylenediamine (67 mg, 0.75 mmol) and $K_3PO_4$ (160 mg, 0.75 mmol). The reaction mixture was stirred at 100° C. for 3 h with $N_2$ protection. The reaction mixture was diluted with EtOAc (60 mL) and then filtered. The filtrate was concentrated under vacuum to give a residue. The residue was purified by column chromatography (EtOAc:MeOH=5:1~2:1) to give product (120 mg). The product was further purified by prep-TLC (EtOAc:MeOH=3:1) to give product (57 mg) as a yellow solid.

$^1$H NMR (400 MHz, $CDCl_3$) δ 8.74 (s, 1H), 8.30 (s, 1H), 7.62 (s, 2H), 7.00 (s, 1H), 4.58-4.30 (m, 6H), 3.48-3.44 (m,

1H), 3.25-3.16 (m, 3H), 2.90-2.82 (m, 3H), 2.55 (s, 3H), 2.43 (s, 3H), 2.05 (t, J=6.8 Hz, 2H), 1.96-1.91 (m, 2H), 1.85-1.82 (m, 2H), 1.74-1.62 (m, 5H), 1.47-1.43 (m, 2H).

LC-MS [mobile phase: from 95% water (0.1% FA) and 5% ACN (0.1% FA) to 5% water (0.1% FA) and 95% ACN (0.1% FA) in 9 min]: Rt=4.54 min; MS Calcd: 515, MS Found: 516 [M+H]+.

Example B-7

7-(2-Methyl-6-(5-methyl-6-(1-(oxetan-3-yl)piperidin-4-yl)-1H-indazol-1-yl)pyrimidin-4-yl)-4-oxa-7-azaspiro[2.5]octane

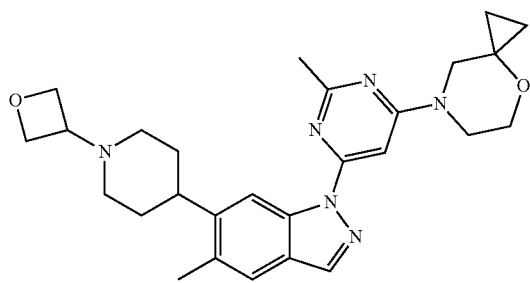 [SMILES: Cc1nc(N2CCOC3(CC3)C2)cc(-n2ncc3cc(C)c(C4CCN(C5COC5)CC4)cc32)n1]

To a mixture of 5-methyl-6-(1-(oxetan-3-yl)piperidin-4-yl)-1H-indazole (81 mg, 0.298 mmol), 7-(6-iodo-2-methylpyrimidin-4-yl)-4-oxa-7-azaspiro[2.5]octane (100 mg, 0.302 mmol), K3PO4 (127 mg, 0.60 mmol) and CuI (57 mg, 0.30 mmol) in toluene (2 ml) under Ar was added N,N'-dimethylethylenediamine (53 mg, 0.60 mmol). The reaction was stirred at 95° C. for 3 hours.

The reaction mixture was filtered and the filter cake was washed with CH2Cl2. The combined filtrate was concentrated and the residue was purified by column chromatography eluted with CH2Cl2/MeOH=15/1 afforded pure desired product as white solid (76 mg, yield: 53%).

LC-MS [mobile phase: from 80% water (0.1% TFA) and 20% ACN (0.1% TFA) to 5% water (0.1% TFA) and 95% ACN (0.1% TFA) in 10.0 min]: Rt=5.11 min; MS Calcd: 474, MS Found: 475 [M+H]+.

1H NMR (400 MHz, CDCl3) δ 8.82 (s, 1H), 8.05 (s, 1H), 7.50 (s, 1H), 6.90 (s, 1H), 4.71 (d, J=6.8 Hz, 4H), 3.87 (t, J=4.4 Hz, 2H), 3.80 (d, J=4.4 Hz, 2H), 3.66 (s, 2H), 3.57 (t, J=6.4 Hz, 1H), 2.97 (d, J=10.4 Hz, 2H), 2.85-2.81 (m, 1H), 2.64 (s, 3H), 2.45 (s, 3H), 2.05-2.00 (m, 2H), 1.94 (br, 4H), 0.90-0.55 (m, 4H), 0.68 (m, 2H).

Example B-8

8-(2-Methyl-6-(5-methyl-6-((tetrahydrofuran-3-yl)oxy)-1H-indazol-1-yl)pyrimidin-4-yl)-2,8-diazaspiro[4.5]decan-1-one

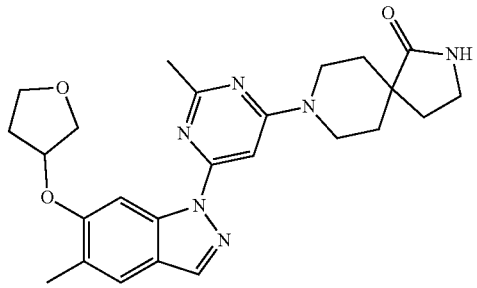 [SMILES: Cc1nc(N2CCC3(CCNC3=O)CC2)cc(-n2ncc3cc(C)c(OC4CCOC4)cc32)n1]

A mixture of 8-(6-iodo-2-methylpyrimidin-4-yl)-2,8-diazaspiro[4.5]decan-1-one (119 mg, 0.32 mmol), 5-methyl-6-((tetrahydrofuran-3-yl)oxy)-1H-indazole (70 mg, 0.32 mmol), N,N'-dimethylcyclohexane-1,2-diamine (90 mg, 0.64 mmol), CuI (61 mg, 0.32 mmol) and K3PO4 (136 mg, 0.64 mmol) in toluene (3 mL) was stirred at 100° C. for 2 hours. The mixture was filtered and concentrated. The residue was purified by prep-HPLC (gilson-2 Kinete EVO C18, 5 μm 21.2×150 mm; 20-50% B, A: H2O (0.1% HCl), B: ACN, UV: 214 nm, flow rate 20 ml/min) to give the title compound (97 mg, 66%) as a white solid.

1HNMR (400 MHz, CDCl3): δ 8.16 (s, 1H), 8.09 (s, 1H), 7.48 (s, 1H), 7.16 (s, 1H), 5.54 (br, 1H), 5.07 (br, 1H), 4.40-4.37 (m, 2H), 4.13-3.95 (m, 6H), 3.40 (t, J=6.4, 2H), 3.03 (s, 3H), 2.34-2.27 (m, 5H), 2.14-2.07 (m, 4H), 1.81-1.76 (m, 2H).

LC-MS [column: C18; column size: 4.6×50 mm; mobile phase: B (ACN): A (0.1% TFA); gradient (B %) in 6 min]: Rt=3.088 min, MS Calcd.: 462, MS Found: 463 [M+H]+.

Example B-9

8-(2-Methoxy-6-(5-methyl-6-(1-(oxetan-3-yl)piperidin-4-yl)-1H-indazol-1-yl)pyrimidin-4-yl)-2,5-dioxa-8-azaspiro[3.5]nonane

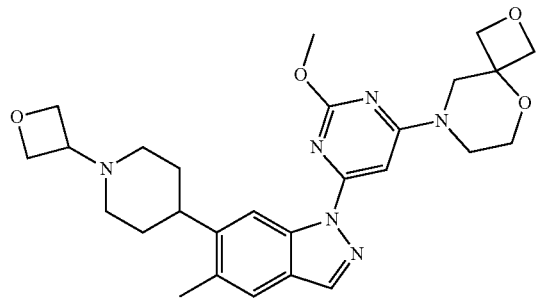

To a mixture of 8-(2-methoxy-6-(5-methyl-6-(piperidin-4-yl)-1H-indazol-1-yl)pyrimidin-4-yl)-2,5-dioxa-8-azaspiro[3.5]nonane (139 mg, 0.31 mmol), oxetan-3-one (111 mg, 1.55 mmol), Na(CN)BH3 (39 mg, 0.62 mmol) in DCM (4 mL), was added AcOH (2 drops). The mixture was stirred at room temperature for 4 hours. The mixture was concentrated. The crude was purified by prep-HPLC (sunfire C18, 5 μm, 19×150 mm, 05-50% ACN-H2O (0.1% HCl), flow rate: 15 ml/min, GT 10 mins.) to give solution A, The solution A was washed with NaHCO3 (aq). The organic layer was concentrated to give the title compound (27 mg, 17%) as a white solid.

1H NMR (400 MHz, CDCl3): δ 8.80 (s, 1H), 8.12 (s, 1H), 7.56 (s, 1H), 6.95 (s, 1H), 4.74-4.71 (M, 4H), 4.69 (d, J=7.2 Hz, 2H), 4.52 (d, J=6.8 Hz, 2H), 4.20 (s, 3H), 4.01 (s, 2H), 3.81-3.80 (m, 2H), 3.71 (t, J=5.2 Hz, 2H), 3.61-3.58 (m, 1H), 2.97 (d, J=11.2 Hz, 2H), 2.88 (t, J=3.6 Hz, 1H), 2.50 (s, 3H), 2.09-2.03 (m, 2H), 1.98-1.91 (m, 4H).

LC-MS [Phenomenex Kinetex 5 μm EVO C18, 50×4.6 mm; mobile phase: B (ACN): A (0.02% NH4OAc); gradient (B %) in 6 min]: Rt=3.795 min; MS Calcd.: 506, MS Found: 507 [M+H]+.

Example B-10

8-(2-Methoxy-6-(5-methyl-6-(piperidin-4-yl)-1H-indazol-1-yl)pyrimidin-4-yl)-2,5-dioxa-8-azaspiro[3.5]nonane To a solution of tert-butyl 4-(1-(2-methoxy-6-(2,5-dioxa-8-azaspiro[3.5]nonan-8-yl)pyrimidin-4-yl)-5-methyl-1H-indazol-6-yl)piperidine-1-carboxylate (170 mg, 0.31 mmol) in TFA (1 mL) and DCM (4 mL) was stirred at room temperature for 5 hours. Sat. NaHCO$_3$ was added to the reaction to adjust pH>7. The mixture was diluted with H$_2$O (50 mL), extracted with EtOAc (30 mL×3). The combined organic layer was dried over Na$_2$SO$_4$, filtered and concentrated to give the compound (139 mg, 100%) as white solid.

F. Biological Data

As stated above, the compounds of the present invention are LRRK2 kinase inhibitors, and are useful in the treatment of diseases mediated by LRRK2. The biological activities of the compounds of the present invention can be determined using any suitable assay for determining the activity of a candidate compound as a LRRK2 kinase inhibitor, as well as tissue and in vivo models.

1) Full Length G2019 Human LRRK2 Inhibition Mass Spectrometry Assay

Insect Cell Cultures

Sf9 insect cells (Invitrogen Life Technologies, Carlsbad, Calif.) were maintained at 27° C. in SF 900 II SFM in 500-ml stationary flasks. The cells were maintained in exponential growth phase and subcultured twice per week. For larger volumes, cells were grown in 2-liter shaker flasks (Erlenmeyer, Corning) while being agitated with 120 rpm at 27° C. incubator shaker.

Human G2019 LRRK2 Plasmids Preparation
Primers used for PCR cloning:
pHTBV-F: SEQ ID No: 1
LRRK2 wt-F1: SEQ ID No: 2
LRRK2 wt-R1: SEQ ID No: 3
LRRK2 wt-F2: SEQ ID No: 4
LRRK2 wt-R2: SEQ ID No: 5
LRRK2 wt-F3: SEQ ID No: 6
pHTBV-R: SEQ ID No: 7

The primers described above were used to amplify full length human LRRK2 (amino acids from 1-2527) with N terminal Flag tag from BioCat 116313 using high fidelity PCR polymerase KOD-Plus according to the manufacturer's instructions (KOD-211, TOYOBO). The PCR product was digested with BamHI and KpnI and ligated into BamHI and KpnI digested pHTBV1mcs3(BioCat 127555). The sequence of the target fragment was confirmed by DNA sequencing. The construct BioCat141351 was generated by Novoprotein.

The G2019 full length Flag-LRRK2 coding sequence is SEQ ID No: 8.

The translated protein sequence for human G2019 full length LRRK2 flag tagged protein is SEQ ID No: 9.

Generation of the BacMam Virus

To generate the recombinant BacMam virus, SF9 cells were seeded in 6-well tissue culture dishes at 9×10$^5$ cells/well and allowed to attach for 20 min. Transfection procedure was followed using AESOP AP5911v2. Briefly, DH10Bac competent cells (10361-012, Invitrogen) were transformed by the genotypically normal human LRRK2 BacMam plasmid to generate the recombinant baculovirus DNA. The Sf9 insect cells were co-transfected with the mixture of recombinant baculovirus DNA and cellfectin (10362-100, Invitrogen). After 4 h of incubation at 27° C., the transfection media was replaced with Sf-900 III SFM medium containing 5% HI FBS (Ser. No. 10/100,147, Invitrogen). The cells were further incubated for 4 days. The infected cell culture medium containing the baculovirus (P0 virus stock) was collected and amplified by further infecting the Sf9 cells at multiplicity of infection (MOI) (pfu/cell) of 0.1.

Quantification of BacMam Viral Titre by BacPAKRapid Titer

The viral titre, measured as plaque forming unit (pfu)/ml was determined using BacPAK Papid Titer Kit (631406, Clontech) according to the manufacturer's protocol. The Sf9 cells seeded in 96-well plate with 3×10$^5$ cells per well were incubated with serial dilution of the viral stocks for 1 h at 27° C., 50 μl methyl cellulose overlay was added to each well followed by 43-47 h incubation. The cells were then fixed in 4% paraformaldehyde (PFA). After blocking the cells with diluted normal goat serum, Mouse anti-gp64 antibody was added to the cells. After 30 min incubation, the cells were washed with phosphate buffered saline containing 0.1% Triton-X100 (PBST) and incubated for another 30 min with goat anti-mouse antibody/HRP conjugate. This was followed by blue peroxidase substrate which detects the single infected cells and foci of infected cells by their dark blue color.

Protein Expression

Expression of Flag Tagged Full Length G2019 Human LRRK2

HEK293 6E cells (BioCat: 120363) were incubated in a 37° C. incubator with a humidified atmosphere of 5% CO$_2$ on an orbital shaker rotating at 110 rpm. On the day of transduction, the cell viability was higher than 98% and the cell density was in the range of 1×10$^6$~1.5×10$^6$ cells/ml.

HEK293 6E cells were centrifuged at 1,000 rpm for 10 min, and then the cells were resuspended in fresh Freestyle 293 expression medium(Invitrogen:12338) with 0.1% F-68 (Invitrogen:24040-032) but without antibiotics(G418) at density of 1×10$^6$ cells/mi. BacMam virus with Flag-hu LRRK2 (genotypically normal) gene was centrifuged at 40,000 g for 2 hours, then resuspended in fresh Freestyle 293 expression medium. The resuspended virus was added into the cells in at MOI of 10. The cells were incubated in a 37° C. incubator with a humidified atmosphere of 5% CO$_2$ in air on an orbital shaker rotating at 110 rpm. Cultures were harvested at approximately 48 hours post-transduction by centrifugation at 4,000 rpm for 20 min and pellets were frozen for purification.

Protein Purification

Purification of Flag Tagged Full Length G2019 Human LRRK2

The cell pellet was resuspended in 20 mL lysis buffer (50 mM TrisHCl pH7.5 at 4° C., 500 mM NaCl, 0.5 mM EDTA, 0.1% TritonX-100, 10% glycerol, freshly add 2 mM DTT), with protease inhibitors (Roche: 04693132001) and benzonase(Merck Millipore: 70746-3CN) at recommended concentration suggested by suppliers. The suspended cells were lysed by sonication on ice for 30 min (2 secs on/4 sec off, 20% amplitude), and centrifuged at 10,000 rpm for 30 minutes at 4° C. The supernatant was incubated with 1 mL per litre of cell culture of anti-Flag magnetic beads (Sigma-Aldrich: M8823) at 4° C. for 3 hours, then the beads were washed by 5 mL per litre of cell culture binding buffer (50 mM Tris pH7.5@ 4C, 500 mM NaCl, 0.5 mM EDTA, 0.1% TritonX-100, 10% glycerol, freshly add 2 mM DTT) for three times. The Flag tagged LRRK2 proteins were eluted by Elution buffer (50 mM Tris pH7.5@ 4C, 500 mM NaCl, 0.5 mM EDTA, 0.1% TritonX-100, 10% glycerol, freshly add 2 mM DTT, 250 ug/ml Flag peptide (Sigma-Aldrich:F3290)) at 4° C. for 2 hours. Flag peptide was removed by Zeba Spin Desalting Columns, 7K MWCO(Thermo-Fisher: 89893) and the buffer of eluted LRRK2 proteins was exchanged into Storage Buffer (50 mM Tris pH7.5@4C, 150 mM NaCl, 0.5 mM EDTA, 0.02% Triton X-100, 2 mM DTT and 50% Glycerol) using Amicon Ultra Centrifugal Filter Units (100 kD) (Merck: UFC910096). Fractions containing LRRK2 proteins were pooled, aliquoted and stored at −80° C. Protein concentration was determined by Bradford protein assay, and protein purity was analyzed by NuPAG Novex 4-12% Bis-Tris Protein Gels (Invitrogen: NP0322BOX).

Full length G2019 human LRRK2 Inhibition Mass Spectrometry Assay

This assay for Leucine Rich Repeat Kinase 2 (LRRK2) inhibition is based on the direct measurement of the peptide 'LRRKtide' (LRRKtide: RLGRDKYKT*LRQIRQ and "*" refers to the site of phosphorylation.) and phosphorylated 'LRRKtide' using a high throughput RapidFire mass spectrometry assay. Inhibitors are defined as compounds which reduce the conversion of LRRKtide to phospho-LRRKtide.

Assay Protocol
1. A 10 mM test compound was dissolved in 100% DMSO and serially diluted 1 in 4. 100 nL of this dilution series was then added to a 384 well, v bottom polypropylene plate, excluding columns 6 and 18. 100 nL of DMSO was added to columns 6 and 18 as controls wells. Assay dilution gave a top final assay concentration of test compound of 100 μM
2. 50 ul of 1% formic acid in laboratory grade water was added to column 18 using a multidrop combi dispenser to act as a pre stopped assay control.
3. 5 uL of 'enzyme solution' containing 50 nM of purified recombinant Full length Flag-LRRK2 in assay buffer (50 mM Hepes (pH 7.2), 10 mM $MgCl_2$, 150 mM NaCl, 5% glycerol, 0.0025% triton X-100 and 1 mM DTT) was added to all wells using a multidrop combi dispenser, giving a final assay concentration of 25 nM LRRK2 enzyme. This resulted in column 6 (enzyme plus DMSO) giving 0% inhibition and column 18 giving 100% inhibition (pre stopped control). Test plates were then incubated for 30 minutes at room temperature.
4. 5 uL 'substate solution' containing 50 uM LRRKtide peptide substrate and 4 mM ATP was added to all wells of the plate using a multidrop combi dispenser giving a final assay concentration of 25 μm LRRKtide and 2 mM ATP. Test plates were then incubated for 1 hour at room temperature. (Incubation may vary depending on rate and linearity of reaction with different enzyme batches).
5. 50 ul of 1% formic acid in laboratory grade water was added to all wells (minus column 18) to quench the reaction, and plates were centrifuged at 3000 rpm for 10 minutes. Test plates were then analysed on an Agilent RapidFire High Throughput solid phase extraction system coupled to AB Sciex API 4000 triple quadropole mass spectrometer with the following setting:

RapidFire Settings:
Sip Height=2 mm, Aspirate=500 ms, Load time=3000 ms, Elution time=3000 ms, Requilibration=500 ms,
Flow rates: pump 1=1.5 mL/min, pump 2 1.25 mL/min pump 3=0.8 mL/min Mass Spectrometer Settings LRRKtide Detection settings: Q1 mass 644.8 Da, Q3 mass 638.8, declustering potential 76 volts, collision energy 37 volts, CXP 34 volts Phospho-LRRKtide Detection settings: Q1mass 671.4 Da, Q3 mass 638.8, Declustering potential 76 volts, Collision energy 37 volts, CXP 34 volts.

A C4 cartridge was used and running buffers were: A (aqueous) 0.1% formic acid in water B (organic) 0.1% formic acid, 80% acetonitrile, 20% water 6. Data was analysed using ActivityBase software (IDBS). A percent conversion from LRRKtide to Phospho-LRRKtide was calculated using the following formula: % conversion=(Phospho-LRRKtide product peak area/(Phospho-LRRKtide product peak area+ LRRKtide substrate peak area))*100

2) Recombinant Cellular LRRK2 AlphaScreen Assay

To determine the activity of compounds against LRRK2 kinase activity in cells, the observed LRRK2 kinase-dependent modulation of LRRK2 Ser 935 phosphorylation (Dzamko et al., 2010, Biochem. J. 430: 405-413) was utilized to develop a quantitative 384 well plate-based immunoassay of LRRK2 Ser935 phosphorylation in the human neuroblastoma cell line SH-SY5Y, engineered to over-express recombinant full length LRRK2 protein.

A BacMam virus expressing full length recombinant LRRK2 was purchased from Invitrogen and amplified by inoculation of SF-9 cells at MOI 0.3 for 4-5 days in Sf-900 III SFM medium supplemented with 3% fetal bovine serum. Infected cell cultures were then centrifuged at 2000 g for 20 minutes, viral supernatant titer determined by anti-gp64 plaque assay and stored at 4° C.

Affinity-purified anti-phospho LRRK2 Ser935 sheep polyclonal antibody (Dzamko et al., 2010, Biochem. J. 430: 405-413) was biotinylated by standard methods (PerkinElmer). Anti-LRRK2 rabbit polyclonal antibody was purchased from Novus Biologicals. AlphaScreen Protein A IgG Kit (including acceptor and donor beads) was purchased from Perkin Elmer.

SH-SY5Y cells were grown in DMEM/F12 medium with 10% dialysed fetal bovine serum and harvested by treatment with 0.5% trypsin-EDTA for 5 minutes at 37° C. followed by centrifugation at 1000 rpm for 4 minutes. The cell pellet was resuspended in Opti-MEM reduced serum media (Invitrogen) at 200,000 cells/ml and mixed with the BacMam LRRK2 virus at MOI=50. 50 μl cell solutions were then dispensed to each well of a 384-well plate and incubated at 37° C., 5% $CO_2$ for 24 hours.

Serial dilutions of test compounds were prepared in Opti-MEM reduced serum media (Invitrogen) and 5.6 ul transferred from compound plate to cell assay plate to achieve a top final assay concentration of 10 uM. DMSO was used in certain wells as controls. Cells were incubated at 37° C., 5% $CO_2$ for 60 minutes. The medium was then removed and cells lysed by addition of 20 ul cell lysis buffer (Cell Signaling Technology) and incubation at 4° C. for 20 minutes. 10 ul of antibody/acceptor bead mix [(1/1000 biotinylated-pS935 LRRK2 antibody, 1/1000 total-LRRK2 antibody, 1/100 Acceptor beads in AlphaScreen detection buffer (25 mM Hepes (pH 7.4), 0.5% Triton X-100, 1 mg/ml Dextran 500 and 0.1% BSA)] was then added to each well and plates incubated for 2 hours at ambient temperature in the dark. 10 μl of donor beads solution (1/33.3 donor beads in AlphaScreen detection buffer) was then added to each well. Following incubation for a further 2 hours at ambient temperature in the dark, plates were read on an EnVision™ plate reader at emission 520-620 nm with excitation 680 nm. Dose response curve data was based on sigmoidal dose-response model.

Pharmacological Data

Compounds of Examples A-1-A-13 were tested in the recombinant cellular LRRK2 AlphaScreen assay and exhibited a pIC50>6. Compounds of Examples A-1-A-4 and A-13 exhibited a pIC50≥7 in the recombinant cellular LRRK2 AlphaScreen assay. The compound of example A-13 exhibited a pIC50 of 8.1 in the recombinant cellular LRRK2 AlphaScreen assay.

Compounds of Examples A-1-A-7 were additionally tested in the full length G2019 human LRRK2 Inhibition Mass Spectrometry assay and exhibited a pIC50≥6.5.

```
Sequence listing
SEQ ID NO: 1 Primers used for PCR cloning of Human G2019 LRRK2 plasmids preparation: pHTBV-F
5'-GATCTCGACGGGCGCGGATCCACCATGGATTACAAGGATGACGACGAT-3'

SEQ ID NO: 2 Primers used for PCR cloning of Human G2019 LRRK2 plasmids preparation: LRRK2
wt-F1
5'-CATGGATTACAAGGATGACGACGATAAGATGGCTAGTGGCAGCTGTCAG-3'

SEQ ID NO: 3 Primers used for PCR cloning of Human G2019 LRRK2 plasmids preparation: LRRK2
wt-R1
5'-GTTCACGAGATCCACTATTCAGTAAGAGTTCCACCAATTTGGGACTG-3'

SEQ ID NO: 4 Primers used for PCR cloning of Human G2019 LRRK2 plasmids preparation: LRRK2
wt-F2
5'-GAATAGTGGATCTCGTGAACAAG-3'

SEQ ID NO: 5 Primers used for PCR cloning of Human G2019 LRRK2 plasmids preparation: LRRK2
wt-R2
5'-GTCAGACAAACTGCTTGGAACCAGC-3'

SEQ ID NO: 6 Primers used for PCR cloning of Human G2019 LRRK2 plasmids preparation: LRRK2
wt-F3
5'-CTGGTTCCAAGCAGTTTGTCTGACCACAGGCCTGTGATAG-3'

SEQ ID NO: 7 Primers used for PCR cloning of Human G2019 LRRK2 plasmids preparation: pHTBV-R
5'-GTTCTAGCCAAGCTTGGTACCCTATTACTCAACAGATGTTCGTCTC-3'

SEQ ID NO: 8 G2019 full length Flag-LRRK2 coding sequence
atggattacaaggatgacgacgataagATGGCTAGTGGCAGCTGTCAGGGGTGCGAAGAGGACGAGGAAAC

TCTGAAGAAGTTGATAGTCAGGCTGAACAATGTCCAGGAAGGAAAACAGATAGAAACGCTGGTC

CAAATCCTGGAGGATCTGCTGGTGTTCACGTACTCCGAGCACGCCTCCAAGTTATTTCAAGGCAA

AAATATCCATGTGCCTCTGTTGATCGTCTTGGACTCCTATATGAGAGTCGCGAGTGTGCAGCAGG

TGGGTTGGTCACTTCTGTGCAAATTAATAGAAGTCTGTCCAGGTACAATGCAAAGCTTAATGGGA

CCCCAGGATGTTGGAAATGATTGGGAAGTCCTTGGTGTTCACCAATTGATTCTTAAAATGCTAAC

AGTTCATAATGCCAGTGTAAACTTGTCAGTGATTGGACTGAAGACCTTAGATCTCCTCCTAACTTC

AGGTAAAATCACCTTGCTGATACTGGATGAAGAAAGTGATATTTTCATGTTAATTTTTGATGCCAT

GCACTCATTTCCAGCCAATGATGAAGTCCAGAAACTTGGATGCAAAGCTTTACATGTGCTGTTTG

AGAGAGTCTCAGAGGAGCAACTGACTGAATTTGTTGAGAACAAAGATTATATGATATTGTTAAGT

GCGTTAACAAATTTTAAAGATGAAGAGGAAATTGTGCTTCATGTGCTGCATTGTTTACATTCCCTA

GCGATTCCTTGCAATAATGTGGAAGTCCTCATGAGTGGCAATGTCAGGTGTTATAATATTGTGGT

GGAAGCTATGAAAGCATTCCCTATGAGTGAAAGAATTCAAGAAGTGAGTTGCTGTTTGCTCCATA

GGCTTACATTAGGTAATTTTTTCAATATCCTGGTATTAAACGAAGTCCATGAGTTTGTGGTGAAAG

CTGTGCAGCAGTACCCAGAGAATGCAGCATTGCAGATCTCAGCGCTCAGCTGTTTGGCCCTCCT

CACTGAGACTATTTTCTTAAATCAAGATTTAGAGGAAAAGAATGAGAATCAAGAGAATGATGATGA

GGGGGAAGAAGATAAATTGTTTTGGCTGGAAGCCTGTTACAAAGCATTAACGTGGCATAGAAAGA

ACAAGCACGTGCAGGAGGCCGCATGCTGGGCACTAAATAATCTCCTTATGTACCAAAACAGTTTA

CATGAGAAGATTGGAGATGAAGATGGCCATTTCCCAGCTCATAGGGAAGTGATGCTCTCCATGC

TGATGCATTCTTCATCAAAGGAAGTTTTCCAGGCATCTGCGAATGCATTGTCAACTCTCTTAGAAC

AAAATGTTAATTTCAGAAAAATACTGTTATCAAAAGGAATACACCTGAATGTTTTGGAGTTAATGCA

GAAGCATATACATTCTCCTGAAGTGGCTGAAAGTGGCTGTAAAATGCTAAATCATCTTTTTTGAAGG
```

```
AAGCAACACTTCCCTGGATATAATGGCAGCAGTGGTCCCCAAAATACTAACAGTTATGAAACGTC

ATGAGACATCATTACCAGTGCAGCTGGAGGCGCTTCGAGCTATTTTACATTTTATAGTGCCTGGC

ATGCCAGAAGAATCCAGGGAGGATACAGAATTTCATCATAAGCTAAATATGGTTAAAAAACAGTG

TTTCAAGAATGATATTCACAAACTGGTCCTAGCAGCTTTGAACAGGTTCATTGGAAATCCTGGGAT

TCAGAAATGTGGATTAAAAGTAATTTCTTCTATTGTACATTTTCCTGATGCATTAGAGATGTTATCC

CTGGAAGGTGCTATGGATTCAGTGCTTCACACACTGCAGATGTATCCAGATGACCAAGAAATTCA

GTGTCTGGGTTTAAGTCTTATAGGATACTTGATTACAAAGAAGAATGTGTTCATAGGAACTGGACA

TCTGCTGGCAAAAATTCTGGTTTCCAGCTTATACCGATTTAAGGATGTTGCTGAAATACAGACTAA

AGGATTTCAGACAATCTTAGCAATCCTCAAATTGTCAGCATCTTTTTCTAAGCTGCTGGTGCATCA

TTCATTTGACTTAGTAATATTCCATCAAATGTCTTCCAATATCATGGAACAAAAGGATCAACAGTTT

CTAAACCTCTGTTGCAAGTGTTTTGCAAAAGTAGCTATGGATGATTACTTAAAAAATGTGATGCTA

GAGAGAGCGTGTGATCAGAATAACAGCATCATGGTTGAATGCTTGCTTCTATTGGGAGCAGATG

CCAATCAAGCAAAGGAGGGATCTTCTTTAATTTGTCAGGTATGTGAGAAAGAGAGCAGTCCCAAA

TTGGTGGAACTCTTACTGAATAGTGGATCTCGTGAACAAGATGTACGAAAAGCGTTGACGATAAG

CATTGGGAAAGGTGACAGCCAGATCATCAGCTTGCTCTTAAGGAGGCTGGCCCTGGATGTGGCC

AACAATAGCATTTGCCTTGGAGGATTTTGTATAGGAAAAGTTGAACCTTCTTGGCTTGGTCCTTTA

TTTCCAGATAAGACTTCTAATTTAAGGAAACAAACAAATATAGCATCTACACTAGCAAGAATGGTG

ATCAGATATCAGATGAAAAGTGCTGTGGAAGAAGGAACAGCCTCAGGCAGCGATGGAAATTTTTC

TGAAGATGTGCTGTCTAAATTTGATGAATGGACCTTTATTCCTGACTCTTCTATGGACAGTGTGTT

TGCTCAAAGTGATGACCTGGATAGTGAAGGAAGTGAAGGCTCATTTCTTGTGAAAAAGAAATCTA

ATTCAATTAGTGTAGGAGAATTTTACCGAGATGCCGTATTACAGCGTTGCTCACCAAATTTGCAAA

GACATTCCAATTCCTTGGGGCCCATTTTTGATCATGAAGATTTACTGAAGCGAAAAAGAAAAATAT

TATCTTCAGATGATTCACTCAGGTCATCAAAACTTCAATCCCATATGAGGCATTCAGACAGCATTT

CTTCTCTGGCTTCTGAGAGAGAATATATTACATCACTAGACCTTTCAGCAAATGAACTAAGAGATA

TTGATGCCCTAAGCCAGAAATGCTGTATAAGTGTTCATTTGGAGCATCTTGAAAAGCTGGAGCTT

CACCAGAATGCACTCACGAGCTTTCCACAACAGCTATGTGAAACTCTGAAGAGTTTGACACATTT

GGACTTGCACAGTAATAAATTTACATCATTTCCTTCTTATTTGTTGAAAATGAGTTGTATTGCTAAT

CTTGATGTCTCTCGAAATGACATTGGACCCTCAGTGGTTTTAGATCCTACAGTGAAATGTCCAACT

CTGAAACAGTTTAACCTGTCATATAACCAGCTGTCTTTTGTACCTGAGAACCTCACTGATGTGGTA

GAGAAACTGGAGCAGCTCATTTTAGAAGGAAATAAAATATCAGGGATATGCTCCCCCTTGAGACT

GAAGGAACTGAAGATTTTAAACCTTAGTAAGAACCACATTTCATCCCTATCAGAGAACTTTCTTGA

GGCTTGTCCTAAAGTGGAGAGTTTCAGTGCCAGAATGAATTTTCTTGCTGCTATGCCTTTCTTGC

CTCCTTCTATGACAATCCTAAAATTATCTCAGAACAAATTTTCCTGTATTCCAGAAGCAATTTTAAA

TCTTCCACACTTGCGGTCTTTAGATATGAGCAGCAATGATATTCAGTACCTACCAGGTCCCGCAC

ACTGGAAATCTTTGAACTTAAGGGAACTCTTATTTAGCCATAATCAGATCAGCATCTTGGACTTGA

GTGAAAAAGCATATTTATGGTCTAGAGTAGAGAAACTGCATCTTTCTCACAATAAACTGAAAGAGA

TTCCTCCTGAGATTGGCTGTCTTGAAAATCTGACATCTCTGGATGTCAGTTACAACTTGGAACTAA

GATCCTTTCCCAATGAAATGGGGAAATTAAGCAAAATATGGGATCTTCCTTTGGATGAACTGCAT

CTTAACTTTGATTTTAAACATATAGGATGTAAAGCCAAAGACATCATAAGGTTTCTTCAACAGCGA

TTAAAAAAGGCTGTGCCTTATAACCGAATGAAACTTATGATTGTGGGAAATACTGGGAGTGGTAA
```

-continued

```
AACCACCTTATTGCAGCAATTAATGAAAACCAAGAAATCAGATCTTGGAATGCAAAGTGCCACAG

TTGGCATAGATGTGAAAGACTGGCCTATCCAAATAAGAGACAAAAGAAAGAGAGATCTCGTCCTA

AATGTGTGGGATTTTGCAGGTCGTGAGGAATTCTATAGTACTCATCCCCATTTTATGACGCAGCG

AGCATTGTACCTTGCTGTCTATGACCTCAGCAAGGGACAGGCTGAAGTTGATGCCATGAAGCCTT

GGCTCTTCAATATAAAGGCTCGCGCTTCTTCTTCCCCTGTGATTCTCGTTGGCACACATTTGGAT

GTTTCTGATGAGAAGCAACGCAAAGCCTGCATGAGTAAAATCACCAAGGAACTCCTGAATAAGCG

AGGGTTCCCTGCCATACGAGATTACCACTTTGTGAATGCCACCGAGGAATCTGATGCTTTGGCAA

AACTTCGGAAAACCATCATAAACGAGAGCCTTAATTTCAAGATCCGAGATCAGCTTGTTGTTGGA

CAGCTGATTCCAGACTGCTATGTAGAACTTGAAAAAATCATTTTATCGGAGCGTAAAAATGTGCCA

ATTGAATTTCCCGTAATTGACCGGAAACGATTATTACAACTAGTGAGAGAAAATCAGCTGCAGTTA

GATGAAAATGAGCTTCCTCACGCAGTTCACTTTCTAAATGAATCAGGAGTCCTTCTTCATTTTCAA

GACCCAGCACTGCAGTTAAGTGACTTGTACTTTGTGGAACCCAAGTGGCTTTGTAAAATCATGGC

ACAGATTTTGACAGTGAAAGTGGAAGGTTGTCCAAAACACCCTAAGGGAATTATTTCGCGTAGAG

ATGTGGAAAAATTTCTTTCAAAGAAAAGGAAATTTCCAAAGAACTACATGTCACAGTATTTTAAGC

TCCTAGAAAAATTCCAGATTGCTTTGCCAATAGGAGAAGAATATTTGCTGGTTCCAAGCAGTTTGT

CTGACCACAGGCCTGTGATAGAGCTTCCCCATTGTGAGAACTCTGAAATTATCATCCGACTATAT

GAAATGCCTTATTTTCCAATGGGATTTTGGTCAAGATTAATCAATCGATTACTTGAGATTTCACCTT

ACATGCTTTCAGGGAGAGAACGAGCACTTCGCCCAAACAGAATGTATTGGCGACAAGGCATTTA

CTTAAATTGGTCTCCTGAAGCTTATTGTCGGTAGGATCTGAAGTCTTAGACAATCATCCAGAGA

GTTTCTTAAAAATTACAGTTCCTTCTTGTAGAAAAGGCTGTATTCTTTTGGGCCAAGTTGTGGACC

ACATTGATTCTCATGGAAGAATGGTTTCCTGGGTTGCTGGAGATTGATATTTGTGGTGAAGGA

GAAACTCTGTTGAAGAAATGGGCATTATATAGTTTTAATGATGGTGAAGAACATCAAAAAATCTTA

CTTGATGACTTGATGAAGAAAGCAGAGGAAGGAGATCTCTTAGTAAATCCAGATCAACCAAGGCT

CACCATTCCAATATCTCAGATTGCCCCTGACTTGATTTTGGCTGACCTGCCTAGAAATATTATGTT

GAATAATGATGAGTTGGAATTTGAACAAGCTCCAGAGTTTCTCCTAGGTGATGGCAGTTTTGGAT

CAGTTTACCGAGCAGCCTATGAAGGAGAAGAAGTGGCTGTGAAGATTTTTAATAAACATACATCA

CTCAGGCTGTTAAGACAAGAGCTTGTGGTGCTTTGCCACCTCCACCACCCCAGTTTGATATCTTT

GCTGGCAGCTGGGATTCGTCCCCGGATGTTGGTGATGGAGTTAGCCTCCAAGGGTTCCTTGGAT

CGCCTGCTTCAGCAGGACAAAGCCAGCCTCACTAGAACCCTACAGCACAGGATTGCACTCCACG

TAGCTGATGGTTTGAGATACCTCCACTCAGCCATGATTATATACCGAGACCTGAAACCCCACAAT

GTGCTGCTTTTCACACTGTATCCCAATGCTGCCATCATTGCAAAGATTGCTGACTACGGCATTGC

TCAGTACTGCTGTAGAATGGGGATAAAAACATCAGAGGGCACACCAGGGTICGTGCACCTGAA

GTTGCCAGAGGAAATGTCATTTATAACCAACAGGCTGATGTTTATTCATTTGGTTTACTACTCTAT

GACATTTTGACAACTGGAGGTAGAATAGTAGAGGGTTTGAAGTTTCCAAATGAGTTTGATGAATTA

GAAATACAAGGAAAATTACCTGATCCAGTTAAAGAATATGGTTGTGCCCCATGGCCTATGGTTGA

GAAATTAATTAAACAGTGTTTGAAAGAAAATCCTCAAGAAAGGCCTACTTCTGCCCAGGTCTTTGA

CATTTTGAATTCAGCTGAATTAGTCTGTCTGACGAGACGCATTTTATTACCTAAAAACGTAATTGTT

GAATGCATGGTTGCTACACATCACAACAGCAGGAATGCAAGCATTTGGCTGGGCTGTGGGCACA

CCGACAGAGGACAGCTCTCATTTCTTGACTTAAATACTGAAGGATACACTTCTGAGGAAGTTGCT

GATAGTAGAATATTGTGCTTAGCCTTGGTGCATCTTCCTGTTGAAAAGGAAAGCTGGATTGTGTC

TGGGACACAGTCTGGTACTCTCCTGGTCATCAATACCGAAGATGGGAAAAAGAGACATACCCTA
```

```
GAAAAGATGACTGATTCTGTCACTTGTTTGTATTGCAATTCCTTTTCCAAGCAAAGCAAACAAAAA

AATTTTCTTTTGGTTGGAACCGCTGATGGCAAGTTAGCAATTTTTGAAGATAAGACTGTTAAGCTT

AAAGGAGCTGCTCCTTTGAAGATACTAAATATAGGAAATGTCAGTACTCCATTGATGTGTTTGAGT

GAATCCACAAATTCAACGGAAAGAAATGTAATGTGGGGAGGATGTGGCACAAAGATTTTCTCCTT

TTCTAATGATTTCACCATTCAGAAACTCATTGAGACAAGAACAAGCCAACTGTTTTCTTATGCAGC

TTTCAGTGATTCCAACATCATAACAGTGGTGGTAGACACTGCTCTCTATATTGCTAAGCAAAATAG

CCCTGTTGTGGAAGTGTGGGATAAGAAAACTGAAAAACTCTGTGGACTAATAGACTGCGTGCACT

TTTTAAGGGAGGTAATGGTAAAAGAAAACAAGGAATCAAAACACAAAATGTCTTATTCTGGGAGA

GTGAAAACCCTCTGCCTTCAGAAGAACACTGCTCTTTGGATAGGAACTGGAGGAGGCCATATTTT

ACTCCTGGATCTTTCAACTCGTCGACTTATACGTGTAATTTACAACTTTTGTAATTCGGTCAGAGT

CATGATGACAGCACAGCTAGGAAGCCTTAAAAATGTCATGCTGGTATTGGGCTACAACCGGAAAA

ATACTGAAGGTACACAAAAGCAGAAAGAGATACAATCTTGCTTGACCGTTTGGGACATCAATCTT

CCACATGAAGTGCAAAATTTAGAAAAACACATTGAAGTGAGAAAAGAATTAGCTGAAAAAATGAG

ACGAACATCTGTTGAGTAA
```

SEQ ID NO: 9 Translated protein sequence for human G2019 full length LRRK2 flag tagged protein

MDYKDDDDKMASGSCQGCEEDEETLKKLIVRLNNVQEGKQIETLVQILEDLLVFTYSEHASKLFQGKN

IHVPLLIVLDSYMRVASVQQVGWSLLCKLIEVCPGTMQSLMGPQDVGNDWEVLGVHQLILKMLTVHN

ASVNLSVIGLKTLDLLLTSGKITLLILDEESDIFMLIFDAMHSFPANDEVQKLGCKALHVLFERVSEEQLT

EFVENKDYMILLSALTNFKDEEEIVLHVLHCLHSLAIPCNNVEVLMSGNVRCYNIVVEAMKAFPMSERI

QEVSCCLLHRLTLGNFFNILVLNEVHEFVVKAVQQYPENAALQISALSCLALLTETIFLNQDLEEKNEN

QENDDEGEEDKLFWLEACYKALTWHRKNKHVQEAACWALNNLLMYQNSLHEKIGDEDGHFPAHRE

VMLSMLMHSSSKEVFQASANALSTLLEQNVNFRKILLSKGIHLNVLELMQKHIHSPEVAESGCKMLNH

LFEGSNTSLDIMAAVVPKILTVMKRHETSLPVQLEALRAILHFIVPGMPEESREDTEFHHKLNMVKKQC

FKNDIHKLVLAALNRFIGNPGIQKCGLKVISSIVHFPDALEMLSLEGAMDSVLHTLQMYPDDQEIQCLG

LSLIGYLITKKNVFIGTGHLLAKILVSSLYRFKDVAEIQTKGFQTILAILKLSASFSKLLVHHSFDLVIFHQM

SSNIMEQKDQQFLNLCCKCFAKVAMDDYLKNVMLERACDQNNSIMVECLLLLGADANQAKEGSSLIC

QVCEKESSPKLVELLLNSGSREQDVRKALTISIGKGDSQIISLLLRRLALDVANNSICLGGFCIGKVEPS

WLGPLFPDKTSNLRKQTNIASTLARMVIRYQMKSAVEEGTASGSDGNFSEDVLSKFDEWTFIPDSSM

DSVFAQSDDLDSEGSEGSFLVKKKSNSISVGEFYRDAVLQRCSPNLQRHSNSLGPIFDHEDLLKRKR

KILSSDDSLRSSKLQSHMRHSDSISSLASEREYITSLDLSANELRDIDALSQKCCISVHLEHLEKLELHQ

NALTSFPQQLCETLKSLTHLDLHSNKFTSFPSYLLKMSCIANLDVSRNDIGPSVVLDPTVKCPTLKQFN

LSYNQLSFVPENLTDVVEKLEQLILEGNKISGICSPLRLKELKILNLSKNHISSLSENFLEACPKVESFSA

RMNFLAAMPFLPPSMTILKLSQNKFSCIPEAILNLPHLRSLDMSSNDIQYLPGPAHWKSLNLRELLFSH

NQISILDLSEKAYLWSRVEKLHLSHNKLKEIPPEIGCLENLTSLDVSYNLELRSFPNEMGKLSKIWDLPL

DELHLNFDFKHIGCKAKDIIRFLQQRLKKAVPYNRMKLMIVGNTGSGKTTLLQQLMKTKKSDLGMQSA

TVGIDVKDWPIQIRDKRKRDLVLNVWDFAGREEFYSTHPHFMTQRALYLAVYDLSKGQAEVDAMKP

WLFNIKARASSSPVILVGTHLDVSDEKQRKACMSKITKELLNKRGFPAIRDYHFVNATEESDALAKLRK

TIINESLNFKIRDQLVVGQLIPDCYVELEKIILSERKNVPIEFPVIDRKRLLQLVRENQLQLDENELPHAVH

FLNESGVLLHFQDPALQLSDLYFVEPKWLCKIMAQILTVKVEGCPKHPKGIISRRDVEKFLSKKRKFPK

NYMSQYFKLLEKFQIALPIGEEYLLVPSSLSDHRPVIELPHCENSEIIIRLYEMPYFPMGFWSRLINRLLE

ISPYMLSGRERALRPNRMYWRQGIYLNWSPEAYCLVGSEVLDNHPESFLKITVPSCRKGCILLGQVV

DHIDSLMEEWFPGLLEIDICGEGETLLKKWALYSFNDGEEHQKILLDDLMKKAEEGDLLVNPDQPRLTI
PISQIAPDLILADLPRNIMLNNDELEFEQAPEFLLGDGSFGSVYRAAYEGEEVAVKIFNKHTSLRLLRQE
LVVLCHLHHPSLISLLAAGIRPRMLVMELASKGSLDRLLQQDKASLTRTLQHRIALHVADGLRYLHSAM
IIYRDLKPHNVLLFTLYPNAAIIAKIADYGIAQYCCRMGIKTSEGTPGFRAPEVARGNVIYNQQADVYSF
GLLLYDILTTGGRIVEGLKFPNEFDELEIQGKLPDPVKEYGCAPWPMVEKLIKQCLKENPQERPTSAQ
VFDILNSAELVCLTRRILLPKNVIVECMVATHHNSRNASIWLGCGHTDRGQLSFLDLNTEGYTSEEVAD
SRILCLALVHLPVEKESWIVSGTQSGTLLVINTEDGKKRHTLEKMTDSVTCLYCNSFSKQSKQKNFLLV
GTADGKLAIFEDKTVKLKGAAPLKILNIGNVSTPLMCLSESTNSTERNVMWGGCGTKIFSFSNDFTIQK
LIETRTSQLFSYAAFSDSNIITVVVDTALYIAKQNSPVVEVWDKKTEKLCGLIDCVHFLREVMVKENKES
KHKMSYSGRVKTLCLQKNTALWIGTGGGHILLLDLSTRRLIRVIYNFCNSVRVMMTAQLGSLKNVMLV
LGYNRKNTEGTQKQKEIQSCLTVWDINLPHEVQNLEKHIEVRKELAEKMRRTSVE

SEQ ID NO: 10: 'LRRKtide' peptide
H-RLGRDKYKTLRQIRQ-OH

---

What is claimed is:

1. A compound of Formula (I):

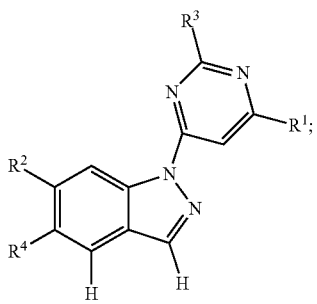

Formula (I)

wherein:
$R^1$ is
  a) an N-linked 6-9 membered fused bicyclic heterocyclyl ring optionally substituted with one, two or three substituents independently selected from the group consisting of oxo, halo, hydroxyl, $C_{1-3}$alkyl and $C_{1-3}$alkoxy;
    wherein:
      $C_{1-3}$alkyl and $C_{1-3}$alkoxy optionally is substituted with one or two substituents independently selected from the group consisting of halo, hydroxyl, unsubstituted $C_{1-3}$alkyl and unsubstituted $C_{1-3}$alkoxy; or
  b) an N-linked 7-10 membered heterospirane ring optionally substituted with one, two or three substituents independently selected from the group consisting of oxo, halo, hydroxyl, $C_{1-3}$alkyl and $C_{1-3}$alkoxy, wherein:
  $C_{1-3}$alkyl and $C_{1-3}$alkoxy optionally is substituted with one or two substituents independently selected from the group consisting or halo, hydroxyl, unsubstituted $C_{1-3}$alkyl and unsubstituted $C_{1-3}$alkoxy; and
provided that:
  $R^1$ is not 2-oxa-6-azaspiro[3.4]octan-6-yl;
$R^2$ is selected from the group consisting of:
  a) a 4-7 membered heterocyclyl ring optionally substituted with one, two or three substituents independently selected from the group consisting of $C_{1-3}$alkyl
    wherein:
      the $C_{1-3}$alkyl group optionally is substituted with one, two or three substituents independently selected from the group consisting of halo, hydroxyl, $CO_2H$, —$CH_2CH_2$—, $C_{1-3}$alkoxy, cyano, hydroxyl, —$SO_2CH_3$, —$COCH_3$, and —$COCH_2OH$;
    wherein:
      when the 4-7 membered heterocyclyl ring contains a substitutable nitrogen atom, the group of substituents identified for $R^2$ above further includes a 4-6 membered heterocyclyl ring;
    wherein:
      the 4-6 membered heterocyclyl ring optionally is substituted with one or two substituents independently selected from the group consisting of: cyano, halo, hydroxyl, $C_{1-3}$alkyl, $C_{1-3}$alkoxyl, $CH_2OH$ and $C_{3-6}$cycloalkyl which $C_{3-6}$cycloalkyl group is optionally substituted with one or two substituents independently selected from the group consisting of halo, hydroxyl, cyano, CH$_2$OH, unsubstituted C$_{1-3}$alkyl and unsubstituted C$_{1-3}$ alkoxyl;
provided that:
the 4-6 membered heterocyclyl ring is attached to the substitutable nitrogen atom of the 4-7 membered heterocyclyl ring as defined above;
b) —O-4-6 membered heterocyclyl ring;
wherein:
the heterocyclyl ring is optionally substituted with one or two substituents independently selected from the group consisting of: cyano, hydroxyl, C$_{1-3}$alkyl, C$_{1-3}$alkoxyl, CH$_2$OH and —CO$_2$H;
c) C3-6 cycloalkyl optionally substituted with one or two substituents independently selected from the group consisting of cyano, halo, hydroxyl, C$_{1-3}$alkyl, C$_{1-3}$alkoxyl, CO$_2$H and a 4-6 membered heterocyclyl ring;
d) —O—C$_{3-6}$ cycloalkyl;
wherein:
the cycloalkyl group is optionally substituted with one or two substituents independently selected from the group consisting of cyano, hydroxyl, C$_{1-3}$alkyl, C$_{1-3}$alkoxyl, CH$_2$OH and CO$_2$H; and
e) C$_{1-6}$alkoxy optionally substituted by one or two substituents independently selected from the group consisting of halo, hydroxyl, C$_{1-3}$alkyl, C$_{1-3}$alkoxyl, CO$_2$H and a 4-6 membered heterocyclyl ring;
R$^3$ is selected from the group consisting of halo, CN, C$_{1-3}$ alkyl, C$_{1-3}$ alkoxy, C$_{1-3}$haloalkyl, C$_{1-3}$haloalkoxy and C$_{3-6}$ cycloalkyl; and
R$^4$ is selected from the group consisting of H, halo, CN, C$_{1-3}$alkyl, C$_{1-3}$ alkoxy, C$_{1-3}$haloalkyl, C$_{1-3}$haloalkoxy and C$_{3-6}$ cycloalkyl; or
a pharmaceutically acceptable salt thereof.

2. The compound of Formula (I) or a pharmaceutically acceptable salt according to claim 1, wherein:
R$^1$ is an N-linked 6-9 membered fused bicyclic heterocyclyl ring selected from the group consisting of hexahydropyrrolo[1,2-a]pyrazin-2(1H)-yl, hexahydropyrrolo[1,2-a]pyrazine-6(2H)-yl, 3-azabicyclo[3.1.0]hexanyl and hexahydro-2H-furo[2,3-c]pyrrolyl;
wherein:
the fused bicyclic heterocyclyl optionally is substituted with one, two or three substituents independently selected from the group consisting of: oxo, halo, hydroxyl, C$_{1-3}$alkyl and C$_{1-3}$alkoxy.

3. The compound of Formula (I) or a pharmaceutically acceptable salt according to claim 1, wherein:
R$^1$ is an N-linked 7-10 membered heterospirane ring;
wherein:
the N-linked 7-10 membered heterospirane ring optionally is substituted with one substituent selected from the group consisting of: oxo, hydroxyl and C$_{1-3}$alkyl, and with the proviso that R$^1$ is not 2-oxa-6-azaspiro[3.4]octan-6-yl.

4. The compound of Formula (I) or a pharmaceutically acceptable salt according to claim 3, wherein:
R$^1$ is an N-linked 7-10 membered heterospirane ring selected from the group consisting of oxazaprio[2.5]octanyl, dioxazaspiro[2.6]nonanyl, dioxazaspiro[3.5]nonanyl, dioxazaspiro[4.4]nonanyl, diazaspiro[2.7]decanyl, diazaprio[3.6]decanyl, diazaspiro[4.5]decanyl, oxaadiazaspiro[2.7]decanyl, oxadiazaprio[3.6]decanyl and oxadiazaprio[4.5]decanyl;
wherein:
the N-linked 7-10 membered heterospirane ring of R$^1$ optionally is substituted with one oxo group.

5. The compound of Formula (I) or a pharmaceutically acceptable salt according to claim 4, wherein:
R$^1$ is an N-linked 7-10 membered heterospirane ring selected from the group consisting of 1-oxa-4,8-diazaspiro[4.5]decan-8-yl, 3-oxa-1,8-diazaspiro[4.5]decan-8-yl, 1,8-diazaspiro[4.5]decan-8-yl, 2,8-diazaspiro[4.5]decan-8-yl, 2,5-dioxa-8-azaspiro[3.5]nonan-8-yl and 4-oxa-7-azaspiro[2.5]octan-7-yl;
wherein:
the N-linked 7-10 membered heterospirane ring of R$^1$ is optionally substituted with one oxo group.

6. The compound of Formula (I) or a pharmaceutically acceptable salt according to claim 5, wherein:
R$^1$ is selected from the group consisting of 3-oxo-1-oxa-4,8-diazaspiro[4.5]decan-8-yl, 2-oxo-3-oxa-1,8-diazaspiro[4.5]decan-8-yl, 2-oxo-1,8-diazaspiro[4.5]decan-8-yl, 1-oxo-2,8-diazaspiro[4.5]decan-8-yl, 2,5-dioxa-8-azaspiro[3.5]nonan-8-yl and 4-oxa-7-azaspiro[2.5]octan-7-yl.

7. The compound of Formula (I) or a pharmaceutically acceptable salt according to claim 1, wherein:
R$^2$ is a 4-7 membered heterocyclyl ring optionally is substituted with one, two or three substituents independently selected from the group consisting of C$_{1-3}$alkyl, cyano, halo, hydroxyl, —SO$_2$CH$_3$, —COCH$_3$, and —COCH$_2$OH,
wherein:
the C$_{1-3}$alkyl group of R$^2$ optionally is substituted with one, two or three substituents independently selected from the group consisting of: halo, hydroxyl, CO$_2$H, —CH$_2$CH$_2$— and C$_{1-3}$alkoxy;
when the 4-7 membered heterocyclyl ring contains a substitutable nitrogen atom, the group of substituents identified for R$^2$ above further includes an 4-6 membered heterocyclyl ring;
wherein:
the 4-6 membered heterocyclyl ring optionally is substituted with one or two substituents independently selected from the group consisting of: cyano, halo, hydroxyl, C$_{1-3}$alkyl, C$_{1-3}$alkoxyl and CH$_2$OH;
provided that:
the 4-6 membered heterocyclyl ring is attached to the substitutable nitrogen atom of the 4-7 membered heterocyclyl ring.

8. The compound or a pharmaceutically acceptable salt according to claim 7, wherein:
R$^2$ is a 5-6 membered heterocyclyl ring optionally substituted with one, two or three substituents independently selected from the group consisting of C$_{1-3}$alkyl, halo, hydroxyl, —SO$_2$CH$_3$, —COCH$_3$, and —COCH$_2$OH,
wherein:
the C$_{1-3}$alkyl group is optionally substituted with one halo, hydroxyl or C$_{1-3}$alkoxy group,
when the 5-6 membered heterocyclyl ring contains a substitutable nitrogen atom, the group of substituents identified for R$^2$ above further includes an oxygen containing 4-6 membered heterocyclyl ring;
provided that:
the oxygen containing heterocyclyl ring is attached to said substitutable nitrogen atom of the 5-6 membered heterocyclyl ring.

9. The compound of Formula (I) or pharmaceutically acceptable salt according to claim 8, wherein:
$R^2$ is a 5-6 membered heterocyclyl ring optionally substituted with one, two or three substituents, which substituents are selected from halo
wherein:
when the 5-6 membered heterocyclyl ring contains a substitutable nitrogen atom, the group of substituents identified for $R^2$ above further includes an 4-6 membered heterocyclyl ring an oxygen containing 4-6 membered heterocyclyl ring; and
provided that:
the oxygen containing heterocyclyl ring is attached to said substitutable nitrogen atom of the 5-6 membered heterocyclyl ring.

10. The compound of Formula (I) or a pharmaceutically acceptable salt according to claim 1, wherein:
$R^2$ is $C_{3-6}$ cycloalkyl optionally is substituted with one or two substituents independently selected from the group consisting of cyano, halo, hydroxyl, $C_{1-3}$alkyl, $C_{1-3}$alkoxyl and $CO_2H$.

11. The compound of Formula (I) or a pharmaceutically acceptable salt according to claim 1, wherein:
$R^2$ is —O-4-6 membered heterocyclyl ring;
wherein:
the —O-4-6 membered heterocyclyl ring optionally is substituted with one or two substituents independently selected from the group consisting of: cyano, hydroxyl, $C_{1-3}$alkyl, $C_{1-3}$alkoxyl, $CH_2OH$ and —$CO_2H$.

12. The compound of Formula (I) or a pharmaceutically acceptable salt according to claim 1, wherein $R^3$ is selected from the group consisting of $C_{1-3}$ alkyl and $C_{1-3}$ alkoxyl.

13. The compound of Formula (I) or a pharmaceutically acceptable salt according to claim 12, wherein $R^3$ is selected from the group consisting of methyl and methoxy.

14. The compound of Formula (I) or a pharmaceutically acceptable salt according to claim 1, wherein $R^4$ is selected from the group consisting of H, chloro and methyl.

15. A pharmaceutical composition comprising a compound of Formula (I) or a pharmaceutically acceptable salt thereof according to claim 1 and at least one pharmaceutically acceptable excipient.

16. A method for treating a neurodegenerative disease, which comprises administering to a subject in need thereof a therapeutically effective amount of a compound of Formula (I) or a pharmaceutically acceptable salt according to claim 1, wherein the neurodegenerative disease is Parkinson's disease.

17. The method for treating a neurodegenerative disease according to claim 16, wherein the subject is a human.

18. The method for treating a neurodegenerative disease according to claim 17, wherein the subject is a human expressing G2019S mutation in LRRK2 kinase.

* * * * *

SEQUENCE LISTING

<160> NUMBER OF SEQ ID NOS: 10

<210> SEQ ID NO 1
<211> LENGTH: 48
<212> TYPE: DNA
<213> ORGANISM: Artificial
<220> FEATURE:
<223> OTHER INFORMATION: Primers used for PCR cloning of Human G2019
      LRRK2 plasmids preparation: pHTBV-F

<400> SEQUENCE: 1
gatctcgacg ggcgcggatc caccatggat tacaaggatg acgacgat                48

<210> SEQ ID NO 2
<211> LENGTH: 49
<212> TYPE: DNA
<213> ORGANISM: Artificial
<220> FEATURE:
<223> OTHER INFORMATION: Primers used for PCR cloning of Human G2019
      LRRK2 plasmids preparation: LRRK2 wt-F1

<400> SEQUENCE: 2
catggattac aaggatgacg acgataagat ggctagtggc agctgtcag               49

<210> SEQ ID NO 3
<211> LENGTH: 47
<212> TYPE: DNA
<213> ORGANISM: Artificial
<220> FEATURE:
<223> OTHER INFORMATION: Primers used for PCR cloning of Human G2019
      LRRK2 plasmids preparation: LRRK2 wt-R1

<400> SEQUENCE: 3
gttcacgaga tccactattc agtaagagtt ccaccaattt gggactg                 47

<210> SEQ ID NO 4
<211> LENGTH: 23
<212> TYPE: DNA
<213> ORGANISM: Artificial
<220> FEATURE:
<223> OTHER INFORMATION: Primers used for PCR cloning of Human G2019
      LRRK2 plasmids preparation: LRRK2 wt-F2

<400> SEQUENCE: 4
gaatagtgga tctcgtgaac aag                                           23

<210> SEQ ID NO 5
<211> LENGTH: 25
<212> TYPE: DNA
<213> ORGANISM: Artificial
<220> FEATURE:
<223> OTHER INFORMATION: Primers used for PCR cloning of Human G2019
      LRRK2 plasmids preparation: LRRK2 wt-R2

<400> SEQUENCE: 5
gtcagacaaa ctgcttggaa ccagc                                         25

<210> SEQ ID NO 6
<211> LENGTH: 40
<212> TYPE: DNA
<213> ORGANISM: Artificial
<220> FEATURE:
<223> OTHER INFORMATION: Primers used for PCR cloning of Human G2019
      LRRK2 plasmids preparation: LRRK2 wt-F3

<400> SEQUENCE: 6
ctggttccaa gcagtttgtc tgaccacagg cctgtgatag                         40

<210> SEQ ID NO 7
<211> LENGTH: 46
<212> TYPE: DNA
<213> ORGANISM: Artificial
<220> FEATURE:
<223> OTHER INFORMATION: Primers used for PCR cloning of Human G2019
      LRRK2 plasmids preparation: pHTBV-R

<400> SEQUENCE: 7
gttctagcca agcttggtac cctattactc aacagatgtt cgtctc                  46

<210> SEQ ID NO 8
<211> LENGTH: 7611
<212> TYPE: DNA
<213> ORGANISM: Artificial
<220> FEATURE:
<223> OTHER INFORMATION: G2019  Full length Flag-LRRK2 coding sequence

<400> SEQUENCE: 8
atggattaca aggatgacga cgataagatg gctagtggca gctgtcaggg gtgcgaagag    60
gacgaggaaa ctctgaagaa gttgatagtc aggctgaaca atgtccagga aggaaaacag   120
atagaaacgc tggtccaaat cctggaggat ctgctggtgt tcacgtactc cgagcacgcc   180
tccaagttat ttcaaggcaa aaatatccat gtgcctctgt tgatcgtctt ggactcctat   240
atgagagtcg cgagtgtgca gcaggtgggt tggtcacttc tgtgcaaatt aatagaagtc   300
tgtccaggta caatgcaaag cttaatggga ccccaggatg ttggaaatga ttgggaagtc   360
cttggtgttc accaattgat tcttaaaatg ctaacagttc ataatgccag gtaaacttg    420 tcagtgattg gactgaagac cttagatctc ctcctaactt caggtaaaat caccttgctg   480
atactggatg aagaaagtga tatttttcatg ttaattttg atgccatgca ctcatttcca   540
gccaatgatg aagtccagaa acttggatgc aaagctttac atgtgctgtt tgagagagtc   600
tcagaggagc aactgactga atttgttgag aacaaagatt atatgatatt gttaagtgcg   660
ttaacaaatt ttaaagatga agaggaaatt gtgcttcatg tgctgcattg tttcacattcc   720 ctagcgattc cttgcaataa tgtggaagtc ctcatgagtg gcaatgtcag gtgttataat   780

-continued

```
attgtggtgg aagctatgaa agcattccct atgagtgaaa gaattcaaga agtgagttgc      840
tgtttgctcc ataggcttac attaggtaat tttttcaata tcctggtatt aaacgaagtc      900
catgagtttg tggtgaaagc tgtgcagcag tacccagaga atgcagcatt gcagatctca      960
gcgctcagct gtttggccct cctcactgag actattttct aaatcaaga tttagaggaa      1020 aagaatgaga atcaagagaa tgatgatgag ggggaagaag ataaattgtt ttggctggaa      1080
gcctgttaca aagcattaac gtggcataga aagaacaagc acgtgcagga ggccgcatgc      1140
tgggcactaa ataatctcct tatgtaccaa aacagtttac atgagaagat tggagatgaa      1200
gatggccatt tcccagctca tagggaagtg atgctctcca tgctgatgca ttcttcatca      1260
aaggaagttt tccaggcatc tgcgaatgca ttgtcaactc tcttagaaca aaatgttaat      1320
ttcagaaaaa tactgttatc aaaaggaata caccctgaatg ttttggagtt aatgcagaag      1380
catatacatt ctcctgaagt ggctgaaagt ggctgtaaaa tgctaaatca tcttttttgaa    1440 ggaagcaaca cttccctgga tataatggca gcagtggtcc ccaaaatact aacagttatg      1500
aaacgtcatg agacatcatt accagtgcag ctggaggcgc ttcgagctat tttacatttt     1560
atagtgcctg gcatgccaga agaatccagg gaggatacag aatttcatca taagctaaat     1620
atggttaaaa aacagtgttt caagaatgat attcacaaac tggtcctagc agcttttgaac    1680 aggttcattg gaaatcctgg gattcagaaa tgtggattaa agtaatttc ttctattgta      1740 cattttcctg atgcattaga gatgttatcc ctggaaggtg ctatggattc agtgcttcac     1800
acactgcaga tgtatccaga tgaccaagaa attcagtgtc tgggtttaag tcttatagga    1860
tacttgatta caaagaagaa tgtgttcata ggaactggac atctgctggc aaaaattctg    1920
gtttccagct tataccgatt taaggatgtt gctgaaatac agactaaagg atttcagaca    1980
atcttagcaa tcctcaaatt gtcagcatct ttttctaagc tgctggtgca tcattcattt    2040
gacttagtaa tattccatca aatgtcttcc aatatcatgg aacaaaagga tcaacagttt    2100
ctaaacctct gttgcaagtg ttttgcaaaa gtagctatgg atgattactt aaaaaatgtg    2160
atgctagaga gagcgtgtga tcagaataac agcatcatgg ttgaatgctt gcttctattg     2220
ggagcagatg ccaatcaagc aaaggaggga tcttctttaa tttgtcaggt atgtgagaaa    2280
gagagcagtc ccaaattggt ggaactctta ctgaatagtg gatctcgtga acaagatgta    2340
cgaaaagcgt tgacgataag cattgggaaa ggtgacagcc agatcatcag cttgctctta    2400
aggaggctgg ccctggatgt ggccaacaat agcatttgcc ttggaggatt tgtatagga     2460 aaagttgaac cttcttggct tggtcctta ttttccagata agacttctaa tttaaggaaa    2520
caaacaaata tagcatctac actagcaaga atggtgatca gatatcagat gaaaagtgct    2580
gtggaagaag aacagcctc aggcagcgat ggaaatttt ctgaagatgt gctgtctaaa      2640
tttgatgaat ggacctttat tcctgactct tctatggaca gtgtgtttgc tcaaagtgat    2700
gacctggata gtgaaggaag tgaaggctca tttcttgtga aaagaaatc taattcaatt    2760 agtgtaggag aattttaccg agatgccgta ttacagcgtt gctcaccaaa tttgcaaaga    2820
cattccaatt ccttggggcc cattttgat catgaagatt tactgaagcg aaaaagaaaa     2880
atattatctt cagatgattc actcaggtca tcaaaacttc aatcccatat gaggcattca    2940
gacagcattt cttctctggc ttctgagaga gaatatatta catcactaga cctttcagca    3000
aatgaactaa gagatattga tgccctaagc cagaaatgct gtataagtgt tcatttggag    3060
catcttgaaa agctggagct tcaccagaat gcactcacga gctttccaca acagctatgt    3120
gaaactctga gagtttgac acatttggac ttgcacagta ataaatttac atcatttcct    3180
```

```
tcttatttgt tgaaaatgag ttgtattgct aatcttgatg tctctcgaaa tgacattgga   3240
ccctcagtgg ttttagatcc tacagtgaaa tgtccaactc tgaaacagtt taacctgtca   3300
tataaccagc tgtcttttgt acctgagaac ctcactgatg tggtagagaa actggagcag   3360 ctcatttag aaggaaataa aatatcaggg atatgctccc ccttgagact gaaggaactg    3420
aagattttaa accttagtaa gaaccacatt tcatccctat cagagaactt tcttgaggct   3480
tgtcctaaag tggagagttt cagtgccaga atgaattttc ttgctgctat gcctttcttg   3540
cctccttcta tgacaatcct aaaattatct cagaacaaat tttcctgtat tccagaagca   3600
attttaaatc ttccacactt gcggtcttta gatatgagca gcaatgatat tcagtaccta   3660
ccaggtcccg cacactggaa atctttgaac ttaagggaac tcttatttag ccataatcag   3720
atcagcatct tggacttgag tgaaaaagca tatttatggt ctagagtaga gaaactgcat   3780 cttctctcaca ataaactgaa agagattcct cctgagattg gctgtcttga aaatctgaca  3840
tctctggatg tcagttacaa cttggaacta agatccttc ccaatgaaat ggggaaatta   3900
agcaaaatat gggatcttcc tttggatgaa ctgcatctta actttgattt taaacatata   3960
ggatgtaaag ccaagacat cataaggttt cttcaacagc gattaaaaaa ggctgtgcct    4020
tataaccgaa tgaaacttat gattgtggga aatactggga gtggtaaaac caccttattg   4080
cagcaattaa tgaaaaccaa gaaatcagat cttggaatgc aaagtgccac agttggcata   4140
gatgtgaaag actggcctat ccaaataaga gacaaaagaa agagagatct cgtcctaaat   4200
gtgtgggatt ttgcaggtcg tgaggaattc tatagtactc atccccattt tatgacgcag   4260
cgagcattgt accttgctgt ctatgacctc agcaagggac aggctgaagt tgatgccatg   4320
aagccttggc tcttcaatat aaaggctcgc gcttcttctt ccctgtgat tctcgttggc     4380 acacatttgg atgtttctga tgagaagcaa cgcaaagcct gcatgagtaa aatcaccaag   4440
gaactcctga ataagcgagg gttccctgcc atacgagatt accactttgt gaatgccacc   4500
gaggaatctg atgctttggc aaaacttcgg aaaaccatca taaacgagag ccttaatttc   4560
aagatccgag atcagcttgt tgttggacag ctgattccag actgctatgt agaacttgaa   4620
aaaatcattt tatcggagcg taaaaatgtg ccaattgaat ttcccgtaat tgaccggaaa   4680
cgattattac aactagtgag agaaaatcag ctgcagttag atgaaaatga gcttcctcac   4740
gcagttcact ttctaaatga atcaggagtc cttcttcatt ttcaagaccc agcactgcag   4800
ttaagtgact tgtactttgt ggaacccaag tggctttgta aaatcatggc acagattttg   4860
acagtgaaag tggaaggttg tccaaaacac cctaagggaa ttatttcgcg tagagatgtg   4920 gaaaatttc tttcaaagaa aaggaaattt ccaagaact acatgtcaca gtattttaag    4980
ctcctagaaa aattccagat tgctttgcca ataggagaag aatatttgct ggttccaagc   5040
agtttgtctg accacaggcc tgtgatagag cttccccatt gtgagaactc tgaaattatc   5100
atccgactat atgaaatgcc ttattttcca atgggatttt ggtcaagatt aatcaatcga   5160
ttacttgaga tttcacctta catgctttca gggagagaac gagcacttcg cccaaacaga   5220
atgtattggc gacaaggcat ttacttaaat tggtctcctg aagcttattg tctggtagga   5280
tctgaagtct tagacaatca tccagagagt ttccttaaaaa ttacagttcc ttcttgtaga   5340 aaggctgta ttcttttggg ccaagttgtg gaccacattg attctctcat ggaagaatgg   5400
tttcctgggt tgctggagat tgatatttgt ggtgaaggag aaactctgtt gaagaaatgg   5460
gcattatata gttttaatga tggtgaagaa catcaaaaaa tcttacttga tgacttgatg   5520
```

```
aagaaagcag aggaaggaga tctcttagta aatccagatc aaccaaggct caccattcca    5580
atatctcaga ttgcccctga cttgattttg gctgacctgc ctagaaatat tatgttgaat    5640
aatgatgagt tggaatttga acaagctcca gagtttctcc taggtgatgg cagttttgga    5700
tcagtttacc gagcagccta tgaaggagaa gaagtggctg tgaagatttt taataaacat    5760
acatcactca ggctgttaag acaagagctt gtggtgcttt gccacctcca ccaccccagt    5820
ttgatatctt tgctggcagc tgggattcgt ccccggatgt tggtgatgga gttagcctcc    5880
aagggttcct tggatcgcct gcttcagcag acaaagcca gcctcactag aaccctacag     5940
cacaggattg cactccacgt agctgatggt ttgagatacc tccactcagc catgattata    6000
taccgagacc tgaaacccca caatgtgctg cttttcacac tgtatcccaa tgctgccatc    6060
attgcaaaga ttgctgacta cggcattgct cagtactgct gtagaatggg gataaaaaca    6120
tcagagggca caccagggtt tcgtgcacct gaagttgcca gaggaaatgt catttataac    6180
caacaggctg atgtttattc atttggttta ctactctatg acattttgac aactggaggt    6240
agaatagtag agggtttgaa gtttccaaat gagtttgatg aattagaaat acaaggaaaa    6300
ttacctgatc cagttaaaga atatggttgt gccccatggc ctatggttga gaaattaatt    6360
aaacagtgtt tgaaagaaaa tcctcaagaa aggcctactt ctgcccaggt ctttgacatt    6420
ttgaattcag ctgaattagt ctgtctgacg agacgcattt tattacctaa aaacgtaatt    6480
gttgaatgca tggttgctac acatcacaac agcaggaatg caagcatttg ctgggctgt     6540 gggcacaccg acagaggaca gctctcattt cttgacttaa atactgaagg atacacttct    6600
gaggaagttg ctgatagtag aatattgtgc ttagccttgg tgcatcttcc tgttgaaaag    6660
gaaagctgga ttgtgtctgg gacacagtct ggtactctcc tggtcatcaa taccgaagat    6720
gggaaaaaga gacataccct agaaaagatg actgattctg tcacttgttt gtattgcaat    6780
tccttttcca agcaaagcaa acaaaaaaat tttcttttgg ttggaaccgc tgatggcaag    6840
ttagcaattt ttgaagataa gactgttaag cttaaaggag ctgctccttt gaagatacta    6900
aatataggaa atgtcagtac tccattgatg tgtttgagtg aatccacaaa ttcaacggaa    6960
agaaatgtaa tgtggggagg atgtggcaca aagattttct cctttttctaa tgatttcacc    7020 attcagaaac tcattgagac aagaacaagc caactgtttt cttatgcagc tttcagtgat    7080
tccaacatca taacagtggt ggtagacact gctctctata ttgctaagca aaatagccct    7140
gttgtggaag tgtgggataa gaaaactgaa aaactctgtg gactaataga ctgcgtgcac    7200
tttttaaggg aggtaatggt aaaagaaaac aaggaatcaa aacacaaaat gtcttattct    7260
gggagagtga aaaccctctg ccttcagaag aacactgctc tttggatagg aactggagga    7320
ggccatattt tactcctgga tctttcaact cgtcgactta tacgtgtaat ttacaacttt    7380
tgtaattcgg tcagagtcat gatgacagca cagctaggaa gccttaaaaa tgtcatgctg    7440
gtattgggct acaaccggaa aaatactgaa ggtacacaaa agcagaaaga gatcaatct    7500 tgcttgaccg tttgggacat caatcttcca catgaagtgc aaaatttaga aaacacatt    7560 gaagtgagaa aagaattagc tgaaaaaatg agacgaacat ctgttgagta a            7611
```

<210> SEQ ID NO 9
<211> LENGTH: 2536
<212> TYPE: PRT
<213> ORGANISM: Artificial
<220> FEATURE:
<223> OTHER INFORMATION: Translated protein sequence for human G2019
     Full length LRRK2 flag tagged protein

<400> SEQUENCE: 9

```
Met Asp Tyr Lys Asp Asp Asp Lys Met Ala Ser Gly Ser Cys Gln
 1               5                  10                  15

Gly Cys Glu Glu Asp Glu Thr Leu Lys Leu Ile Val Arg Leu
             20                  25                  30

Asn Asn Val Gln Glu Gly Lys Gln Ile Glu Thr Leu Val Gln Ile Leu
             35                  40                  45

Glu Asp Leu Leu Val Phe Thr Tyr Ser Glu His Ala Ser Lys Leu Phe
 50                  55                  60

Gln Gly Lys Asn Ile His Val Pro Leu Leu Ile Val Leu Asp Ser Tyr
 65                  70                  75                  80

Met Arg Val Ala Ser Val Gln Gln Val Gly Trp Ser Leu Leu Cys Lys
                 85                  90                  95

Leu Ile Glu Val Cys Pro Gly Thr Met Gln Ser Leu Met Gly Pro Gln
                100                 105                 110

Asp Val Gly Asn Asp Trp Glu Val Leu Gly Val His Gln Leu Ile Leu
            115                 120                 125

Lys Met Leu Thr Val His Asn Ala Ser Val Asn Leu Ser Val Ile Gly
            130                 135                 140

Leu Lys Thr Leu Asp Leu Leu Thr Ser Gly Lys Ile Thr Leu Leu
145                 150                 155                 160

Ile Leu Asp Glu Glu Ser Asp Ile Phe Met Leu Ile Phe Asp Ala Met
                165                 170                 175

His Ser Phe Pro Ala Asn Asp Glu Val Gln Lys Leu Gly Cys Lys Ala
                180                 185                 190

Leu His Val Leu Phe Glu Arg Val Ser Glu Glu Gln Leu Thr Glu Phe
            195                 200                 205

Val Glu Asn Lys Asp Tyr Met Ile Leu Leu Ser Ala Leu Thr Asn Phe
            210                 215                 220

Lys Asp Glu Glu Glu Ile Val Leu His Val Leu His Cys Leu His Ser
225                 230                 235                 240

Leu Ala Ile Pro Cys Asn Asn Val Glu Val Leu Met Ser Gly Asn Val
                245                 250                 255

Arg Cys Tyr Asn Ile Val Val Glu Ala Met Lys Ala Phe Pro Met Ser
                260                 265                 270

Glu Arg Ile Gln Glu Val Ser Cys Cys Leu Leu His Arg Leu Thr Leu
            275                 280                 285

Gly Asn Phe Phe Asn Ile Leu Val Leu Asn Glu Val His Glu Phe Val
            290                 295                 300

Val Lys Ala Val Gln Gln Tyr Pro Glu Asn Ala Ala Leu Gln Ile Ser
305                 310                 315                 320

Ala Leu Ser Cys Leu Ala Leu Leu Thr Glu Thr Ile Phe Leu Asn Gln
                325                 330                 335

Asp Leu Glu Glu Lys Asn Glu Asn Gln Glu Asn Asp Asp Glu Gly Glu
            340                 345                 350

Glu Asp Lys Leu Phe Trp Leu Glu Ala Cys Tyr Lys Ala Leu Thr Trp
            355                 360                 365

His Arg Lys Asn Lys His Val Gln Glu Ala Ala Cys Trp Ala Leu Asn
            370                 375                 380

Asn Leu Leu Met Tyr Gln Asn Ser Leu His Glu Lys Ile Gly Asp Glu
385                 390                 395                 400

Asp Gly His Phe Pro Ala His Arg Glu Val Met Leu Ser Met Leu Met
                405                 410                 415
```

```
His Ser Ser Ser Lys Glu Val Phe Gln Ala Ser Ala Asn Ala Leu Ser
            420                 425                 430

Thr Leu Leu Glu Gln Asn Val Asn Phe Arg Lys Ile Leu Leu Ser Lys
        435                 440                 445

Gly Ile His Leu Asn Val Leu Glu Leu Met Gln Lys His Ile His Ser
    450                 455                 460

Pro Glu Val Ala Glu Ser Gly Cys Lys Met Leu Asn His Leu Phe Glu
465                 470                 475                 480

Gly Ser Asn Thr Ser Leu Asp Ile Met Ala Ala Val Val Pro Lys Ile
                485                 490                 495

Leu Thr Val Met Lys Arg His Glu Thr Ser Leu Pro Val Gln Leu Glu
            500                 505                 510

Ala Leu Arg Ala Ile Leu His Phe Ile Val Pro Gly Met Pro Glu Glu
        515                 520                 525

Ser Arg Glu Asp Thr Glu Phe His His Lys Leu Asn Met Val Lys Lys
    530                 535                 540

Gln Cys Phe Lys Asn Asp Ile His Lys Leu Val Leu Ala Ala Leu Asn
545                 550                 555                 560

Arg Phe Ile Gly Asn Pro Gly Ile Gln Lys Cys Gly Leu Lys Val Ile
                565                 570                 575

Ser Ser Ile Val His Phe Pro Asp Ala Leu Glu Met Leu Ser Leu Glu
            580                 585                 590

Gly Ala Met Asp Ser Val Leu His Thr Leu Gln Met Tyr Pro Asp Asp
        595                 600                 605

Gln Glu Ile Gln Cys Leu Gly Leu Ser Leu Ile Gly Tyr Leu Ile Thr
    610                 615                 620

Lys Lys Asn Val Phe Ile Gly Thr Gly His Leu Leu Ala Lys Ile Leu
625                 630                 635                 640

Val Ser Ser Leu Tyr Arg Phe Lys Asp Val Ala Glu Ile Gln Thr Lys
                645                 650                 655

Gly Phe Gln Thr Ile Leu Ala Ile Leu Lys Leu Ser Ala Ser Phe Ser
            660                 665                 670

Lys Leu Leu Val His His Ser Phe Asp Leu Val Ile Phe His Gln Met
        675                 680                 685

Ser Ser Asn Ile Met Glu Gln Lys Asp Gln Gln Phe Leu Asn Leu Cys
    690                 695                 700

Cys Lys Cys Phe Ala Lys Val Ala Met Asp Asp Tyr Leu Lys Asn Val
705                 710                 715                 720

Met Leu Glu Arg Ala Cys Asp Gln Asn Asn Ser Ile Met Val Glu Cys
                725                 730                 735

Leu Leu Leu Leu Gly Ala Asp Ala Asn Gln Ala Lys Glu Gly Ser Ser
            740                 745                 750

Leu Ile Cys Gln Val Cys Glu Lys Glu Ser Ser Pro Lys Leu Val Glu
        755                 760                 765

Leu Leu Leu Asn Ser Gly Ser Arg Glu Gln Asp Val Arg Lys Ala Leu
    770                 775                 780

Thr Ile Ser Ile Gly Lys Gly Asp Ser Gln Ile Ile Ser Leu Leu Leu
785                 790                 795                 800

Arg Arg Leu Ala Leu Asp Val Ala Asn Asn Ser Ile Cys Leu Gly Gly
                805                 810                 815

Phe Cys Ile Gly Lys Val Glu Pro Ser Trp Leu Gly Pro Leu Phe Pro
            820                 825                 830
```

```
Asp Lys Thr Ser Asn Leu Arg Lys Gln Thr Asn Ile Ala Ser Thr Leu
         835                 840                 845

Ala Arg Met Val Ile Arg Tyr Gln Met Lys Ser Ala Val Glu Glu Gly
850                 855                 860

Thr Ala Ser Gly Ser Asp Gly Asn Phe Ser Glu Asp Val Leu Ser Lys
865                 870                 875                 880

Phe Asp Glu Trp Thr Phe Ile Pro Asp Ser Ser Met Asp Ser Val Phe
                885                 890                 895

Ala Gln Ser Asp Asp Leu Asp Ser Gly Ser Glu Gly Ser Phe Leu
            900                 905                 910

Val Lys Lys Lys Ser Asn Ser Ile Ser Val Gly Glu Phe Tyr Arg Asp
            915                 920                 925

Ala Val Leu Gln Arg Cys Ser Pro Asn Leu Gln Arg His Ser Asn Ser
        930                 935                 940

Leu Gly Pro Ile Phe Asp His Glu Asp Leu Leu Lys Arg Lys Arg Lys
945                 950                 955                 960

Ile Leu Ser Ser Asp Asp Ser Leu Arg Ser Ser Lys Leu Gln Ser His
                965                 970                 975

Met Arg His Ser Asp Ser Ile Ser Ser Leu Ala Ser Glu Arg Glu Tyr
            980                 985                 990

Ile Thr Ser Leu Asp Leu Ser Ala Asn Glu Leu Arg Asp Ile Asp Ala
        995                 1000                1005

Leu Ser Gln Lys Cys Cys Ile Ser Val His Leu Glu His Leu Glu
    1010                1015                1020

Lys Leu Glu Leu His Gln Asn Ala Leu Thr Ser Phe Pro Gln Gln
    1025                1030                1035

Leu Cys Glu Thr Leu Lys Ser Leu Thr His Leu Asp Leu His Ser
    1040                1045                1050

Asn Lys Phe Thr Ser Phe Pro Ser Tyr Leu Leu Lys Met Ser Cys
    1055                1060                1065

Ile Ala Asn Leu Asp Val Ser Arg Asn Asp Ile Gly Pro Ser Val
    1070                1075                1080

Val Leu Asp Pro Thr Val Lys Cys Pro Thr Leu Lys Gln Phe Asn
    1085                1090                1095

Leu Ser Tyr Asn Gln Leu Ser Phe Val Pro Glu Asn Leu Thr Asp
    1100                1105                1110

Val Val Glu Lys Leu Glu Gln Leu Ile Leu Glu Gly Asn Lys Ile
    1115                1120                1125

Ser Gly Ile Cys Ser Pro Leu Arg Leu Lys Glu Leu Lys Ile Leu
    1130                1135                1140

Asn Leu Ser Lys Asn His Ile Ser Ser Leu Ser Glu Asn Phe Leu
    1145                1150                1155

Glu Ala Cys Pro Lys Val Glu Ser Phe Ser Ala Arg Met Asn Phe
    1160                1165                1170

Leu Ala Ala Met Pro Phe Leu Pro Pro Ser Met Thr Ile Leu Lys
    1175                1180                1185

Leu Ser Gln Asn Lys Phe Ser Cys Ile Pro Glu Ala Ile Leu Asn
    1190                1195                1200

Leu Pro His Leu Arg Ser Leu Asp Met Ser Ser Asn Asp Ile Gln
    1205                1210                1215

Tyr Leu Pro Gly Pro Ala His Trp Lys Ser Leu Asn Leu Arg Glu
    1220                1225                1230

Leu Leu Phe Ser His Asn Gln Ile Ser Ile Leu Asp Leu Ser Glu
```

```
              1235                1240                1245

Lys Ala Tyr Leu Trp Ser Arg Val Glu Lys Leu His Leu Ser His
              1250                1255                1260

Asn Lys Leu Lys Glu Ile Pro Pro Glu Ile Gly Cys Leu Glu Asn
              1265                1270                1275

Leu Thr Ser Leu Asp Val Ser Tyr Asn Leu Glu Leu Arg Ser Phe
              1280                1285                1290

Pro Asn Glu Met Gly Lys Leu Ser Lys Ile Trp Asp Leu Pro Leu
              1295                1300                1305

Asp Glu Leu His Leu Asn Phe Asp Phe Lys His Ile Gly Cys Lys
              1310                1315                1320

Ala Lys Asp Ile Ile Arg Phe Leu Gln Gln Arg Leu Lys Lys Ala
              1325                1330                1335

Val Pro Tyr Asn Arg Met Lys Leu Met Ile Val Gly Asn Thr Gly
              1340                1345                1350

Ser Gly Lys Thr Thr Leu Leu Gln Gln Leu Met Lys Thr Lys Lys
              1355                1360                1365

Ser Asp Leu Gly Met Gln Ser Ala Thr Val Gly Ile Asp Val Lys
              1370                1375                1380

Asp Trp Pro Ile Gln Ile Arg Asp Lys Arg Lys Arg Asp Leu Val
              1385                1390                1395

Leu Asn Val Trp Asp Phe Ala Gly Arg Glu Glu Phe Tyr Ser Thr
              1400                1405                1410

His Pro His Phe Met Thr Gln Arg Ala Leu Tyr Leu Ala Val Tyr
              1415                1420                1425

Asp Leu Ser Lys Gly Gln Ala Glu Val Asp Ala Met Lys Pro Trp
              1430                1435                1440

Leu Phe Asn Ile Lys Ala Arg Ala Ser Ser Ser Pro Val Ile Leu
              1445                1450                1455

Val Gly Thr His Leu Asp Val Ser Asp Glu Lys Gln Arg Lys Ala
              1460                1465                1470

Cys Met Ser Lys Ile Thr Lys Glu Leu Leu Asn Lys Arg Gly Phe
              1475                1480                1485

Pro Ala Ile Arg Asp Tyr His Phe Val Asn Ala Thr Glu Glu Ser
              1490                1495                1500

Asp Ala Leu Ala Lys Leu Arg Lys Thr Ile Ile Asn Glu Ser Leu
              1505                1510                1515

Asn Phe Lys Ile Arg Asp Gln Leu Val Val Gly Gln Leu Ile Pro
              1520                1525                1530

Asp Cys Tyr Val Glu Leu Glu Lys Ile Ile Leu Ser Glu Arg Lys
              1535                1540                1545

Asn Val Pro Ile Glu Phe Pro Val Ile Asp Arg Lys Arg Leu Leu
              1550                1555                1560

Gln Leu Val Arg Glu Asn Gln Leu Gln Leu Asp Glu Asn Glu Leu
              1565                1570                1575

Pro His Ala Val His Phe Leu Asn Glu Ser Gly Val Leu Leu His
              1580                1585                1590

Phe Gln Asp Pro Ala Leu Gln Leu Ser Asp Leu Tyr Phe Val Glu
              1595                1600                1605

Pro Lys Trp Leu Cys Lys Ile Met Ala Gln Ile Leu Thr Val Lys
              1610                1615                1620

Val Glu Gly Cys Pro Lys His Pro Lys Gly Ile Ile Ser Arg Arg
              1625                1630                1635
```

```
Asp Val Glu Lys Phe Leu Ser Lys Lys Arg Lys Phe Pro Lys Asn
1640                1645                1650

Tyr Met Ser Gln Tyr Phe Lys Leu Leu Glu Lys Phe Gln Ile Ala
1655                1660                1665

Leu Pro Ile Gly Glu Glu Tyr Leu Leu Val Pro Ser Ser Leu Ser
1670                1675                1680

Asp His Arg Pro Val Ile Glu Leu Pro His Cys Glu Asn Ser Glu
1685                1690                1695

Ile Ile Ile Arg Leu Tyr Glu Met Pro Tyr Phe Pro Met Gly Phe
1700                1705                1710

Trp Ser Arg Leu Ile Asn Arg Leu Leu Glu Ile Ser Pro Tyr Met
1715                1720                1725

Leu Ser Gly Arg Glu Arg Ala Leu Arg Pro Asn Arg Met Tyr Trp
1730                1735                1740

Arg Gln Gly Ile Tyr Leu Asn Trp Ser Pro Glu Ala Tyr Cys Leu
1745                1750                1755

Val Gly Ser Glu Val Leu Asp Asn His Pro Glu Ser Phe Leu Lys
1760                1765                1770

Ile Thr Val Pro Ser Cys Arg Lys Gly Cys Ile Leu Leu Gly Gln
1775                1780                1785

Val Val Asp His Ile Asp Ser Leu Met Glu Glu Trp Phe Pro Gly
1790                1795                1800

Leu Leu Glu Ile Asp Ile Cys Gly Glu Gly Glu Thr Leu Leu Lys
1805                1810                1815

Lys Trp Ala Leu Tyr Ser Phe Asn Asp Gly Glu Glu His Gln Lys
1820                1825                1830

Ile Leu Leu Asp Asp Leu Met Lys Lys Ala Glu Glu Gly Asp Leu
1835                1840                1845

Leu Val Asn Pro Asp Gln Pro Arg Leu Thr Ile Pro Ile Ser Gln
1850                1855                1860

Ile Ala Pro Asp Leu Ile Leu Ala Asp Leu Pro Arg Asn Ile Met
1865                1870                1875

Leu Asn Asn Asp Glu Leu Glu Phe Glu Gln Ala Pro Glu Phe Leu
1880                1885                1890

Leu Gly Asp Gly Ser Phe Gly Ser Val Tyr Arg Ala Ala Tyr Glu
1895                1900                1905

Gly Glu Glu Val Ala Val Lys Ile Phe Asn Lys His Thr Ser Leu
1910                1915                1920

Arg Leu Leu Arg Gln Glu Leu Val Val Leu Cys His Leu His His
1925                1930                1935

Pro Ser Leu Ile Ser Leu Leu Ala Ala Gly Ile Arg Pro Arg Met
1940                1945                1950

Leu Val Met Glu Leu Ala Ser Lys Gly Ser Leu Asp Arg Leu Leu
1955                1960                1965

Gln Gln Asp Lys Ala Ser Leu Thr Arg Thr Leu Gln His Arg Ile
1970                1975                1980

Ala Leu His Val Ala Asp Gly Leu Arg Tyr Leu His Ser Ala Met
1985                1990                1995

Ile Ile Tyr Arg Asp Leu Lys Pro His Asn Val Leu Leu Phe Thr
2000                2005                2010

Leu Tyr Pro Asn Ala Ala Ile Ile Ala Lys Ile Ala Asp Tyr Gly
2015                2020                2025
```

```
Ile Ala Gln Tyr Cys Cys Arg Met Gly Ile Lys Thr Ser Glu Gly
2030                2035                2040

Thr Pro Gly Phe Arg Ala Pro Glu Val Ala Arg Gly Asn Val Ile
2045                2050                2055

Tyr Asn Gln Gln Ala Asp Val Tyr Ser Phe Gly Leu Leu Leu Tyr
2060                2065                2070

Asp Ile Leu Thr Thr Gly Gly Arg Ile Val Glu Gly Leu Lys Phe
2075                2080                2085

Pro Asn Glu Phe Asp Glu Leu Glu Ile Gln Gly Lys Leu Pro Asp
2090                2095                2100

Pro Val Lys Glu Tyr Gly Cys Ala Pro Trp Pro Met Val Glu Lys
2105                2110                2115

Leu Ile Lys Gln Cys Leu Lys Glu Asn Pro Gln Glu Arg Pro Thr
2120                2125                2130

Ser Ala Gln Val Phe Asp Ile Leu Asn Ser Ala Glu Leu Val Cys
2135                2140                2145

Leu Thr Arg Arg Ile Leu Leu Pro Lys Asn Val Ile Val Glu Cys
2150                2155                2160

Met Val Ala Thr His His Asn Ser Arg Asn Ala Ser Ile Trp Leu
2165                2170                2175

Gly Cys Gly His Thr Asp Arg Gly Gln Leu Ser Phe Leu Asp Leu
2180                2185                2190

Asn Thr Glu Gly Tyr Thr Ser Glu Glu Val Ala Asp Ser Arg Ile
2195                2200                2205

Leu Cys Leu Ala Leu Val His Leu Pro Val Glu Lys Glu Ser Trp
2210                2215                2220

Ile Val Ser Gly Thr Gln Ser Gly Thr Leu Leu Val Ile Asn Thr
2225                2230                2235

Glu Asp Gly Lys Lys Arg His Thr Leu Glu Lys Met Thr Asp Ser
2240                2245                2250

Val Thr Cys Leu Tyr Cys Asn Ser Phe Ser Lys Gln Ser Lys Gln
2255                2260                2265

Lys Asn Phe Leu Leu Val Gly Thr Ala Asp Gly Lys Leu Ala Ile
2270                2275                2280

Phe Glu Asp Lys Thr Val Lys Leu Lys Gly Ala Ala Pro Leu Lys
2285                2290                2295

Ile Leu Asn Ile Gly Asn Val Ser Thr Pro Leu Met Cys Leu Ser
2300                2305                2310

Glu Ser Thr Asn Ser Thr Glu Arg Asn Val Met Trp Gly Gly Cys
2315                2320                2325

Gly Thr Lys Ile Phe Ser Ser Asn Asp Phe Thr Ile Gln Lys
2330                2335                2340

Leu Ile Glu Thr Arg Thr Ser Gln Leu Phe Ser Tyr Ala Ala Phe
2345                2350                2355

Ser Asp Ser Asn Ile Ile Thr Val Val Asp Thr Ala Leu Tyr
2360                2365                2370

Ile Ala Lys Gln Asn Ser Pro Val Val Glu Val Trp Asp Lys Lys
2375                2380                2385

Thr Glu Lys Leu Cys Gly Leu Ile Asp Cys Val His Phe Leu Arg
2390                2395                2400

Glu Val Met Val Lys Glu Asn Lys Glu Ser Lys His Lys Met Ser
2405                2410                2415

Tyr Ser Gly Arg Val Lys Thr Leu Cys Leu Gln Lys Asn Thr Ala
```

| | | 2420 | | | 2425 | | | | 2430 | | |
|---|---|---|---|---|---|---|---|---|---|---|---|
| Leu | Trp | Ile | Gly | Thr | Gly | Gly | His | Ile | Leu | Leu | Leu | Asp | Leu |
| | | 2435 | | | | 2440 | | | | 2445 | | | |
| Ser | Thr | Arg | Arg | Leu | Ile | Arg | Val | Ile | Tyr | Asn | Phe | Cys | Asn | Ser |
| | | 2450 | | | | 2455 | | | | 2460 | | | |
| Val | Arg | Val | Met | Met | Thr | Ala | Gln | Leu | Gly | Ser | Leu | Lys | Asn | Val |
| | | 2465 | | | | 2470 | | | | 2475 | | | |
| Met | Leu | Val | Leu | Gly | Tyr | Asn | Arg | Lys | Asn | Thr | Glu | Gly | Thr | Gln |
| | | 2480 | | | | 2485 | | | | 2490 | | | |
| Lys | Gln | Lys | Glu | Ile | Gln | Ser | Cys | Leu | Thr | Val | Trp | Asp | Ile | Asn |
| | | 2495 | | | | 2500 | | | | 2505 | | | |
| Leu | Pro | His | Glu | Val | Gln | Asn | Leu | Glu | Lys | His | Ile | Glu | Val | Arg |
| | | 2510 | | | | 2515 | | | | 2520 | | | |
| Lys | Glu | Leu | Ala | Glu | Lys | Met | Arg | Arg | Thr | Ser | Val | Glu |
| | | 2525 | | | | 2530 | | | | 2535 | | |

<210> SEQ ID NO 10
<211> LENGTH: 15
<212> TYPE: PRT
<213> ORGANISM: Artificial
<220> FEATURE:
<223> OTHER INFORMATION: 'LRRKtide' peptide

<400> SEQUENCE: 10

Arg Leu Gly Arg Asp Lys Tyr Lys Thr Leu Arg Gln Ile Arg Gln
1               5                   10                  15